(12) United States Patent
Wong et al.

(10) Patent No.: US 8,916,540 B2
(45) Date of Patent: Dec. 23, 2014

(54) ANTIBIOTIC COMPOSITIONS AND RELATED SCREENING METHODS

(75) Inventors: Chi-Huey Wong, La Jolla, CA (US); Ting-Jen Cheng, Taipei (TW); Che Alex Ma, Taipei (TW); Wei-Chieh Cheng, Taipei (TW)

(73) Assignee: Academia Sinica, Taipei (TW)

( * ) Notice: Subject to any disclaimer, the term of this patent is extended or adjusted under 35 U.S.C. 154(b) by 750 days.

(21) Appl. No.: 12/354,717

(22) Filed: Jan. 15, 2009

(65) Prior Publication Data

US 2009/0203641 A1 Aug. 13, 2009

Related U.S. Application Data

(60) Provisional application No. 61/021,279, filed on Jan. 15, 2008.

(30) Foreign Application Priority Data

Jul. 4, 2008 (TW) .............................. 97125469 A
Jul. 8, 2008 (JP) .............................. 2008-178187

(51) Int. Cl.

| | | |
|---|---|---|
| *C07K 14/195* | (2006.01) | |
| *C07K 14/26* | (2006.01) | |
| *C07K 14/315* | (2006.01) | |
| *C07K 14/25* | (2006.01) | |
| *C07K 14/235* | (2006.01) | |
| *C07K 14/32* | (2006.01) | |
| *C07K 14/31* | (2006.01) | |
| *C07K 14/21* | (2006.01) | |
| *C07K 14/33* | (2006.01) | |
| *C07K 14/255* | (2006.01) | |
| *C07K 14/22* | (2006.01) | |
| *C07K 14/265* | (2006.01) | |
| *G01N 33/573* | (2006.01) | |
| *A61K 31/19* | (2006.01) | |
| *A61K 31/715* | (2006.01) | |
| *A61K 31/427* | (2006.01) | |
| *A61K 31/365* | (2006.01) | |

(52) U.S. Cl.

CPC .......... *G01N 33/573* (2013.01); *C07K 14/3156* (2013.01); *C07K 14/32* (2013.01); *C07K 14/21* (2013.01); *C07K 14/31* (2013.01); *C07K 14/26* (2013.01); *C07K 14/235* (2013.01); *C07K 14/315* (2013.01); *C07K 14/33* (2013.01); *A61K 31/19* (2013.01); *C07K 14/195* (2013.01); *A61K 31/715* (2013.01); *C07K 14/25* (2013.01); *A61K 31/427* (2013.01); *A61K 31/365* (2013.01); *C07K 14/265* (2013.01); *C07K 14/22* (2013.01); *G01N 2333/91091* (2013.01); *C07K 14/255* (2013.01)
USPC .......................................................... 514/54

(58) Field of Classification Search
None
See application file for complete search history.

(56) References Cited

U.S. PATENT DOCUMENTS

2010/0121107 A1* 5/2010 Wong et al. .................... 564/175

OTHER PUBLICATIONS

Vollmer et al., "A Simple Screen for Murein Transglycosylase Inhibitors" Antimicrobial Agents and Chemotherapy (2000) vol. 44 No. 5, pp. 1181-1185.*
Burke et al., "Development and Application of Fluorescence Polarization Assays in Drug Discovery" Combinatorial Chemistry and High Throughput Screening (2003) vol. 6 pp. 183-194.*
Ropp et al., "Cloning and Characterization of the ponA Gene Encoding Penicillin-Binding Protein 1 from *Neisseria gonorrhoeae* and *Neisseria meningitidis*" Journal of Bacteriology (1997) vol. 179, No. 8, pp. 2783-2787.*
Offant et al., "Functional characterization of the glycosyltransferase domain of penicillin-binding protein 1a from *Thermotoga maritima*" Biochimica et Biophysica acta (2006) vol. 1764 pp. 1036-1042.*
Cheng et al., "Domain requirement of moenomycin binding to bifunctional transglycosylases and development of high-throughput discovery of antibiotics" PNAS (2008) vol. 105 No. 2, pp. 431-436.*
Silverman et al., "The Organic Chemistry of Drug Design and Drug Action", published 1992 by Academic Press, pp. 4-22.*
Preston et al., "Biological Characterization of a New Radioactive Labeling Reagent for Bacterial Penicillin-Binding Proteins" Antimicrobial Agents and Chemotherapy (1990) vol. 34 No. 5 pp. 718-721.*
Wu et al., "Site-directed mutagenesis of the mecA gene from a methicillin-resistant strain of *Staphylococcus aureus*." Journal of Bacteriology (1994) vol. 176 No. 2 pp. 443-449.*

* cited by examiner

*Primary Examiner* — Eric Olson
(74) *Attorney, Agent, or Firm* — Eckman Basu LLP

(57) ABSTRACT

Moenomycin inhibits bacterial growth by clocking the transglycosylase activity of class A penicillin-binding proteins (PBPs), which are key enzymes in bacterial cell wall synthesis. The binding affinities of moenomycin A with various truncated PBPs were compared showing that the transmembrane domain is important for moenomycin binding. Full-length class-A PBPs from 16 bacterial species were produced, and their binding activities showed a correlation with the antimicrobial activity of moenomycin against *Enterococcus faecalis* and *Staphylococcus aureus*. Moreover, a fluorescence anisotropy-based high-throughput assay was developed and used successfully for identification of transglycosylase inhibitors.

13 Claims, 14 Drawing Sheets

FIG. 1 (cont'd)

| | | | $K_D$ (µM) |
|---|---|---|---|
| Penicillin Binding Proteins (Bi-functional Transglycosylase) | TM | Transglycosylase (1-844) Transpeptidase | 0.44 ± 0.04 |
| TG + TP | | Transglycosylase (88-844) Transpeptidase | 2.36 ± 0.24 |
| TM + TG | TM | Transglycosylase (1-409) | 0.64 ± 0.10 |
| TG | | Transglycosylase (195-409) | 9.4 ± 0.1 |
| TP | | Transpeptidase (444-736) | > 10³ |

SEQUENCE LISTING

```
<160> NUMBER OF SEQ ID NOS: 16

<210> SEQ ID NO 1
<211> LENGTH: 814
<212> TYPE: PRT
<213> ORGANISM: Bordetella pertussis
<220> FEATURE:
<221> NAME/KEY: TRANSMEM
<222> LOCATION: (19)..(42)
<220> FEATURE:
<221> NAME/KEY: DOMAIN
<222> LOCATION: (70)..(289)
<220> FEATURE:
<221> NAME/KEY: DOMAIN
<222> LOCATION: (317)..(716)

<400> SEQUENCE: 1

Met Ser Lys Arg Gln Asn Ser Thr Lys Gln Asp Lys Pro Ala Lys Ser
1               5                   10                  15
```

```
Gly Ser Ala Ile Leu Arg Phe Phe Leu Lys Ala Gly Ile Phe Gly
            20                  25                  30

Gly Leu Ala Leu Cys Gly Val Leu Leu Ala Gly Met Ala Leu Ala Leu
        35                  40                  45

Ala Trp Pro Asn Leu Pro Asp Leu His Ala Met Thr Asp Tyr Arg Pro
50                  55                  60

Arg Val Pro Leu Arg Val Tyr Thr Ala Asp Arg Val Leu Ile Gly Glu
65                  70                  75                  80

Phe Gly Glu Glu Arg Arg Asn Val Leu Arg Phe Asn Glu Ile Pro Asp
                85                  90                  95

Val Met Lys Ser Ala Val Leu Ala Ala Glu Asp Asp Arg Phe Tyr Gln
            100                 105                 110

His Gly Gly Ile Asp Trp Met Gly Val Ile Arg Ala Gly Leu Thr Asn
        115                 120                 125

Leu Ile Ser Met Ser Lys Ser Gln Gly Ala Ser Thr Ile Thr Met Gln
130                 135                 140

Val Ala Arg Asn Phe Tyr Leu Ser Ser Glu Lys Thr Tyr Ser Arg Lys
145                 150                 155                 160

Phe Tyr Glu Leu Leu Leu Thr Phe Lys Ile Glu Ser Gln Leu Thr Lys
                165                 170                 175

Asp Gln Ile Leu Glu Leu Tyr Met Asn Gln Ile Tyr Leu Gly His Arg
            180                 185                 190

Ala Tyr Gly Phe Ala Ala Ala Ser Arg Thr Tyr Phe Gly Lys Pro Leu
        195                 200                 205

Ser Gln Val Thr Pro Ser Glu Ala Ala Met Leu Ala Gly Ile Pro Lys
210                 215                 220

Ala Pro Ser Arg Phe Asn Pro Ile Ser Asn Arg Pro Arg Ala Glu Leu
225                 230                 235                 240

Arg Gln Arg Tyr Val Leu Gly Arg Met Tyr Ser Leu Gly Tyr Leu Thr
                245                 250                 255

Glu Pro Glu Tyr Lys Glu Ala Met Ala Gln Pro Ile Val Ile Lys Ser
            260                 265                 270

Ala Glu Gly Thr Pro Ala Gly Gly Tyr Ala Ile His Gly Glu Tyr Val
        275                 280                 285

Ala Glu Leu Ala Arg Gln Leu Leu Tyr Asn Val Tyr Gln Asp Asn Leu
290                 295                 300

Tyr Ser Arg Gly Ile Asn Ile Tyr Thr Thr Val Gln Ser Lys Asp Gln
305                 310                 315                 320

Glu Ser Ala Tyr Arg Ala Val Arg Asp Gly Val Leu Glu Tyr Thr Arg
                325                 330                 335

Arg Ala Pro Tyr Pro Gly Pro Glu Glu Gln Leu Asp Met Pro Ala Gly
            340                 345                 350

Val Glu Asn Asp Pro Gln Ala Leu Asp Glu Phe Leu Asp Gly Val Phe
        355                 360                 365

Asp Lys Phe Ser Asp Ser Gly Asp Leu Leu Thr Ala Val Val Leu Ser
370                 375                 380

Ala Ser Pro Thr Glu Ile Lys Leu Val Arg Ser Arg Glu Val Ile
385                 390                 395                 400

Ser Ile Thr Asp Lys Lys Ala Leu Gly Val Val Ala Arg Ala Leu Thr
                405                 410                 415

Asp Lys Ala Lys Pro Glu Met Arg Leu Lys Arg Gly Ser Val Val Tyr
            420                 425                 430

Ile His Lys Tyr Asn Asp Asn Trp Glu Val Ile Asn Met Pro Ala Val
```

435                 440                 445
Gln Ala Ala Phe Val Ala Leu Ser Pro Gln Asp Gly Ala Ile Arg Ala
450                 455                 460

Met Val Gly Gly Phe Asp Phe Tyr Arg Gly Asn Phe Asn Arg Val Thr
465                 470                 475                 480

Gln Ala Trp Arg Gln Pro Gly Ser Asn Ile Lys Pro Phe Ile Tyr Ala
                485                 490                 495

Ala Ser Leu Glu Arg Gly Leu Thr Pro Ala Thr Gln Ile Ser Asp Gln
                500                 505                 510

Pro Phe Glu Leu Ser Ala Ala Gln Thr Gly Ser Lys Ala Trp His Pro
            515                 520                 525

Lys Asn Tyr Gly Asn Gln Tyr Glu Pro Met Leu Thr Met Arg Gln Gly
            530                 535                 540

Leu Tyr Lys Ser Lys Asn Met Val Ser Ile Arg Ile Leu Gln Ala Ile
545                 550                 555                 560

Gly Pro Gln Tyr Ala Gln Asp Tyr Leu Thr Arg Phe Gly Phe Asp Lys
                565                 570                 575

Ala Arg Gln Pro Ala Val Leu Pro Leu Ala Leu Gly Ala Gly Ser Val
                580                 585                 590

Thr Pro Leu Gln Leu Ala Gly Ala Tyr Ala Val Phe Ala Asn Gly Gly
            595                 600                 605

Tyr Arg Ile Thr Pro Tyr Leu Ile Asp Arg Val Thr Asp Ser Ser Gly
            610                 615                 620

Lys Val Leu Met Gln Ser Arg Pro Val Ile Gly Asp Ala Ala Ala
625                 630                 635                 640

Arg Ala Ile Asp Ala Arg Thr Ala Phe Val Met Asp Asp Met Leu Arg
                645                 650                 655

Gly Val Ala Thr Ser Gly Thr Ala Ala Arg Ala Arg Ala Thr Leu Lys
                660                 665                 670

Arg Ser Asp Val Ala Gly Lys Thr Gly Thr Thr Asn Glu Ser Val Asp
            675                 680                 685

Ala Trp Phe Ser Gly Tyr Thr Pro Ser Leu Val Ala Thr Ala Trp Leu
            690                 695                 700

Gly Phe Asp Gln Pro Lys Ser Leu Gly Ser Arg Glu Thr Gly Gly Gly
705                 710                 715                 720

Val Ala Met Pro Ile Trp Leu Asp Tyr Met Lys Asp Ala Leu Lys Gly
                725                 730                 735

Val Pro Glu Glu Lys Gln Arg Pro Arg Pro Asp Gly Leu Leu Val Glu
                740                 745                 750

Asn Gly Glu Leu Tyr Phe Ser Glu Phe Pro Pro Gly Gln Ala Val Ala
            755                 760                 765

Arg Leu Gly Leu Pro Gln Ala Gly Asp Ala Leu Gly Asp Phe Leu Asn
            770                 775                 780

Gly Leu Thr Gly Gly Asn Asp Asn Ser Ile Arg Val Ala Pro Gly Val
785                 790                 795                 800

Gly Thr Gln Gly Ser Gln Pro Trp Ser Gln Asn Ile Pro Phe
                805                 810

<210> SEQ ID NO 2
<211> LENGTH: 846
<212> TYPE: PRT
<213> ORGANISM: Citrobacter freundii
<220> FEATURE:
<221> NAME/KEY: TRANSMEM
<222> LOCATION: (64)..(86)

```
<220> FEATURE:
<221> NAME/KEY: DOMAIN
<222> LOCATION: (194)..(410)
<220> FEATURE:
<221> NAME/KEY: DOMAIN
<222> LOCATION: (444)..(732)

<400> SEQUENCE: 2
```

Met Ala Gly Asn Asp Arg Glu Pro Ile Gly Arg Lys Gly Lys Pro Ser
1               5                   10                  15

Arg Pro Val Lys Gln Lys Val Ser Arg Gln Leu Arg Asp Glu Glu
            20                  25                  30

Tyr Asp Asp Tyr Asp Asp Asp Tyr Glu Asp Glu Glu Pro Met
        35                  40                  45

Pro Arg Lys Gly Lys Gly Lys Gly Arg Lys Pro Arg Gly Lys Arg Gly
    50                  55                  60

Trp Phe Trp Leu Leu Val Lys Leu Ser Ile Val Phe Leu Val Leu Ile
65                  70                  75                  80

Ala Ile Tyr Gly Val Tyr Leu Asp Gln Lys Ile Arg Ser Arg Ile Asp
                85                  90                  95

Gly Lys Val Trp Gln Leu Pro Ala Ala Val Tyr Gly Arg Met Val Asn
            100                 105                 110

Leu Glu Pro Glu Met Pro Ile Gly Lys Asn Glu Met Val Glu Leu Leu
        115                 120                 125

Glu Ala Thr Gln Tyr Arg Gln Val Thr Lys Met Thr Arg Pro Gly Glu
    130                 135                 140

Phe Thr Val Gln Ala Lys Ser Ile Glu Met Ile Arg Arg Pro Phe Asp
145                 150                 155                 160

Phe Pro Asp Ser Lys Glu Gly Gln Val Arg Ala Arg Leu Thr Phe Asp
                165                 170                 175

Gly Asp His Leu Asp Thr Ile Glu Asn Met Asp Asn Arg Gln Phe
            180                 185                 190

Gly Phe Phe Arg Leu Asp Pro Arg Leu Ile Thr Met Leu Ser Ser Pro
        195                 200                 205

Asn Gly Glu Gln Arg Leu Phe Val Pro Arg Ser Gly Phe Pro Asp Leu
    210                 215                 220

Leu Val Asp Thr Leu Leu Ala Thr Glu Asp Arg His Phe Tyr Glu His
225                 230                 235                 240

Asp Gly Ile Ser Leu Tyr Ser Ile Gly Arg Ala Val Leu Ala Asn Leu
                245                 250                 255

Thr Ala Gly Arg Thr Val Gln Gly Ala Ser Thr Leu Thr Gln Gln Leu
            260                 265                 270

Val Lys Asn Leu Phe Leu Ser Ser Glu Arg Ser Tyr Trp Arg Lys Ala
        275                 280                 285

Asn Glu Ala Tyr Met Ala Leu Ile Met Asp Ala Gly Tyr Ser Lys Asp
    290                 295                 300

Arg Ile Leu Glu Leu Tyr Met Asn Glu Val Tyr Leu Gly Gln Ser Gly
305                 310                 315                 320

Asp Asn Glu Ile Arg Gly Phe Pro Leu Ala Ser Leu Tyr Tyr Phe Gly
                325                 330                 335

Arg Pro Val Glu Glu Leu Ser Leu Asp Gln Ala Leu Leu Val Gly
            340                 345                 350

Met Val Lys Gly Ala Ser Ile Tyr Asn Pro Trp Arg Asn Pro Lys Leu
        355                 360                 365

Ala Leu Glu Arg Arg Asn Leu Val Leu Arg Leu Leu Gln Gln Gln Gln

```
             370                 375                 380
Ile Ile Asp Gln Asp Leu Tyr Asp Met Leu Ser Ala Arg Pro Leu Gly
385                 390                 395                 400

Val Gln Pro Arg Gly Gly Val Ile Ser Pro Gln Pro Ala Phe Met Gln
                405                 410                 415

Met Val Arg Gln Glu Leu Gln Ala Lys Leu Gly Asp Lys Val Lys Asp
            420                 425                 430

Leu Ser Gly Val Lys Ile Phe Thr Thr Phe Asp Ser Val Ala Gln Asp
            435                 440                 445

Ala Ala Glu Lys Ala Ala Val Glu Gly Ile Pro Val Leu Lys Lys Gln
            450                 455                 460

Arg Lys Leu Ser Asp Leu Glu Thr Ala Ile Val Val Asp Arg Phe
465                 470                 475                 480

Ser Gly Glu Val Arg Ala Met Val Gly Gly Ala Glu Pro Gln Phe Ala
                485                 490                 495

Gly Tyr Asn Arg Ala Met Gln Ala Arg Arg Ser Ile Gly Ser Leu Ala
            500                 505                 510

Lys Pro Ala Thr Tyr Leu Thr Ala Leu Ser Gln Pro Lys Leu Tyr Arg
            515                 520                 525

Leu Asn Thr Trp Ile Arg His Ala Pro Ile Ala Leu Arg Gln Pro Asn
530                 535                 540

Gly Gln Val Trp Ser Pro Gln Asn Asp Asp Arg Arg Tyr Ser Glu Thr
545                 550                 555                 560

Gly Lys Val Met Leu Val Asp Ala Leu Thr Arg Ser Met Asn Val Pro
                565                 570                 575

Thr Val Asn Leu Gly Met Ala Leu Gly Leu Pro Ala Val Thr Asp Thr
            580                 585                 590

Trp Leu Lys Leu Gly Ala Pro Lys Asp Gln Leu Asn Pro Val Pro Ala
            595                 600                 605

Met Leu Leu Gly Ala Leu Asn Leu Thr Pro Ile Glu Val Ala Gln Ala
            610                 615                 620

Phe Gln Thr Ile Ala Ser Gly Gly Asn Arg Ala Pro Leu Ser Ala Leu
625                 630                 635                 640

Arg Ser Val Ile Ala Glu Asp Gly Thr Val Leu Tyr Gln Ser Phe Pro
                645                 650                 655

Gln Ala Glu Arg Ser Val Pro Ala Gln Ala Ala Tyr Met Thr Leu Trp
            660                 665                 670

Thr Met Gln Gln Val Val Gln Arg Gly Thr Gly Arg Gln Leu Gly Ala
            675                 680                 685

Lys Tyr Pro Gly Leu His Leu Ala Gly Lys Thr Gly Thr Thr Asn Asn
            690                 695                 700

Asn Val Asp Thr Trp Phe Ala Gly Ile Asp Gly Ser Gln Val Thr Ile
705                 710                 715                 720

Thr Trp Val Gly Arg Asp Asn Asn Gln Pro Thr Lys Leu Tyr Gly Ala
                725                 730                 735

Ser Gly Ala Met Ser Ile Tyr Gln Arg Tyr Leu Ala Asn Gln Thr Pro
            740                 745                 750

Thr Pro Leu Val Leu Thr Pro Pro Glu Asp Val Val Asp Met Gly Val
            755                 760                 765

Asp Tyr Asp Gly Asn Phe Val Cys Ser Gly Gly Met Arg Thr Leu Pro
            770                 775                 780

Val Trp Thr Thr Asp Pro Asp Ser Leu Cys Gln Gln Gly Glu Met Met
785                 790                 795                 800
```

```
Gln Gln Pro Thr Gly Asn Pro Phe Asp Gln Ser Thr Pro Gln Gln Gln
                805                 810                 815

Pro Gln Gln Gln Gln Gln Pro Ala Gln Gln Glu Lys Lys Asp Ser
        820                 825                 830

Asp Gly Val Ala Gly Trp Ile Lys Asp Met Phe Gly Ser Asn
        835                 840                 845

<210> SEQ ID NO 3
<211> LENGTH: 844
<212> TYPE: PRT
<213> ORGANISM: Escherichia coli
<220> FEATURE:
<221> NAME/KEY: TRANSMEM
<222> LOCATION: (64)..(87)
<220> FEATURE:
<221> NAME/KEY: DOMAIN
<222> LOCATION: (194)..(410)
<220> FEATURE:
<221> NAME/KEY: DOMAIN
<222> LOCATION: (444)..(732)

<400> SEQUENCE: 3

Met Ala Gly Asn Asp Arg Glu Pro Ile Gly Arg Lys Gly Lys Pro Thr
1               5                   10                  15

Arg Pro Val Lys Gln Lys Val Ser Arg Arg Tyr Glu Asp Asp Asp
            20                  25                  30

Asp Tyr Asp Asp Tyr Asp Asp Tyr Glu Asp Glu Pro Met Pro Arg
        35                  40                  45

Lys Gly Lys Gly Lys Gly Lys Gly Arg Lys Pro Arg Gly Lys Arg Gly
50                  55                  60

Trp Leu Trp Leu Leu Leu Lys Leu Ala Ile Val Phe Ala Val Leu Ile
65                  70                  75                  80

Ala Ile Tyr Gly Val Tyr Leu Asp Gln Lys Ile Arg Ser Arg Ile Asp
                85                  90                  95

Gly Lys Val Trp Gln Leu Pro Ala Ala Val Tyr Gly Arg Met Val Asn
            100                 105                 110

Leu Glu Pro Asp Met Thr Ile Ser Lys Asn Glu Met Val Lys Leu Leu
        115                 120                 125

Glu Ala Thr Gln Tyr Arg Gln Val Ser Lys Met Thr Arg Pro Gly Glu
130                 135                 140

Phe Thr Val Gln Ala Asn Ser Ile Glu Met Ile Arg Arg Pro Phe Asp
145                 150                 155                 160

Phe Pro Asp Ser Lys Glu Gly Gln Val Arg Ala Arg Leu Thr Phe Asp
                165                 170                 175

Gly Asp His Leu Ala Thr Ile Val Asn Met Glu Asn Asn Arg Gln Phe
            180                 185                 190

Gly Phe Phe Arg Leu Asp Pro Arg Leu Ile Thr Met Ile Ser Ser Pro
        195                 200                 205

Asn Gly Glu Gln Arg Leu Phe Val Pro Arg Ser Gly Phe Pro Asp Leu
210                 215                 220

Leu Val Asp Thr Leu Leu Ala Thr Glu Asp Arg His Phe Tyr Glu His
225                 230                 235                 240

Asp Gly Ile Ser Leu Tyr Ser Ile Gly Arg Ala Val Leu Ala Asn Leu
                245                 250                 255

Thr Ala Gly Arg Thr Val Gln Gly Ala Ser Thr Leu Thr Gln Gln Leu
            260                 265                 270

Val Lys Asn Leu Phe Leu Ser Ser Glu Arg Ser Tyr Trp Arg Lys Ala
```

```
                    275                 280                 285
        Asn Glu Ala Tyr Met Ala Leu Ile Met Asp Ala Arg Tyr Ser Lys Asp
        290                 295                 300
        Arg Ile Leu Glu Leu Tyr Met Asn Glu Val Tyr Leu Gly Gln Ser Gly
        305                 310                 315                 320
        Asp Asn Glu Ile Arg Gly Phe Pro Leu Ala Ser Leu Tyr Tyr Phe Gly
                            325                 330                 335
        Arg Pro Val Glu Glu Leu Ser Leu Asp Gln Gln Ala Leu Leu Val Gly
                            340                 345                 350
        Met Val Lys Gly Ala Ser Ile Tyr Asn Pro Trp Arg Asn Pro Lys Leu
                    355                 360                 365
        Ala Leu Glu Arg Arg Asn Leu Val Leu Arg Leu Leu Gln Gln Gln Gln
        370                 375                 380
        Ile Ile Asp Gln Glu Leu Tyr Asp Met Leu Ser Ala Arg Pro Leu Gly
        385                 390                 395                 400
        Val Gln Pro Arg Gly Gly Val Ile Ser Pro Gln Pro Ala Phe Met Gln
                            405                 410                 415
        Leu Val Arg Gln Glu Leu Gln Ala Lys Leu Gly Asp Lys Val Lys Asp
                            420                 425                 430
        Leu Ser Gly Val Lys Ile Phe Thr Thr Phe Asp Ser Val Ala Gln Asp
                    435                 440                 445
        Ala Ala Glu Lys Ala Ala Val Glu Gly Ile Pro Ala Leu Lys Lys Gln
        450                 455                 460
        Arg Lys Leu Ser Asp Leu Glu Thr Ala Ile Val Val Asp Arg Phe
        465                 470                 475                 480
        Ser Gly Glu Val Arg Ala Met Val Gly Gly Ser Glu Pro Gln Phe Ala
                            485                 490                 495
        Gly Tyr Asn Arg Ala Met Gln Ala Arg Arg Ser Ile Gly Ser Leu Ala
                            500                 505                 510
        Lys Pro Ala Thr Tyr Leu Thr Ala Leu Ser Gln Pro Lys Ile Tyr Arg
                    515                 520                 525
        Leu Asn Thr Trp Ile Ala Asp Ala Pro Ile Ala Leu Arg Gln Pro Asn
        530                 535                 540
        Gly Gln Val Trp Ser Pro Gln Asn Asp Asp Arg Arg Tyr Ser Glu Ser
        545                 550                 555                 560
        Gly Arg Val Met Leu Val Asp Ala Leu Thr Arg Ser Met Asn Val Pro
                            565                 570                 575
        Thr Val Asn Leu Gly Met Ala Leu Gly Leu Pro Ala Val Thr Glu Thr
                            580                 585                 590
        Trp Ile Lys Leu Gly Val Pro Lys Asp Gln Leu His Pro Val Pro Ala
                    595                 600                 605
        Met Leu Leu Gly Ala Leu Asn Leu Thr Pro Ile Glu Val Ala Gln Ala
        610                 615                 620
        Phe Gln Thr Ile Ala Ser Gly Gly Asn Arg Ala Pro Leu Ser Ala Leu
        625                 630                 635                 640
        Arg Ser Val Ile Ala Glu Asp Gly Lys Val Leu Tyr Gln Ser Phe Pro
                            645                 650                 655
        Gln Ala Glu Arg Ala Val Pro Ala Gln Ala Ala Tyr Leu Thr Leu Trp
                            660                 665                 670
        Thr Met Gln Gln Val Val Gln Arg Gly Thr Gly Arg Gln Leu Gly Ala
                    675                 680                 685
        Lys Tyr Pro Asn Leu His Leu Ala Gly Lys Thr Gly Thr Thr Asn Asn
        690                 695                 700
```

```
Asn Val Asp Thr Trp Phe Ala Gly Ile Asp Gly Ser Thr Val Thr Ile
705                 710                 715                 720

Thr Trp Val Gly Arg Asp Asn Asn Gln Pro Thr Lys Leu Tyr Gly Ala
            725                 730                 735

Ser Gly Ala Met Ser Ile Tyr Gln Arg Tyr Leu Ala Asn Gln Thr Pro
            740                 745                 750

Thr Pro Leu Asn Leu Val Pro Pro Glu Asp Ile Ala Asp Met Gly Val
            755                 760                 765

Asp Tyr Asp Gly Asn Phe Val Cys Ser Gly Gly Met Arg Ile Leu Pro
            770                 775                 780

Val Trp Thr Ser Asp Pro Gln Ser Leu Cys Gln Ser Glu Met Gln
785                 790                 795                 800

Gln Gln Pro Ser Gly Asn Pro Phe Asp Gln Ser Ser Gln Pro Gln Gln
            805                 810                 815

Gln Pro Gln Gln Gln Pro Ala Gln Gln Glu Gln Lys Asp Ser Asp Gly
            820                 825                 830

Val Ala Gly Trp Ile Lys Asp Met Phe Gly Ser Asn
            835                 840

<210> SEQ ID NO 4
<211> LENGTH: 781
<212> TYPE: PRT
<213> ORGANISM: Haemophilus influenzae
<220> FEATURE:
<221> NAME/KEY: TRANSMEM
<222> LOCATION: (20)..(44)
<220> FEATURE:
<221> NAME/KEY: DOMAIN
<222> LOCATION: (150)..(364)
<220> FEATURE:
<221> NAME/KEY: DOMAIN
<222> LOCATION: (400)..(686)

<400> SEQUENCE: 4

Met Thr Ser Gln His Ser Ala Lys Lys Ser Ser Lys Asn Thr Pro Lys
1               5                   10                  15

Asn Asn Arg Thr Phe Lys Gly Phe Leu Leu Lys Phe Ser Phe Thr Ala
            20                  25                  30

Leu Val Leu Thr Ile Phe Tyr Gly Gly Tyr Leu Asp Trp Gln Ile Arg
            35                  40                  45

Ser Lys Met Asp Gly Gln Ile Trp His Leu Pro Ala Glu Val Tyr Ser
            50                  55                  60

Arg Leu Glu Ser Val Lys Ile Ala Asp Asn Leu Ala Phe Asp Glu Val
65                  70                  75                  80

Ile Gln Ile Leu Leu Asp Asn Glu Tyr Arg Gln Thr Thr Met Val Ala
            85                  90                  95

Ala Pro Gly Asp Phe Lys Leu Glu Asp Asp Ser Ile Val Ile Leu Arg
            100                 105                 110

Arg Ala Phe Pro Phe Pro Asp Lys Ala Glu Pro Gln Arg Val Leu Arg
            115                 120                 125

Leu Arg Phe Ser His Asn Lys Leu Ser Arg Ile Glu Asp Leu Val Thr
            130                 135                 140

Val Lys Thr Val Asp Glu Phe Arg Leu Ala Pro Lys Leu Ile Ala Met
145                 150                 155                 160

Leu Gln Ser Asp Asn Glu Asp Arg Leu Ala Ile Pro Leu Gln Asn Tyr
            165                 170                 175

Pro Arg Leu Leu Ile Asp Thr Leu Ile Leu Thr Glu Asp Arg Arg Phe
```

```
            180                 185                 190
Tyr Glu His Asn Gly Ile Asn Pro Val Gly Ile Leu Arg Ala Leu Ile
            195                 200                 205
Ala Asn Ile Arg Ala Gly Gln Thr Val Gln Gly Gly Ser Thr Leu Thr
            210                 215                 220
Gln Gln Leu Val Lys Asn Leu Phe Leu Ser Arg Glu Arg Thr Ile Thr
225                 230                 235                 240
Arg Lys Ala Asn Glu Ala Leu Met Ser Leu Val Leu Asp Trp Arg Tyr
                245                 250                 255
Asp Lys Asn Arg Ile Leu Glu Thr Tyr Leu Asn Glu Ile Tyr Leu Gly
            260                 265                 270
Gln Asn Gly Asp Thr Gln Ile His Gly Phe Glu Leu Ala Ser Gln Phe
            275                 280                 285
Tyr Phe Gly Arg Ser Ile Arg Glu Ile Ser Leu Asp Gln Ile Ala Leu
            290                 295                 300
Leu Val Gly Met Val Lys Gly Pro Ser Leu Tyr Asn Pro Trp Arg Asn
305                 310                 315                 320
Pro Gln Asn Ala Leu Glu Arg Arg Asn Ile Val Leu Arg Leu Met Leu
                325                 330                 335
Glu His Lys Met Ile Gly Asp Glu Leu Tyr Gln Leu Leu Ser Gln Arg
            340                 345                 350
Pro Leu Gly Val Gln Lys Lys Gly Gln Ile Ser Arg Lys Tyr Pro Ala
            355                 360                 365
Phe Ile Gln Thr Leu Gln Ala Asp Leu Arg Arg Glu Leu Gly Glu His
            370                 375                 380
Lys Ile Ser Ser Leu Leu Gly Ala Arg Ile Phe Ser Thr Met Asp Leu
385                 390                 395                 400
Lys Gln Gln Ala Gln Ala Glu Asn Ala Val Val Asn Thr Val Ser Gln
                405                 410                 415
Leu Gln Leu Lys Met Lys Asn Pro His Leu Glu Gly Ala Met Ile Ile
            420                 425                 430
Thr Asp Tyr Arg Thr Gly Glu Ile Arg Ala Val Val Gly Gly Leu Gln
            435                 440                 445
Thr Gln Tyr Ala Gly Phe Asn Arg Ala Leu Met Ala Lys Arg Gln Ile
            450                 455                 460
Gly Ser Leu Val Lys Pro Ser Ile Tyr Leu Thr Ala Leu Ser Asn Pro
465                 470                 475                 480
Glu Gln Phe Arg Leu Asn Thr Pro Ile Asn Asn Gln Pro Ile Thr Ile
                485                 490                 495
Asn Val Lys Gly Ser Pro Pro Trp Gln Pro Arg Asn Tyr Asp Lys Lys
            500                 505                 510
Tyr Ser Asp Ser Val Met Leu Met Asp Ala Leu Ala Arg Ser Leu Asn
            515                 520                 525
Ile Pro Thr Val Asn Ile Gly Met Lys Val Gly Leu Ser Lys Val Ile
            530                 535                 540
Asp Thr Gln Lys Ala Met Gly Trp Asp Asn Val Glu Ile Pro Lys Val
545                 550                 555                 560
Pro Ala Met Leu Leu Gly Ser Tyr Ser Ile Ser Pro Tyr Asp Val Thr
                565                 570                 575
Lys Leu Tyr Gln Thr Leu Ala Asn Gly Gly Arg Ile Ala Leu Thr
            580                 585                 590
Thr Val Asp Ser Ile Ala Asp Arg Gln Gly Asn Leu Ile Phe Gln His
            595                 600                 605
```

```
Asp Lys Ser Ala Lys Gln Val Pro Gln Glu Ala Ala Phe Gln Thr
        610                 615                 620

Leu Phe Ala Met Gln Gln Thr Val Glu Arg Gly Thr Ala Arg Ser Leu
625                 630                 635                 640

Gln Lys Asp Tyr Ala Asp Leu His Leu Ala Gly Lys Thr Gly Thr Thr
                645                 650                 655

Asn Glu Ser Arg Asp Thr Trp Phe Val Gly Ile Asp Gly Lys Asn Ile
                660                 665                 670

Ser Thr Val Trp Leu Gly Arg Asp Asn Gly Glu Thr Lys Leu Thr
        675                 680                 685

Gly Ala Ser Gly Ala Leu Gln Ile Tyr Lys Asp Tyr Leu Asn Arg Thr
        690                 695                 700

Asn Ile Glu Lys Leu Ala Ile Thr Pro Pro Thr Thr Val Lys Trp Val
705                 710                 715                 720

Gly Ile Asn Gln Tyr Gly Asp Trp Asp Cys Glu Ser Tyr Arg Thr Ile
                725                 730                 735

Pro Val Trp Leu Asn Asn Gly Gln Asn Phe Cys Gly Glu Thr Ser Ser
                740                 745                 750

Pro Ser Leu Thr Pro Thr Thr Glu Thr Glu Thr Pro Pro Gln Glu Ser
        755                 760                 765

Leu Trp Asp Val Leu Asp Asn Pro Asn Pro Pro Ala Gln
770                 775                 780

<210> SEQ ID NO 5
<211> LENGTH: 660
<212> TYPE: PRT
<213> ORGANISM: Helicobacter pylori
<220> FEATURE:
<221> NAME/KEY: TRANSMEM
<222> LOCATION: (5)..(20)
<220> FEATURE:
<221> NAME/KEY: DOMAIN
<222> LOCATION: (49)..(252)
<220> FEATURE:
<221> NAME/KEY: DOMAIN
<222> LOCATION: (290)..(590)

<400> SEQUENCE: 5

Met Leu Lys Lys Ile Phe Tyr Gly Phe Ile Val Leu Phe Leu Ile
1               5                   10                  15

Val Gly Leu Leu Ala Val Leu Val Ala Gln Val Trp Val Thr Thr Asp
                20                  25                  30

Lys Asp Ile Ala Lys Ile Lys Asp Tyr Arg Pro Ser Val Ala Ser Gln
                35                  40                  45

Ile Leu Asp Arg Lys Gly Arg Leu Ile Ala Asn Ile Tyr Asp Lys Glu
        50                  55                  60

Phe Arg Phe Tyr Ala Arg Phe Glu Glu Ile Pro Pro Arg Phe Val Glu
65                  70                  75                  80

Ser Leu Leu Ala Val Glu Asp Thr Leu Phe Phe Glu His Gly Gly Ile
                85                  90                  95

Asn Leu Asp Ala Val Met Arg Ala Met Ile Lys Asn Ala Lys Ser Gly
                100                 105                 110

Arg Tyr Thr Glu Gly Gly Ser Thr Leu Thr Gln Gln Leu Val Lys Asn
                115                 120                 125

Met Val Leu Thr Arg Glu Lys Thr Leu Thr Arg Lys Leu Lys Glu Ala
        130                 135                 140

Ile Ile Ser Ile Arg Ile Glu Lys Val Leu Ser Lys Glu Glu Ile Leu
```

```
                145                 150                 155                 160
Glu Arg Tyr Leu Asn Gln Thr Phe Phe Gly His Gly Tyr Tyr Gly Val
                    165                 170                 175
Lys Thr Ala Ser Leu Gly Tyr Phe Lys Lys Pro Leu Asp Lys Leu Thr
                180                 185                 190
Leu Lys Glu Ile Thr Met Leu Val Ala Leu Pro Arg Ala Pro Ser Phe
                195                 200                 205
Tyr Asp Pro Thr Lys Asn Leu Glu Phe Ser Leu Ser Arg Ala Asn Asp
            210                 215                 220
Ile Leu Arg Arg Leu Tyr Ser Leu Gly Trp Ile Ser Ser Asn Glu Leu
225                 230                 235                 240
Lys Ser Ala Leu Asn Glu Val Pro Ile Val Tyr Asn Gln Thr Ser Thr
                    245                 250                 255
Gln Asn Ile Ala Pro Tyr Val Val Asp Glu Val Leu Lys Gln Leu Asp
                260                 265                 270
Gln Leu Asp Gly Leu Lys Thr Gln Gly Tyr Thr Ile Lys Leu Thr Ile
                275                 280                 285
Asp Leu Asp Tyr Gln Arg Leu Ala Leu Glu Ser Leu Arg Phe Gly His
            290                 295                 300
Gln Lys Ile Leu Glu Lys Ile Ala Lys Glu Lys Pro Lys Thr Asn Ala
305                 310                 315                 320
Ser Asn Asp Lys Asp Glu Asp Asn Leu Asn Ala Ser Met Ile Val Thr
                    325                 330                 335
Glu Thr Ser Thr Gly Lys Ile Leu Ala Leu Val Gly Gly Ile Asp Tyr
                340                 345                 350
Lys Lys Ser Ala Phe Asn Arg Ala Thr Gln Ala Lys Arg Gln Phe Gly
                355                 360                 365
Ser Ala Ile Lys Pro Phe Val Tyr Gln Ile Ala Phe Asp Asn Gly Tyr
            370                 375                 380
Ser Thr Thr Ser Lys Ile Pro Asp Thr Ala Arg Asn Phe Glu Asn Gly
385                 390                 395                 400
Asn Tyr Ser Lys Asn Ser Val Gln Asn His Ala Trp His Pro Ser Asn
                    405                 410                 415
Tyr Thr Arg Lys Phe Leu Gly Leu Val Thr Leu Gln Glu Ala Leu Ser
                420                 425                 430
His Ser Leu Asn Leu Ala Thr Ile Asn Leu Ser Asp Gln Leu Gly Phe
                435                 440                 445
Glu Lys Ile Tyr Gln Ser Leu Ser Asp Met Gly Phe Lys Asn Leu Pro
            450                 455                 460
Lys Asp Leu Ser Ile Val Leu Gly Ser Phe Ala Ile Ser Pro Ile Asp
465                 470                 475                 480
Ala Ala Glu Lys Tyr Ser Leu Phe Ser Asn Tyr Gly Thr Met Leu Lys
                    485                 490                 495
Pro Met Leu Ile Glu Ser Ile Thr Asn Gln Gln Asn Glu Val Lys Thr
                500                 505                 510
Phe Thr Pro Ile Glu Thr Lys Lys Ile Thr Ser Lys Glu Gln Ala Phe
                515                 520                 525
Leu Thr Leu Ser Ala Leu Met Asp Ala Val Glu Asn Gly Thr Gly Ser
            530                 535                 540
Leu Ala Arg Ile Lys Gly Leu Glu Ile Ala Gly Lys Thr Gly Thr Ser
545                 550                 555                 560
Asn Asn Asn Ile Asp Ala Trp Phe Ile Gly Phe Thr Pro Thr Leu Gln
                    565                 570                 575
```

```
Ser Val Ile Trp Phe Gly Arg Asp Asp Asn Thr Pro Ile Gly Lys Gly
            580                 585                 590

Ala Thr Gly Gly Val Val Ser Ala Pro Val Tyr Ser Tyr Phe Met Arg
            595                 600                 605

Asn Ile Leu Ala Ile Glu Pro Ser Leu Lys Arg Lys Phe Asp Val Pro
            610                 615                 620

Lys Gly Leu Arg Lys Glu Ile Val Asp Lys Ile Pro Tyr Tyr Ser Ser
625                 630                 635                 640

Pro Asn Ser Ile Thr Pro Thr Pro Lys Lys Thr Asp Ser Glu Glu
                645                 650                 655

Arg Leu Leu Phe
            660

<210> SEQ ID NO 6
<211> LENGTH: 850
<212> TYPE: PRT
<213> ORGANISM: Klebsiella pneumoniae
<220> FEATURE:
<221> NAME/KEY: TRANSMEM
<222> LOCATION: (64)..(87)
<220> FEATURE:
<221> NAME/KEY: DOMAIN
<222> LOCATION: (254)..(410)
<220> FEATURE:
<221> NAME/KEY: DOMAIN
<222> LOCATION: (444)..(733)

<400> SEQUENCE: 6

Met Ala Gly Asp Asp Arg Glu Pro Ile Gly Lys Gly Arg Pro Ser
1               5                   10                  15

Arg Pro Thr Lys Gln Lys Val Thr Arg Arg Val Arg Glu Glu Asp
            20                  25                  30

Tyr Asp Asp Glu Tyr Asp Asp Asp Tyr Glu Asp Glu Lys Pro Val
            35                  40                  45

Pro Arg Lys Ala Lys Gly Lys Gly Gly Lys Pro Arg Ala Lys Arg Ser
            50                  55                  60

Trp Leu Trp Leu Leu Val Lys Leu Gly Ile Val Phe Ala Val Leu Ile
65                  70                  75                  80

Ala Ala Tyr Gly Val Tyr Leu Asp Gln Lys Ile Arg Ser Arg Ile Asp
                85                  90                  95

Gly Lys Val Trp Glu Leu Pro Ala Ala Val Tyr Gly Arg Met Val Asn
            100                 105                 110

Leu Glu Pro Asp Met Gln Ile Ser Lys Asn Glu Met Val Arg Leu Leu
            115                 120                 125

Asn Ala Thr Gln Tyr Arg Gln Val Ser Ala Met Thr Arg Pro Gly Glu
            130                 135                 140

Tyr Thr Val Gln Ala Asn Ser Ile Glu Met Ile Arg Arg Pro Phe Asp
145                 150                 155                 160

Phe Pro Asp Ser Lys Glu Gly Gln Val Arg Ala Arg Leu Thr Phe Asp
                165                 170                 175

Gly Asp His Leu Glu Thr Ile Glu Asn Met Asp Asn Asn Arg Gln Phe
            180                 185                 190

Gly Phe Phe Arg Leu Asp Pro Arg Leu Ile Thr Met Leu Gln Ser Pro
            195                 200                 205

Asn Gly Glu Gln Arg Leu Phe Val Lys Arg Ser Gly Phe Pro Asp Leu
            210                 215                 220

Leu Val Asp Thr Leu Leu Ala Thr Glu Asp Arg His Phe Tyr Glu His
```

-continued

```
            225                 230                 235                 240
Asp Gly Ile Ser Leu Tyr Ser Ile Gly Arg Ala Val Leu Ala Asn Leu
                245                 250                 255

Thr Ala Gly Arg Thr Val Gln Gly Ala Ser Thr Leu Thr Gln Gln Leu
                260                 265                 270

Val Lys Asn Leu Phe Leu Ser Ser Glu Arg Ser Tyr Trp Arg Lys Ala
                275                 280                 285

Asn Glu Ala Tyr Met Ala Leu Ile Val Asp Ala Arg Tyr Ser Lys Asp
                290                 295                 300

Arg Ile Leu Glu Leu Tyr Met Asn Glu Val Tyr Leu Gly Gln Ser Gly
305                 310                 315                 320

Asp Asn Glu Ile Arg Gly Phe Pro Leu Ala Ser Leu Tyr Tyr Phe Gly
                325                 330                 335

Arg Pro Val Glu Glu Leu Ser Leu Asp Gln Gln Ala Leu Leu Val Gly
                340                 345                 350

Met Val Lys Gly Ala Ser Val Tyr Asn Pro Trp Arg Asn Pro Lys Leu
                355                 360                 365

Ala Leu Glu Arg Arg Asn Leu Val Leu Arg Leu Gln Gln Gln Gln
                370                 375                 380

Val Ile Asp Gln Glu Leu Tyr Asp Met Leu Ser Ala Arg Pro Leu Gly
385                 390                 395                 400

Val Gln Pro Arg Gly Gly Val Ile Ser Pro Gln Pro Ala Phe Met Gln
                405                 410                 415

Met Val Arg Gln Glu Leu Gln Ala Lys Leu Gly Asp Lys Val Lys Asp
                420                 425                 430

Leu Ser Gly Val Lys Ile Phe Thr Thr Phe Asp Ser Val Ala Gln Asp
                435                 440                 445

Ala Ala Glu Lys Ala Ala Ser Glu Gly Ile Pro Val Leu Lys Lys Gln
                450                 455                 460

Arg Lys Leu Ala Asp Leu Glu Thr Ala Met Val Val Asp Arg Phe
465                 470                 475                 480

Thr Gly Glu Val Arg Ala Met Val Gly Gly Ala Glu Pro Gln Phe Ala
                485                 490                 495

Gly Tyr Asn Arg Ala Met Gln Ala Arg Arg Ser Ile Gly Ser Leu Ala
                500                 505                 510

Lys Pro Ala Thr Tyr Leu Thr Ala Leu Ser Gln Pro Asn Gln Tyr Arg
                515                 520                 525

Leu Asn Thr Trp Ile Ala Asp Ala Pro Val Thr Ile Arg Leu Ser Asn
                530                 535                 540

Gly Gln Thr Trp Ser Pro Gln Asn Asp Asp Arg Arg Phe Ser Gly Gln
545                 550                 555                 560

Val Met Leu Val Asp Ala Leu Thr Arg Ser Met Asn Val Pro Thr Val
                565                 570                 575

Asn Leu Gly Met Ala Leu Gly Leu Pro Ala Val Val Asp Thr Trp Thr
                580                 585                 590

Lys Leu Gly Ala Pro Lys Asn Gln Leu Asn Ala Val Pro Ser Met Leu
                595                 600                 605

Leu Gly Ala Leu Asn Leu Thr Pro Ile Glu Val Ala Gln Ala Phe Gln
                610                 615                 620

Thr Ile Ala Ser Gly Gly Asn Arg Ala Pro Leu Ser Ala Leu Arg Ser
625                 630                 635                 640

Val Ile Ala Glu Asp Gly Thr Val Leu Tyr Gln Ser Tyr Pro Gln Ala
                645                 650                 655
```

-continued

```
Glu Arg Ala Val Pro Ala Gln Ala Ala Tyr Met Thr Leu Trp Thr Met
            660                 665                 670

Gln Gln Val Val Gln Arg Gly Thr Gly Arg Gln Leu Gly Ala Lys Tyr
        675                 680                 685

Pro Gly Leu His Leu Ala Gly Lys Thr Gly Thr Thr Asn Asn Asn Val
    690                 695                 700

Asp Thr Trp Phe Ala Gly Ile Asp Gly Ser Gln Val Thr Ile Thr Trp
705                 710                 715                 720

Val Gly Arg Asp Asn Asn Gln Pro Thr Lys Leu Tyr Gly Ala Ser Gly
                725                 730                 735

Ala Met Ser Ile Tyr Gln Arg Tyr Leu Ala Asn Gln Thr Pro Thr Pro
            740                 745                 750

Leu Val Leu Thr Val Pro Glu Asp Val Val Asp Met Gly Val Asp Ser
        755                 760                 765

Asn Gly Asn Phe Val Cys Ser Gly Gly Met Arg Ser Leu Pro Val Trp
    770                 775                 780

Thr Thr Gln Pro Asp Ala Leu Cys Arg Gln Gly Glu Met Met Gln Gln
785                 790                 795                 800

Gln Gln Leu Gln Gln Gln Glu Ala Lys Asn Pro Phe Asn Gln Ser Gly
                805                 810                 815

Gln Gln Pro Pro Pro Gln Gln Gln Gln Gln Gln Pro Pro Lys Gln
            820                 825                 830

Gln Glu Lys Ser Asp Gly Val Ala Gly Trp Ile Lys Asp Met Phe Gly
        835                 840                 845

Ser Asn
    850

<210> SEQ ID NO 7
<211> LENGTH: 798
<212> TYPE: PRT
<213> ORGANISM: Neisseria gonorrhoeae
<220> FEATURE:
<221> NAME/KEY: TRANSMEM
<222> LOCATION: (19)..(24)
<220> FEATURE:
<221> NAME/KEY: DOMAIN
<222> LOCATION: (52)..(263)
<220> FEATURE:
<221> NAME/KEY: DOMAIN
<222> LOCATION: (295)..(745)

<400> SEQUENCE: 7

Met Ile Lys Lys Ile Leu Thr Thr Cys Phe Gly Leu Phe Phe Gly Phe
1               5                   10                  15

Cys Val Phe Gly Val Gly Leu Val Ala Ile Ala Ile Leu Val Thr Tyr
            20                  25                  30

Pro Lys Leu Pro Ser Leu Asp Ser Leu Gln His Tyr Gln Pro Lys Met
        35                  40                  45

Pro Leu Thr Ile Tyr Ser Ala Asp Gly Glu Val Ile Gly Met Tyr Gly
    50                  55                  60

Glu Gln Arg Arg Glu Phe Thr Lys Ile Gly Asp Phe Pro Glu Val Leu
65                  70                  75                  80

Arg Asn Ala Val Ile Ala Ala Glu Asp Lys Arg Phe Tyr Arg His Trp
                85                  90                  95

Gly Val Asp Val Trp Gly Val Ala Arg Ala Ala Val Gly Asn Val Val
            100                 105                 110

Ser Gly Ser Val Gln Ser Gly Ala Ser Thr Ile Thr Gln Gln Val Ala
```

```
             115                 120                 125
Lys Asn Phe Tyr Leu Ser Ser Glu Lys Thr Phe Thr Arg Lys Phe Asn
             130                 135                 140

Glu Val Leu Leu Ala Tyr Lys Ile Glu Gln Ser Leu Ser Lys Asp Lys
145                 150                 155                 160

Ile Leu Glu Leu Tyr Phe Asn Gln Ile Tyr Leu Gly Gln Arg Ala Tyr
                165                 170                 175

Gly Phe Ala Ser Ala Ala Gln Ile Tyr Phe Asn Lys Asn Val Arg Asp
                180                 185                 190

Leu Thr Leu Ala Glu Ala Ala Met Leu Ala Gly Leu Pro Lys Ala Pro
                195                 200                 205

Ser Ala Tyr Asn Pro Ile Val Asn Pro Glu Arg Ala Lys Leu Arg Gln
            210                 215                 220

Lys Tyr Ile Leu Asn Asn Met Leu Glu Gly Lys Met Ile Thr Val Gln
225                 230                 235                 240

Gln Arg Asp Gln Ala Leu Asn Glu Glu Leu His Tyr Glu Arg Phe Val
                    245                 250                 255

Arg Lys Ile Asp Gln Ser Ala Leu Tyr Val Ala Glu Met Val Arg Arg
                260                 265                 270

Glu Leu Tyr Glu Lys Tyr Gly Glu Asp Ala Tyr Thr Gln Gly Phe Lys
            275                 280                 285

Val Tyr Thr Thr Val Arg Thr Asp His Gln Lys Ala Ala Thr Glu Ala
290                 295                 300

Leu Arg Lys Ala Leu Arg Asn Phe Asp Arg Gly Ser Ser Tyr Arg Gly
305                 310                 315                 320

Ala Glu Asn Tyr Ile Asp Leu Ser Lys Ser Glu Asp Val Glu Glu Thr
                325                 330                 335

Val Ser Gln Tyr Leu Ser Gly Leu Tyr Thr Val Asp Lys Met Val Pro
                340                 345                 350

Ala Val Val Leu Asp Val Thr Lys Lys Asn Val Val Ile Gln Leu
                355                 360                 365

Pro Gly Gly Arg Arg Val Ala Leu Asp Arg Arg Ala Leu Gly Phe Ala
    370                 375                 380

Ala Arg Ala Val Asp Asn Glu Lys Met Gly Glu Asp Arg Ile Arg Arg
385                 390                 395                 400

Gly Ala Val Ile Arg Val Lys Asn Asn Gly Arg Trp Ala Val Val
                405                 410                 415

Gln Glu Pro Leu Leu Gln Gly Ala Leu Val Ser Leu Asp Ala Lys Thr
                420                 425                 430

Gly Ala Val Arg Ala Leu Val Gly Gly Tyr Asp Phe His Ser Lys Thr
                435                 440                 445

Phe Asn Arg Ala Val Gln Ala Met Arg Gln Pro Gly Ser Thr Phe Lys
    450                 455                 460

Pro Phe Val Tyr Ser Ala Ala Leu Ser Lys Gly Met Thr Ala Ser Thr
465                 470                 475                 480

Val Val Asn Asp Ala Pro Ile Ser Leu Pro Gly Lys Gly Pro Asn Gly
                    485                 490                 495

Ser Val Trp Thr Pro Lys Asn Ser Asp Gly Arg Tyr Ser Gly Tyr Ile
                500                 505                 510

Thr Leu Arg Gln Ala Leu Thr Ala Ser Lys Asn Met Val Ser Ile Arg
        515                 520                 525

Ile Leu Met Ser Ile Gly Val Gly Tyr Ala Gln Gln Tyr Ile Arg Arg
        530                 535                 540
```

```
Phe Gly Phe Arg Pro Ser Glu Leu Pro Ala Ser Leu Ser Met Ala Leu
545                 550                 555                 560

Gly Thr Gly Glu Thr Thr Pro Leu Lys Val Ala Glu Ala Tyr Ser Val
            565                 570                 575

Phe Ala Asn Gly Gly Tyr Arg Val Ser Ser His Val Ile Asp Lys Ile
        580                 585                 590

Tyr Asp Arg Asp Gly Arg Leu Arg Ala Gln Met Gln Pro Leu Val Ala
    595                 600                 605

Gly Gln Asn Ala Pro Gln Ala Ile Asp Pro Arg Asn Ala Tyr Ile Met
610                 615                 620

Tyr Lys Ile Met Gln Asp Val Val Arg Val Gly Thr Ala Arg Gly Ala
625                 630                 635                 640

Ala Ala Leu Gly Arg Thr Asp Ile Ala Gly Lys Thr Gly Thr Thr Asn
                645                 650                 655

Asp Asn Lys Asp Ala Trp Phe Val Gly Phe Asn Pro Asp Val Val Thr
            660                 665                 670

Ala Val Tyr Ile Gly Phe Asp Lys Pro Lys Ser Met Gly Arg Ala Gly
        675                 680                 685

Tyr Gly Gly Thr Ile Ala Val Pro Val Trp Val Asp Tyr Met Arg Phe
    690                 695                 700

Ala Leu Lys Gly Lys Gln Gly Lys Gly Met Lys Met Pro Glu Gly Val
705                 710                 715                 720

Val Ser Ser Asn Gly Glu Tyr Tyr Met Lys Glu Arg Met Val Thr Asp
                725                 730                 735

Pro Gly Leu Met Leu Asp Asn Ser Gly Ile Ala Pro Gln Pro Ser Arg
            740                 745                 750

Arg Ala Lys Glu Asp Asp Glu Ala Ala Val Glu Asn Glu Gln Gln Gly
        755                 760                 765

Arg Ser Asp Glu Thr Arg Gln Asp Val Gln Glu Thr Pro Val Leu Pro
    770                 775                 780

Ser Asn Thr Asp Ser Lys Gln Gln Gln Leu Asp Ser Leu Phe
785                 790                 795

<210> SEQ ID NO 8
<211> LENGTH: 774
<212> TYPE: PRT
<213> ORGANISM: Pseudomonas aeruginosa
<220> FEATURE:
<221> NAME/KEY: TRANSMEM
<222> LOCATION: (22)..(45)
<220> FEATURE:
<221> NAME/KEY: DOMAIN
<222> LOCATION: (151)..(367)
<220> FEATURE:
<221> NAME/KEY: DOMAIN
<222> LOCATION: (402)..(701)

<400> SEQUENCE: 8

Met Thr Arg Pro Arg Ser Pro Ser Arg Asn Ser Lys Ala Arg Pro
1               5                   10                  15

Ala Pro Gly Leu Asn Lys Trp Leu Ser Trp Ala Leu Lys Leu Gly Leu
                20                  25                  30

Val Gly Leu Val Leu Leu Ala Gly Phe Ala Ile Tyr Leu Asp Ala Val
            35                  40                  45

Val Gln Glu Lys Phe Ser Gly Arg Arg Trp Thr Ile Pro Ala Lys Val
        50                  55                  60

Tyr Ala Arg Pro Leu Glu Leu Phe Asn Gly Leu Lys Leu Ser Arg Glu
```

```
                65                  70                  75                  80
Asp Phe Leu Arg Glu Leu Asp Ala Leu Gly Tyr Arg Arg Glu Pro Ser
                    85                  90                  95
Val Ser Gly Pro Gly Thr Val Ser Val Ala Ser Ala Val Glu Leu
                100                 105                 110
Asn Thr Arg Gly Phe Gln Phe Tyr Glu Gly Ala Glu Pro Ala Gln Arg
                115                 120                 125
Val Arg Val Arg Phe Asn Gly Asn Tyr Val Ser Gly Leu Ser Gln Ala
130                 135                 140
Asn Gly Lys Glu Leu Ala Val Ala Arg Leu Glu Pro Leu Leu Ile Gly
145                 150                 155                 160
Gly Leu Tyr Pro Ala His His Glu Asp Arg Ile Leu Val Lys Leu Asp
                165                 170                 175
Gln Val Pro Thr Tyr Leu Ile Asp Thr Leu Val Ala Val Glu Asp Arg
                180                 185                 190
Asp Phe Trp Asn His His Gly Val Ser Leu Lys Ser Val Ala Arg Ala
                195                 200                 205
Val Trp Val Asn Thr Thr Ala Gly Gln Leu Arg Gln Gly Gly Ser Thr
210                 215                 220
Leu Thr Gln Gln Leu Val Lys Asn Phe Phe Leu Ser Asn Glu Arg Ser
225                 230                 235                 240
Leu Ser Arg Lys Ile Asn Glu Ala Met Met Ala Val Leu Leu Glu Leu
                245                 250                 255
His Tyr Asp Lys Arg Asp Ile Leu Glu Ser Tyr Leu Asn Glu Val Phe
                260                 265                 270
Leu Gly Gln Asp Gly Gln Arg Ala Ile His Gly Phe Gly Leu Ala Ser
                275                 280                 285
Gln Tyr Phe Phe Ser Gln Pro Leu Ala Glu Leu Lys Leu Asp Gln Val
                290                 295                 300
Ala Leu Leu Val Gly Met Val Lys Gly Pro Ser Tyr Phe Asn Pro Arg
305                 310                 315                 320
Arg Tyr Pro Asp Arg Ala Leu Ala Arg Arg Asn Leu Val Leu Asp Val
                325                 330                 335
Leu Ala Glu Gln Gly Val Ala Thr Gln Gln Glu Val Asp Ala Ala Lys
                340                 345                 350
Leu Arg Pro Leu Gly Val Thr Arg Gln Gly Ser Met Ala Asp Ser Ser
                355                 360                 365
Tyr Pro Ala Phe Leu Asp Leu Val Lys Arg Gln Leu Arg Gln Asp Tyr
                370                 375                 380
Arg Asp Glu Asp Leu Thr Glu Glu Gly Leu Arg Ile Phe Thr Ser Phe
385                 390                 395                 400
Asp Pro Ile Leu Gln Glu Lys Ala Glu Thr Ser Val Asn Glu Thr Leu
                405                 410                 415
Lys Arg Leu Ser Gly Arg Lys Gly Val Asp Gln Val Glu Ala Ala Met
                420                 425                 430
Val Val Thr Asn Pro Glu Thr Gly Glu Ile Gln Ala Leu Ile Gly Ser
            435                 440                 445
Arg Asp Pro Arg Phe Ala Gly Phe Asn Arg Ala Leu Asp Ala Val Arg
450                 455                 460
Pro Ile Gly Ser Leu Ile Lys Pro Ala Val Tyr Leu Thr Ala Leu Glu
465                 470                 475                 480
Arg Pro Ser Lys Tyr Thr Leu Thr Trp Val Gln Asp Glu Pro Phe
                485                 490                 495
```

Ala Val Lys Gly Gln Asp Gly Gln Val Trp Arg Pro Gln Asn Tyr Asp
            500                 505                 510

Arg Arg Ser His Gly Thr Ile Phe Leu Tyr Gln Gly Leu Ala Asn Ser
            515                 520                 525

Tyr Asn Leu Ser Thr Ala Lys Leu Gly Leu Asp Val Gly Val Pro Asn
            530                 535                 540

Val Leu Gln Thr Val Ala Arg Leu Gly Ile Asn Arg Asp Trp Pro Ala
545                 550                 555                 560

Tyr Pro Ser Met Leu Leu Gly Ala Gly Ser Leu Ser Pro Met Glu Val
            565                 570                 575

Ala Thr Met Tyr Gln Thr Ile Ala Ser Gly Gly Phe Asn Thr Pro Leu
            580                 585                 590

Arg Gly Ile Arg Ser Val Leu Thr Ala Asp Gly Gln Pro Leu Lys Arg
            595                 600                 605

Tyr Pro Phe Gln Val Glu Gln Arg Phe Asp Ser Gly Ala Val Tyr Leu
            610                 615                 620

Val Gln Asn Ala Met Gln Arg Val Met Arg Glu Gly Thr Gly Arg Ser
625                 630                 635                 640

Val Tyr Ser Gln Leu Pro Ser Ser Leu Thr Leu Ala Gly Lys Thr Gly
            645                 650                 655

Thr Ser Asn Asp Ser Arg Asp Ser Trp Phe Ser Gly Phe Gly Gly Asp
            660                 665                 670

Leu Gln Ala Val Val Trp Leu Gly Arg Asp Asp Asn Gly Lys Thr Pro
            675                 680                 685

Leu Thr Gly Ala Thr Gly Ala Leu Gln Val Trp Ala Ser Phe Met Arg
            690                 695                 700

Lys Ala His Pro Gln Ser Leu Glu Met Pro Met Pro Glu Asn Val Val
705                 710                 715                 720

Met Ala Trp Val Asp Ala Gln Thr Gly Gln Gly Ser Ala Ala Asp Cys
            725                 730                 735

Pro Asn Ala Val Gln Met Pro Tyr Ile Arg Gly Ser Glu Pro Ala Gln
            740                 745                 750

Gly Pro Gly Cys Gly Ser Gln Asn Pro Ala Gly Glu Val Met Asp Trp
            755                 760                 765

Val Arg Gly Trp Leu Asn
            770

<210> SEQ ID NO 9
<211> LENGTH: 840
<212> TYPE: PRT
<213> ORGANISM: Salmonella enterica
<220> FEATURE:
<221> NAME/KEY: TRANSMEM
<222> LOCATION: (59)..(82)
<220> FEATURE:
<221> NAME/KEY: DOMAIN
<222> LOCATION: (189)..(402)
<220> FEATURE:
<221> NAME/KEY: DOMAIN
<222> LOCATION: (439)..(730)

<400> SEQUENCE: 9

Met Ala Gly Asn Asp Arg Glu Pro Ile Gly Arg Lys Gly Lys Ser Ser
1               5                   10                  15

Arg Pro Val Lys Gln Lys Val Ser Arg Arg Gln His Asp Asp Asp
            20                  25                  30

Tyr Asp Asp Asp Tyr Glu Asp Glu Glu Pro Met Pro Arg Lys Gly Lys

```
                35                  40                  45
Gly Lys Gly Arg Lys Pro Arg Gly Lys Arg Gly Trp Leu Trp Leu Leu
 50                  55                  60
Leu Lys Leu Phe Ile Val Phe Val Val Leu Phe Ala Ile Tyr Gly Val
 65                  70                  75                  80
Tyr Leu Asp Gln Lys Ile Arg Ser Arg Ile Asp Gly Lys Val Trp Gln
                 85                  90                  95
Leu Pro Ala Ala Val Tyr Gly Arg Met Val Asn Leu Glu Pro Asp Met
            100                 105                 110
Pro Val Ser Lys Asn Glu Met Val Lys Leu Glu Ala Thr Gln Tyr
            115                 120                 125
Arg Leu Val Thr Lys Met Thr Arg Pro Gly Glu Phe Thr Val Gln Ala
130                 135                 140
Asn Ser Ile Glu Met Ile Arg Arg Pro Phe Asp Phe Pro Asp Ser Lys
145                 150                 155                 160
Glu Gly Gln Val Arg Ala Arg Leu Thr Phe Ser Asp Gly Arg Leu Glu
                165                 170                 175
Thr Ile Val Asn Leu Asp Asn Asn Arg Gln Phe Gly Phe Phe Arg Leu
            180                 185                 190
Asp Pro Arg Leu Ile Thr Met Leu Ser Ser Pro Asn Gly Glu Gln Arg
            195                 200                 205
Leu Phe Val Pro Arg Ser Gly Phe Leu Asp Leu Leu Val Asp Thr Leu
210                 215                 220
Leu Ala Thr Glu Asp Arg His Phe Tyr Glu His Asp Gly Ile Ser Leu
225                 230                 235                 240
Tyr Ser Ile Gly Arg Ala Val Leu Ala Asn Leu Thr Ala Gly Arg Thr
                245                 250                 255
Val Gln Gly Ala Ser Thr Leu Thr Gln Gln Leu Val Lys Asn Leu Phe
            260                 265                 270
Leu Ser Ser Glu Arg Ser Tyr Trp Arg Lys Ala Asn Glu Ala Tyr Met
            275                 280                 285
Ala Leu Ile Met Asp Ala Arg Tyr Ser Lys Asp Arg Ile Leu Glu Leu
290                 295                 300
Tyr Met Asn Glu Val Tyr Leu Gly Gln Ser Gly Asp Asn Glu Ile Arg
305                 310                 315                 320
Gly Phe Pro Leu Ala Ser Leu Tyr Tyr Phe Gly Arg Pro Val Glu Glu
                325                 330                 335
Leu Ser Leu Asp Gln Gln Ala Leu Leu Val Gly Met Val Lys Gly Ala
            340                 345                 350
Ser Ile Tyr Asn Pro Trp Arg Asn Pro Lys Leu Ala Leu Glu Arg Arg
            355                 360                 365
Asn Leu Val Leu Arg Leu Leu Gln Gln Gln Lys Ile Ile Asp Gln Glu
            370                 375                 380
Leu Tyr Asp Met Leu Ser Ala Arg Pro Leu Gly Val Gln Pro Arg Gly
385                 390                 395                 400
Gly Val Ile Ser Pro Gln Pro Ala Phe Met Gln Met Val Arg Gln Glu
                405                 410                 415
Leu Gln Ala Lys Leu Gly Asp Lys Ile Lys Asp Leu Ser Gly Val Lys
            420                 425                 430
Ile Phe Thr Thr Phe Asp Ser Val Ala Gln Asp Ala Val Glu Lys Ala
            435                 440                 445
Val Val Glu Gly Ile Pro Ala Leu Lys Lys Gln Arg Lys Leu Ser Asp
450                 455                 460
```

Leu Glu Thr Ala Met Val Val Asp Arg Phe Ser Gly Glu Val Arg
465                 470                 475                 480

Ala Met Val Gly Gly Ala Glu Pro Gln Tyr Ala Gly Tyr Asn Arg Ala
            485                 490                 495

Met Gln Ala Arg Arg Ser Ile Gly Ser Leu Ala Lys Pro Ala Thr Tyr
        500                 505                 510

Leu Thr Ala Leu Ser Gln Pro Asn Leu Tyr Arg Leu Asn Thr Trp Ile
        515                 520                 525

Ala Asp Ala Pro Ile Ser Leu Arg Gln Pro Asn Gly Gln Val Trp Ser
530                 535                 540

Pro Gln Asn Asp Asp Arg Arg Tyr Ser Glu Ser Gly Lys Val Met Leu
545                 550                 555                 560

Val Asp Ala Leu Thr Arg Ser Met Asn Val Pro Thr Val Asn Leu Gly
                565                 570                 575

Met Ala Leu Gly Leu Pro Ala Val Thr Asp Thr Trp Thr Lys Leu Gly
            580                 585                 590

Val Pro Lys Asp Gln Leu Asn Pro Val Pro Ala Met Leu Leu Gly Ala
        595                 600                 605

Leu Asn Leu Thr Pro Ile Glu Val Ala Gln Ala Phe Gln Thr Ile Ala
        610                 615                 620

Ser Gly Gly Asn Arg Ala Pro Leu Ser Ala Leu Arg Ser Val Ile Ala
625                 630                 635                 640

Glu Asp Gly Lys Val Leu Tyr Gln Ser Tyr Pro Gln Ala Glu Arg Ala
                645                 650                 655

Val Pro Ala Gln Ala Ala Tyr Leu Thr Leu Trp Thr Met Gln Gln Val
            660                 665                 670

Val Gln Arg Gly Thr Gly Arg Gln Leu Gly Ala Lys Tyr Pro Gly Leu
        675                 680                 685

His Leu Ala Gly Lys Thr Gly Thr Thr Asn Asn Asn Val Asp Thr Trp
        690                 695                 700

Phe Ala Gly Ile Asp Gly Ser Gln Val Thr Ile Thr Trp Val Gly Arg
705                 710                 715                 720

Asp Asn Asn Gln Pro Thr Lys Leu Tyr Gly Ala Ser Gly Ala Met Ala
                725                 730                 735

Ile Tyr Gln Arg Tyr Leu Ala Asn Gln Thr Pro Thr Pro Leu Val Leu
            740                 745                 750

Thr Pro Pro Glu Asp Val Val Asp Met Gly Val Asp Tyr Asp Gly Asn
        755                 760                 765

Phe Val Cys Ser Gly Gly Met Arg Thr Leu Pro Val Trp Thr Asp Asp
        770                 775                 780

Pro Asn Thr Leu Cys Gln Gln Gly Glu Met Met Gln Gln Gln Gln
785                 790                 795                 800

Pro Ser Gly Asn Pro Phe Asp Gln Ser Ser Gln Pro Gln Pro Ala
                805                 810                 815

Gln Gln Gln Pro Pro Lys Glu Glu Lys Ser Asp Gly Val Ala Gly Trp
            820                 825                 830

Ile Lys Glu Met Phe Gly Gly Asn
        835                 840

<210> SEQ ID NO 10
<211> LENGTH: 844
<212> TYPE: PRT
<213> ORGANISM: Shigella flexneri
<220> FEATURE:

```
<221> NAME/KEY: TRANSMEM
<222> LOCATION: (64)..(87)
<220> FEATURE:
<221> NAME/KEY: DOMAIN
<222> LOCATION: (194)..(410)
<220> FEATURE:
<221> NAME/KEY: DOMAIN
<222> LOCATION: (444)..(792)

<400> SEQUENCE: 10

Met Ala Gly Asn Asp Arg Glu Pro Ile Gly Arg Lys Gly Lys Pro Thr
 1               5                  10                  15

Arg Pro Val Lys Gln Lys Val Ser Arg Arg Tyr Glu Asp Asp Asp Asp
             20                  25                  30

Asp Tyr Asp Asp Tyr Asp Asp Tyr Glu Asp Glu Pro Met Pro Arg
         35                  40                  45

Lys Gly Lys Gly Lys Gly Lys Gly Arg Lys Pro Arg Gly Lys Arg Gly
 50                  55                  60

Trp Leu Trp Leu Leu Lys Leu Ala Ile Val Phe Ala Val Leu Ile
 65                  70                  75                  80

Ala Ile Tyr Gly Val Tyr Leu Asp Gln Lys Ile Arg Ser Arg Ile Asp
                 85                  90                  95

Gly Lys Val Trp Gln Leu Pro Ala Ala Val Tyr Gly Arg Met Val Asn
            100                 105                 110

Leu Glu Pro Asp Met Thr Ile Ser Lys Asn Glu Met Val Lys Leu Leu
        115                 120                 125

Glu Ala Thr Gln Tyr Arg Gln Val Ser Lys Met Thr Arg Pro Gly Glu
    130                 135                 140

Phe Thr Val Gln Ala Asn Ser Ile Glu Met Ile Arg Arg Pro Phe Asp
145                 150                 155                 160

Phe Pro Asp Ser Lys Glu Gly Gln Val Arg Ala Arg Leu Thr Phe Asp
                165                 170                 175

Gly Asp His Leu Ala Thr Ile Val Asn Met Glu Asn Asn Arg Gln Phe
            180                 185                 190

Gly Phe Phe Arg Leu Asp Pro Arg Leu Ile Thr Met Ile Ser Ser Pro
        195                 200                 205

Asn Gly Glu Gln Arg Leu Phe Val Pro Arg Ser Gly Phe Pro Asp Leu
    210                 215                 220

Leu Val Asp Thr Leu Leu Ala Thr Glu Asp Arg His Phe Tyr Glu His
225                 230                 235                 240

Asp Gly Ile Ser Leu Tyr Ser Ile Gly Arg Ala Val Leu Ala Asn Leu
                245                 250                 255

Thr Ala Gly Arg Thr Val Gln Gly Ala Ser Thr Leu Thr Gln Gln Leu
            260                 265                 270

Val Lys Asn Leu Phe Leu Ser Ser Glu Arg Ser Tyr Trp Arg Lys Ala
        275                 280                 285

Asn Glu Ala Tyr Met Ala Leu Ile Met Asp Ala Arg Tyr Ser Lys Asp
    290                 295                 300

Arg Ile Leu Glu Leu Tyr Met Asn Glu Val Tyr Leu Gly Gln Ser Gly
305                 310                 315                 320

Asp Asn Glu Ile Arg Gly Phe Pro Leu Ala Ser Leu Tyr Tyr Phe Gly
                325                 330                 335

Arg Pro Val Glu Glu Leu Ser Leu Asp Gln Gln Ala Leu Leu Val Gly
            340                 345                 350

Met Val Lys Gly Ala Ser Ile Tyr Asn Pro Trp Arg Asn Pro Lys Leu
        355                 360                 365
```

```
Ala Leu Glu Arg Arg Asn Leu Val Leu Arg Leu Leu Gln Gln Gln Gln
    370                 375                 380

Ile Ile Asp Gln Glu Leu Tyr Asp Met Leu Ser Ala Arg Pro Leu Gly
385                 390                 395                 400

Val Gln Pro Arg Gly Gly Val Ile Ser Pro Gln Pro Ala Phe Met Gln
                405                 410                 415

Leu Val Arg Gln Glu Leu Gln Ala Lys Leu Gly Asp Lys Val Lys Asp
            420                 425                 430

Leu Ser Gly Val Lys Ile Phe Thr Thr Phe Asp Ser Val Ala Gln Asp
        435                 440                 445

Ala Ala Glu Lys Ala Ala Val Glu Gly Ile Pro Ala Leu Lys Lys Gln
    450                 455                 460

Arg Lys Leu Ser Asp Leu Glu Thr Ala Ile Val Val Asp Arg Phe
465                 470                 475                 480

Ser Gly Glu Val Arg Ala Met Val Gly Gly Ser Glu Pro Gln Phe Ala
                485                 490                 495

Gly Tyr Asn Arg Ala Met Gln Ala Arg Arg Ser Ile Gly Ser Leu Ala
            500                 505                 510

Lys Pro Ala Thr Tyr Leu Thr Ala Leu Ser Gln Pro Lys Ile Tyr Arg
        515                 520                 525

Leu Asn Thr Trp Ile Ala Asp Ala Pro Ile Ala Leu Arg Gln Pro Asn
    530                 535                 540

Gly Gln Val Trp Ser Pro Gln Asn Asp Asp Arg Arg Tyr Ser Glu Ser
545                 550                 555                 560

Gly Arg Val Met Leu Val Asp Ala Leu Thr Arg Ser Met Asn Val Pro
                565                 570                 575

Thr Val Asn Leu Gly Met Ala Leu Gly Leu Pro Ala Val Thr Glu Thr
            580                 585                 590

Trp Ile Lys Leu Gly Val Pro Lys Asp Gln Leu His Pro Val Pro Ala
        595                 600                 605

Met Leu Leu Gly Ala Leu Asn Leu Thr Pro Ile Glu Val Ala Gln Ala
    610                 615                 620

Phe Gln Thr Ile Ala Ser Gly Gly Asn Arg Ala Pro Leu Ser Ala Leu
625                 630                 635                 640

Arg Ser Val Ile Ala Glu Asp Gly Lys Val Leu Tyr Gln Ser Phe Pro
                645                 650                 655

Gln Ala Glu Arg Ala Val Pro Ala Gln Ala Tyr Leu Thr Leu Trp
            660                 665                 670

Thr Met Gln Gln Val Val Gln Arg Gly Thr Gly Arg Gln Leu Gly Ala
        675                 680                 685

Lys Tyr Pro Asn Leu His Leu Ala Gly Lys Thr Gly Thr Thr Asn Asn
    690                 695                 700

Asn Val Asp Thr Trp Phe Ala Gly Ile Asp Gly Ser Thr Val Thr Ile
705                 710                 715                 720

Thr Trp Val Gly Arg Asp Asn Asn Gln Pro Thr Lys Leu Tyr Gly Ala
                725                 730                 735

Ser Gly Ala Met Ser Ile Tyr Gln Arg Tyr Leu Ala Asn Gln Thr Pro
            740                 745                 750

Thr Pro Leu Asn Leu Val Pro Pro Glu Asp Ile Ala Asp Met Gly Val
        755                 760                 765

Asp Tyr Asp Gly Asn Phe Val Cys Ser Gly Gly Met Arg Val Leu Pro
    770                 775                 780
```

```
Val Trp Thr Ser Asp Pro Gln Ser Leu Cys Gln Gln Ser Glu Met Gln
785                 790                 795                 800

Gln Gln Pro Ser Gly Asn Pro Phe Asp Gln Ser Ser Gln Pro Gln Gln
            805                 810                 815

Gln Pro Gln Gln Gln Pro Ala Gln Gln Glu Gln Lys Asp Ser Asp Gly
        820                 825                 830

Val Ala Gly Trp Ile Lys Asp Met Phe Gly Ser Asn
        835                 840

<210> SEQ ID NO 11
<211> LENGTH: 914
<212> TYPE: PRT
<213> ORGANISM: Bacillus subtilis
<220> FEATURE:
<221> NAME/KEY: TRANSMEM
<222> LOCATION: (28)..(50)
<220> FEATURE:
<221> NAME/KEY: DOMAIN
<222> LOCATION: (79)..(293)
<220> FEATURE:
<221> NAME/KEY: DOMAIN
<222> LOCATION: (329)..(660)

<400> SEQUENCE: 11

Met Ser Asp Gln Phe Asn Ser Arg Glu Ala Arg Arg Lys Ala Asn Ser
1               5                   10                  15

Lys Ser Ser Pro Ser Pro Lys Lys Gly Lys Lys Arg Lys Lys Gly Gly
            20                  25                  30

Leu Phe Lys Lys Thr Leu Phe Thr Leu Leu Ile Leu Phe Val Leu Gly
        35                  40                  45

Val Val Gly Gly Ala Val Thr Phe Ala Val Met Val Ser Asp Ala Pro
50                  55                  60

Ser Leu Asp Glu Ser Lys Leu Lys Thr Pro Tyr Ser Ser Thr Ile Tyr
65                  70                  75                  80

Asp Lys Asn Gly Lys Glu Ile Ala Glu Val Gly Ala Glu Lys Arg Thr
                85                  90                  95

Tyr Val Ser Ile Asp Glu Ile Pro Asp Val Val Lys Glu Ala Phe Ile
            100                 105                 110

Ala Thr Glu Asp Ala Arg Phe Tyr Glu His His Gly Ile Asp Pro Val
        115                 120                 125

Arg Ile Gly Gly Ala Leu Val Ala Asn Phe Lys Asp Gly Phe Gly Ala
    130                 135                 140

Glu Gly Gly Ser Thr Ile Thr Gln Gln Val Val Lys Asn Ser Leu Leu
145                 150                 155                 160

Ser His Gln Lys Thr Leu Lys Arg Lys Val Gln Glu Val Trp Leu Ser
                165                 170                 175

Ile Gln Leu Glu Arg Asn Tyr Ser Lys Asp Glu Ile Leu Glu Met Tyr
            180                 185                 190

Leu Asn Arg Ile Tyr Phe Ser Pro Arg Ala Tyr Gly Ile Gly Lys Ala
        195                 200                 205

Ala Glu Glu Phe Phe Gly Val Thr Asp Leu Ser Lys Leu Thr Val Glu
    210                 215                 220

Gln Ala Ala Thr Leu Ala Gly Met Pro Gln Ser Pro Thr Ala Tyr Asn
225                 230                 235                 240

Pro Val Lys Asn Pro Asp Lys Ala Glu Lys Arg Arg Asn Ile Val Leu
                245                 250                 255

Ser Leu Met Lys Lys Gln Gly Phe Ile Ser Asp Ser Gln Tyr Asn Lys
            260                 265                 270
```

```
Ala Lys Lys Val Ala Lys Asp Glu Gly Val Val Ser Gln Lys Glu
        275                 280                 285

Tyr Glu Lys Ala Ser Thr Asn Lys Tyr Ser Ala Phe Val Glu Val
    290                 295                 300

Met Lys Glu Ile Asp Glu Lys Ser Asp Val Asp Pro Ser Ala Asp Gly
305                 310                 315                 320

Leu Lys Ile Tyr Thr Thr Leu Asp Thr Lys Ala Gln Asp Lys Leu Asp
                325                 330                 335

Glu Leu Met Asp Gly Asp Thr Val Gly Phe Thr Glu Gly Met Gln Gly
            340                 345                 350

Gly Val Thr Leu Leu Asp Thr Lys Asn Gly Glu Val Arg Ala Ile Gly
        355                 360                 365

Ala Gly Arg Asn Gln Pro Val Gly Gly Phe Asn Tyr Ala Thr Gln Thr
    370                 375                 380

Lys Ala Gln Pro Gly Ser Thr Ile Lys Pro Ile Leu Asp Tyr Gly Pro
385                 390                 395                 400

Val Ile Glu Asn Lys Lys Trp Ser Thr Tyr Glu Gln Ile Asp Asp Ser
                405                 410                 415

Ala Tyr Thr Tyr Ser Asn Gly Lys Pro Ile Arg Asp Trp Asp Arg Lys
            420                 425                 430

Tyr Leu Gly Pro Ile Ser Met Arg Tyr Ala Leu Ala Gln Ser Arg Asn
        435                 440                 445

Ile Pro Ala Leu Lys Ala Phe Gln Ala Val Gly Lys Asp Thr Ala Val
    450                 455                 460

Asp Phe Ala Asn Gly Leu Gly Leu Gly Leu Thr Lys Asp Asn Val Thr
465                 470                 475                 480

Glu Ala Tyr Ser Ile Gly Gly Phe Gly Gly Asn Asp Gly Val Ser Pro
                485                 490                 495

Leu Thr Met Ala Gly Ala Tyr Ser Ala Phe Gly Asn Asn Gly Thr Tyr
            500                 505                 510

Asn Glu Pro His Phe Val Lys Ser Ile Glu Phe Asn Asp Gly Thr Lys
        515                 520                 525

Leu Asp Leu Thr Pro Lys Ser Lys Ser Ala Met Ser Asp Tyr Thr Ala
    530                 535                 540

Phe Met Ile Thr Asp Met Leu Lys Thr Ala Val Lys Thr Gly Thr Gly
545                 550                 555                 560

Gln Leu Ala Gln Val Pro Gly Val Glu Val Ala Gly Lys Thr Gly Thr
                565                 570                 575

Thr Asn Phe Asp Asp Asn Glu Val Lys Arg Tyr Asn Ile Ala Ser Gly
            580                 585                 590

Gly Ala Arg Asp Ser Trp Phe Val Gly Tyr Thr Pro Gln Tyr Thr Ala
        595                 600                 605

Ala Val Trp Thr Gly Met Gly Glu Asn Glu Ala Gly Lys Lys Ser Leu
    610                 615                 620

Ser Ala Glu Glu Gln Lys Val Ala Lys Arg Ile Phe Ala Gln Leu Ile
625                 630                 635                 640

Ala Asp Val Asp Asp Gly Ser Gly Ser Phe Glu Lys Pro Asp Ser Val
                645                 650                 655

Val Glu Ala Thr Val Glu Lys Gly Ser Asn Pro Ala Lys Leu Ala Gly
            660                 665                 670

Pro Asn Thr Pro Ser Asp Lys Lys Leu Thr Glu Tyr Phe Val Lys Gly
        675                 680                 685
```

-continued

```
Thr Ala Pro Ser Thr Val Ser Lys Thr Tyr Glu Lys Glu Lys Glu
            690                 695                 700

Glu Thr Ala Lys Leu Ser Gly Leu Asn Val Lys Tyr Asp Lys Asp Asn
705                 710                 715                 720

Gln Ser Leu Thr Leu Ser Trp Asn Tyr Asp Gly Asp Ala Thr Phe Ala
                725                 730                 735

Val Lys Gln Ser Val Asp Gly Gly Ser Tyr Ser Glu Ile Gln Asn Ser
            740                 745                 750

Ser Ala Lys Glu Ala Val Ile Ser Gly Val Gln Pro Gly Ser Val Tyr
        755                 760                 765

Lys Phe Glu Val Thr Ala Val Ser Asp Asp Gly Lys Ser Thr Ala Ser
770                 775                 780

Thr Ser Tyr Glu Val Pro Lys Ala Glu Asp Glu Asp Lys Lys Asp
785                 790                 795                 800

Gln Gln Gln Thr Asp Asp Glu Lys Gln Asp Glu Lys Thr Gln Asp
                805                 810                 815

Asp Thr Gln Thr Asp Asp Ser Gln Lys Asp Asp Gly Gln Thr Asp Gln
            820                 825                 830

Asp Gln Thr Asp Asp Ser Thr Asn Asp Gln Lys Lys Gln Asp Asn
                835                 840                 845

Thr Asn Thr Asn Pro Ser Asp Asn Asn Gln Asp Gln Ser Asn Asp
850                 855                 860

Asn Asp Asn Asp Asn Ser Asn Gln Asp Thr Ser Asp Gly Asp Ser
865                 870                 875                 880

Asn Ser Gly Lys Asn Asp Ser Thr Gly Ser Asp Thr Asn Lys Asn Lys
                885                 890                 895

Thr Asp Thr Ser Asn Lys Thr Gln Thr Asn Ser Ser Ser Ile Glu Lys
            900                 905                 910

Thr Asn
```

```
<210> SEQ ID NO 12
<211> LENGTH: 897
<212> TYPE: PRT
<213> ORGANISM: Clostridium difficile
<220> FEATURE:
<221> NAME/KEY: TRANSMEM
<222> LOCATION: (47)..(71)
<220> FEATURE:
<221> NAME/KEY: DOMAIN
<222> LOCATION: (100)..(373)
<220> FEATURE:
<221> NAME/KEY: DOMAIN
<222> LOCATION: (418)..(731)

<400> SEQUENCE: 12
```

```
Met Asn Asn Asp Asn Asp Lys Asn Gly Asn Lys Ile Arg Arg Lys Lys
1               5                   10                  15

Val Ser Ser Ser Gly Asn Thr Asn Lys Pro Ile Asn Arg Thr Ser Ala
            20                  25                  30

Asn Lys Thr Arg Ser Thr Lys Asn Lys Lys Ser Lys Ser Asp
        35                  40                  45

Lys Phe Lys Lys Leu Arg Val Phe Gly Ile Val Phe Leu Val Leu Leu
50                  55                  60

Val Val Gly Thr Ala Gly Thr Ala Gly Leu Val Phe Ala Ser Leu Arg
65                  70                  75                  80

Asp Val Thr Pro Val Thr Glu Ala Val Leu Asp Lys Gln Thr Asn Gln
                85                  90                  95
```

```
Thr Thr Thr Ile Lys Tyr Ala Asn Gly Lys Thr Leu Ser Thr Ala Pro
            100                 105                 110

Ser Val Asn Lys Lys Thr Pro Val Pro Leu Asp Lys Ile Ser Pro Tyr
        115                 120                 125

Leu Gln His Ala Val Ile Ala Ile Glu Asp Glu Arg Phe Tyr Glu His
    130                 135                 140

Lys Gly Val Asp Ile Lys Gly Leu Phe Arg Ser Val Leu Lys Thr Leu
145                 150                 155                 160

Thr Gly Thr Lys Gln Gly Gly Ser Thr Ile Pro Met Gln Val Ser Lys
                165                 170                 175

Met Leu Leu Thr Thr Glu Gln Gln Thr Ile Pro Arg Lys Ile Lys Asp
            180                 185                 190

Ile Tyr Tyr Ala His Glu Met Ser Lys Thr Val Ser Lys Asp Lys Ile
        195                 200                 205

Leu Glu Thr Tyr Leu Asn Asn Phe Phe Val Gly Arg Gly Leu Ala Gly
    210                 215                 220

Ala Glu Ala Gly Ala Arg Gly Tyr Phe Asp Lys Ser Ala Ala Asp Leu
225                 230                 235                 240

Thr Leu Ala Glu Ser Ala Leu Leu Ala Gly Ser Thr Lys Asn Pro Ser
                245                 250                 255

Arg Phe Ser Ala Tyr Lys Thr Ser Lys Leu Glu Gly Asn Glu Thr Lys
            260                 265                 270

Glu Asp Leu Glu Asn Lys Leu Leu Phe Phe Val Asn Thr Asp Asp
        275                 280                 285

Asp Leu Asp Asp Pro Thr Gln Val Asp Phe Asp Met Ile Glu Lys Ile
    290                 295                 300

Lys Ser Trp Glu Leu Ile Ser Asn Asp Thr Tyr Arg Gln Leu Lys Ala
305                 310                 315                 320

Gly Thr Leu Val Val Arg Lys Ala Val Ser Asn Pro Glu Ala Lys Lys
                325                 330                 335

Arg Gln Glu Ile Val Leu Lys Lys Met Leu Glu Leu Lys Tyr Ile Lys
            340                 345                 350

Gln Ser Glu Tyr Asp Glu Ala Ile Lys Ala Lys Ile Glu Ile Lys Leu
        355                 360                 365

Pro Gln Ser Ser Asp Lys Val Ser Ser Val Glu Asp Leu Ile Glu
    370                 375                 380

Ser Glu Val Ile Asn Ala Leu Met Glu Gln Gly His Thr Asn Asp Glu
385                 390                 395                 400

Ala Gln Asn Leu Phe Tyr Asn Gly Gly Leu Ile Val Asn Thr Thr Ile
                405                 410                 415

Asp Pro Lys Met Gln Asp Ala Leu Glu Glu Phe Asp Arg Asn Ser
            420                 425                 430

Asn Phe Pro Gly His Met Val Gly Pro Asp Gly Val Ser Gln Pro Gln
        435                 440                 445

Ala Ala Met Val Ile Leu Asp Tyr Lys Asn Gly Glu Ile Arg Ala Leu
    450                 455                 460

Ala Gly Gly Arg Asn Ile Ser Gly Arg Lys Thr Leu Asn Arg Ala Thr
465                 470                 475                 480

Asn Pro His Gln Pro Gly Ser Ser Ile Lys Pro Leu Ala Ile Tyr Thr
                485                 490                 495

Pro Ala Ile Asp Thr Leu Lys Ile Thr Gln Ala Thr Ala Leu Ser Asp
            500                 505                 510

Ser Arg Gly Gly Tyr Lys Phe Glu Glu Asn Asn Lys Trp Asn Pro Arg
```

```
                515                 520                 525
Thr Thr Thr Ala Gly His Gly Ser Met Ser Leu Arg Lys Ala Leu Ala
        530                 535                 540
Lys Ser Ser Asn Thr Ile Ala Val Lys Thr Ala Glu Met Leu Gly Asp
545                 550                 555                 560
Ser Tyr Asp Glu Cys Val Asp Ile Met Met Asp Tyr Leu Lys Asn Phe
                565                 570                 575
Gly Ile Thr Thr Leu Lys Asn Asn His Ser Gly Ser Ser Glu Ala Ser
            580                 585                 590
Asp Arg Lys Phe Pro Ser Leu Thr Leu Gly Gly Met Ala Asn Gly Ile
            595                 600                 605
Thr Pro Leu Gln Met Ala Ala Ala Tyr Gly Thr Leu Ala Asn His Gly
        610                 615                 620
Ile Tyr Val Glu Pro Ser Ile Phe Thr Thr Ile Thr Thr Phe Asp Gly
625                 630                 635                 640
Gln Leu Leu Val Lys Asn Ala Pro Glu Glu His Lys Val Val Asp Pro
                645                 650                 655
Glu Val Ala Tyr Val Val Thr Asp Met Leu Glu Ser Val Ile Thr Glu
            660                 665                 670
Gly Ile Gly Gly Val Ala Thr Leu Pro Lys Gly Met Pro Val Ala Gly
        675                 680                 685
Lys Thr Gly Thr Thr Asn Ser Ala Tyr Asp Ala Trp Phe Val Gly Tyr
    690                 695                 700
Thr Pro Tyr Tyr Val Gly Ala Thr Tyr Ile Gly Asp Asp Ala Gly Arg
705                 710                 715                 720
Lys Asp Asp Ser Gly Asn Thr Ile Lys Arg Arg Glu Val Pro His Gly
                725                 730                 735
Ser Thr Ser Thr Ala Lys Leu Trp Glu Lys Ile Met Glu Lys Ile His
            740                 745                 750
Ala Asn Leu Thr Val Thr Glu Phe Glu Val Pro Lys Asn Val Tyr Phe
        755                 760                 765
Thr Lys Ile Asn Leu Glu Asp Gly Gly Lys Gln Ser Ser Gly Ser Lys
    770                 775                 780
Ala Ala Phe Ile Glu Gly Thr Ala Pro Thr Lys Val Ser Ser Gln Pro
785                 790                 795                 800
Ser Ser Glu Asp Thr Lys Lys Pro Asp Asn Asn Gln Pro Glu Glu Asn
                805                 810                 815
Asn Asn Asn Asn Asn Thr Gly Asp Asn Gly Gly Ser Thr Pro
            820                 825                 830
Pro Asp Asn Gly Gly Asn Asn Gly Gly Ser Thr Thr Pro Pro Asp
        835                 840                 845
Asn Gly Gly Asn Asn Gly Gly Ser Thr Thr Pro Pro Asp Asn Gly
    850                 855                 860
Gly Asn Asn Gly Gly Gly Ser Thr Thr Pro Pro Asp Gly Gly Asn
865                 870                 875                 880
Asn Gly Gly Gly Ser Thr Thr Pro Pro Asp Gly Gly Thr Pro Ala
                885                 890                 895
Thr

<210> SEQ ID NO 13
<211> LENGTH: 781
<212> TYPE: PRT
<213> ORGANISM: Enterococcus faecalis
<220> FEATURE:
```

```
<221> NAME/KEY: TRANSMEM
<222> LOCATION: (15)..(45)
<220> FEATURE:
<221> NAME/KEY: DOMAIN
<222> LOCATION: (82)..(307)
<220> FEATURE:
<221> NAME/KEY: DOMAIN
<222> LOCATION: (364)..(666)

<400> SEQUENCE: 13
```

| Leu | Pro | Arg | Lys | Asn | Thr | Arg | Lys | Lys | Gln | Asn | Arg | Lys | Lys | Glu |
|---|---|---|---|---|---|---|---|---|---|---|---|---|---|---|
| 1 | | | | 5 | | | | | 10 | | | | | 15 |

| Lys | Trp | Phe | Val | Pro | Lys | Ile | Ile | Phe | Arg | Val | Phe | Gln | Ser | Leu | Thr |
|---|---|---|---|---|---|---|---|---|---|---|---|---|---|---|---|
| | | | 20 | | | | | 25 | | | | | 30 | | |

| Val | Phe | Ile | Thr | Val | Leu | Leu | Leu | Met | Phe | Ala | Ala | Leu | Gly | Ile | Gly |
|---|---|---|---|---|---|---|---|---|---|---|---|---|---|---|---|
| | | | 35 | | | | | 40 | | | | | 45 | | |

| Ile | Gly | Ala | Gly | Tyr | Phe | Ala | Tyr | Leu | Val | Glu | Asp | Thr | Gln | Leu | Pro |
|---|---|---|---|---|---|---|---|---|---|---|---|---|---|---|---|
| | 50 | | | | | 55 | | | | | 60 | | | | |

| Thr | Lys | Lys | Ala | Leu | Gln | Thr | Glu | Leu | Gly | Asn | Ile | Thr | Glu | Thr | Ser |
|---|---|---|---|---|---|---|---|---|---|---|---|---|---|---|---|
| 65 | | | | | 70 | | | | | 75 | | | | | 80 |

| Lys | Ile | Val | Tyr | Ala | Asp | Asn | Thr | Glu | Ile | Ser | Lys | Ile | Gln | Thr | Asp |
|---|---|---|---|---|---|---|---|---|---|---|---|---|---|---|---|
| | | | | 85 | | | | | 90 | | | | | 95 | |

| Leu | Met | Arg | Thr | Thr | Ile | Ser | Ser | Asp | Lys | Ile | Ser | Pro | Leu | Leu | Lys |
|---|---|---|---|---|---|---|---|---|---|---|---|---|---|---|---|
| | | | 100 | | | | | 105 | | | | | 110 | | |

| Thr | Ala | Ile | Ile | Ser | Thr | Glu | Asp | Glu | Tyr | Phe | Asp | Lys | His | Gln | Gly |
|---|---|---|---|---|---|---|---|---|---|---|---|---|---|---|---|
| | | | 115 | | | | | 120 | | | | | 125 | | |

| Tyr | Val | Pro | Lys | Ala | Val | Leu | Arg | Ala | Leu | Val | Ser | Glu | Ala | Thr | Gly |
|---|---|---|---|---|---|---|---|---|---|---|---|---|---|---|---|
| | 130 | | | | | 135 | | | | | 140 | | | | |

| Ile | Gly | Ser | Ser | Gly | Gly | Ser | Thr | Leu | Thr | Gln | Gln | Leu | Val | Lys | Gln |
|---|---|---|---|---|---|---|---|---|---|---|---|---|---|---|---|
| 145 | | | | | 150 | | | | | 155 | | | | | 160 |

| Gln | Ile | Leu | Thr | Asp | Glu | Thr | Thr | Phe | Lys | Arg | Lys | Ala | Asn | Glu | Ile |
|---|---|---|---|---|---|---|---|---|---|---|---|---|---|---|---|
| | | | | 165 | | | | | 170 | | | | | 175 | |

| Ile | Leu | Ser | Ala | Gln | Val | Glu | Lys | Tyr | Phe | Ser | Lys | Asp | Glu | Ile | Ile |
|---|---|---|---|---|---|---|---|---|---|---|---|---|---|---|---|
| | | | 180 | | | | | 185 | | | | | 190 | | |

| Ala | Thr | Tyr | Leu | Asn | Val | Ser | Pro | Phe | Gly | Arg | Asn | Asn | Lys | Gly | Gln |
|---|---|---|---|---|---|---|---|---|---|---|---|---|---|---|---|
| | | | 195 | | | | | 200 | | | | | 205 | | |

| Asn | Ile | Ala | Gly | Val | Gln | Glu | Ala | Ala | Arg | Gly | Ile | Phe | Gly | Val | Asp |
|---|---|---|---|---|---|---|---|---|---|---|---|---|---|---|---|
| 210 | | | | | 215 | | | | | 220 | | | | | |

| Ala | Lys | Asp | Val | Thr | Leu | Pro | Gln | Ala | Ala | Tyr | Ile | Ala | Gly | Leu | Pro |
|---|---|---|---|---|---|---|---|---|---|---|---|---|---|---|---|
| 225 | | | | | 230 | | | | | 235 | | | | | 240 |

| Gln | Ser | Pro | Ile | Thr | Tyr | Ser | Pro | Tyr | Thr | Asn | Thr | Gly | Ala | Leu | Lys |
|---|---|---|---|---|---|---|---|---|---|---|---|---|---|---|---|
| | | | | 245 | | | | | 250 | | | | | 255 | |

| Glu | Asp | Leu | Ser | Ala | Gly | Leu | Ala | Arg | Lys | Asp | Phe | Val | Leu | Phe | Ser |
|---|---|---|---|---|---|---|---|---|---|---|---|---|---|---|---|
| | | | 260 | | | | | 265 | | | | | 270 | | |

| Met | Tyr | Arg | Glu | Gly | Gln | Ile | Thr | Lys | Glu | Gln | Tyr | Glu | Glu | Ala | Lys |
|---|---|---|---|---|---|---|---|---|---|---|---|---|---|---|---|
| | | 275 | | | | | 280 | | | | | 285 | | | |

| Ala | Tyr | Asp | Leu | Thr | Lys | Asp | Phe | Leu | Pro | Gln | Gln | Ile | Ala | Glu | Gln |
|---|---|---|---|---|---|---|---|---|---|---|---|---|---|---|---|
| | 290 | | | | | 295 | | | | | 300 | | | | |

| Thr | Asp | Arg | Glu | Phe | Leu | Tyr | Tyr | Thr | Val | Met | Asn | Glu | Ala | Thr | Arg |
|---|---|---|---|---|---|---|---|---|---|---|---|---|---|---|---|
| 305 | | | | | 310 | | | | | 315 | | | | | 320 |

| Ile | Ile | Ala | Gln | Gln | Leu | Ala | Glu | Lys | Asp | Asn | Ala | Asp | Met | Ser | Asp |
|---|---|---|---|---|---|---|---|---|---|---|---|---|---|---|---|
| | | | | 325 | | | | | 330 | | | | | 335 | |

| Ser | Ser | Val | Ser | Asp | Ala | Tyr | Tyr | Gln | Lys | Ala | Gln | Gln | Thr | Ile | Gln |
|---|---|---|---|---|---|---|---|---|---|---|---|---|---|---|---|
| | | | 340 | | | | | 345 | | | | | 350 | | |

| Asn | Lys | Gly | Tyr | Thr | Ile | His | Ser | Thr | Ile | Asp | Lys | Asp | Val | Tyr | Ala |
|---|---|---|---|---|---|---|---|---|---|---|---|---|---|---|---|
| | | | 355 | | | | | 360 | | | | | 365 | | |

```
Ala Leu Gln Asn Gly Val Glu Asn Tyr Gly Tyr Met Leu Asp Asp Gly
    370                 375                 380

Ala Gly Ser Gln Val Glu Thr Gly Asn Val Leu Met Asp Asn Arg Thr
385                 390                 395                 400

Gly Arg Ile Tyr Gly Phe Val Gly Gly Arg Asn Tyr Ser Gln Asn Gln
                405                 410                 415

Asn Asn His Ala Phe Asp Thr Glu Arg Gln Ala Gly Ser Ser Ile Lys
            420                 425                 430

Pro Val Leu Val Tyr Gly Pro Ala Ile Asp Met Gly Leu Ile Gly Ser
        435                 440                 445

Glu Ser Arg Val Ser Asp Tyr Ala Thr Thr Trp Gln Glu Gly Glu Asn
    450                 455                 460

Ala Gly Glu Lys Ile Val Asn Ala Thr Asn Glu Gly Ser Asn Thr Phe
465                 470                 475                 480

Gln Thr Val Arg Glu Ser Leu Glu Trp Ser Asn Asn Ile Pro Ala Tyr
                485                 490                 495

His Leu Tyr Gln Asp Val Leu Asn Ser Gly Ser Lys Gln Tyr Ala
            500                 505                 510

Tyr Glu His Tyr Leu Ala Lys Met Asn Tyr Pro Ala Asn Asp Asn Trp
        515                 520                 525

Gly Val Glu Ser Ala Pro Leu Gly Thr Val Asp Val Thr Thr Leu Gln
    530                 535                 540

Gln Thr Asn Gly Phe Gln Ala Leu Ala Asn Gly Val Tyr Glu Glu
545                 550                 555                 560

Gly Tyr Ile Ile Asp Ser Ile Thr Asp Asn Ala Gly Asn Val Ile Tyr
                565                 570                 575

Lys His Glu Ser Asn Ser Val Arg Ile Tyr Ser Glu Ala Thr Ala Ser
            580                 585                 590

Ile Met Asn Asp Met Met Arg Ser Val Ile Asn Ala Lys Ile Thr Thr
        595                 600                 605

Pro Phe Lys Asp Ala Ile Ser Ser Leu Asn Gly Asn Leu Gly Lys Ala
    610                 615                 620

Asp Trp Val Gly Lys Thr Gly Ser Thr Asn Glu Tyr Arg Asp Ser Trp
625                 630                 635                 640

Leu Ile Val Ser Thr Pro Ser Ile Thr Ile Ser Ser Trp Ala Gly His
                645                 650                 655

Asp Asp Asn Thr Gly Met Asp Ser Lys Ala Arg Ile Arg Ser Ala Asn
            660                 665                 670

Tyr Leu Ala Asn Leu Ile Asn Gln Ala Tyr Gln Ala Lys Pro Asp Ile
        675                 680                 685

Phe Gly Thr Asp Glu Lys Phe Glu Leu Ser Ser Asp Val Met Lys Lys
    690                 695                 700

Lys Val Ser Gly Phe Thr Gly Gln Thr Pro Gly Lys Val Thr Val Asn
705                 710                 715                 720

Lys Lys Ser Ile Gln Thr Pro Gly Lys Thr Val Glu Ser Leu Trp Ala
                725                 730                 735

Lys Asn Gly Pro Lys Lys Ser Ala Phe Lys Phe Gly Val Gly Gly Thr
            740                 745                 750

Asp Glu Asn Tyr Thr Asp Tyr Trp Asn Thr Ala Ser Ala Tyr Ala Arg
        755                 760                 765

Ala Asn Gln Ala Thr Lys Glu Ser Asp Glu Lys Asp Asp
    770                 775                 780
```

```
<210> SEQ ID NO 14
<211> LENGTH: 803
<212> TYPE: PRT
<213> ORGANISM: Enterococcus faecium
<220> FEATURE:
<221> NAME/KEY: TRANSMEM
<222> LOCATION: (28)..(58)
<220> FEATURE:
<221> NAME/KEY: DOMAIN
<222> LOCATION: (95)..(321)
<220> FEATURE:
<221> NAME/KEY: DOMAIN
<222> LOCATION: (380)..(743)

<400> SEQUENCE: 14
```

Met Tyr His Phe Ile Glu Val Lys Leu Leu Lys Asn Asn Ser Ser Asn
1               5                   10                  15

Asn Lys Gln Lys Pro Thr Thr Ser Ser Gly Gly Asn Val Phe Leu Leu
            20                  25                  30

Ile Leu Asn Val Ile Ile Arg Val Phe Gln Ser Leu Val Val Phe Gly
        35                  40                  45

Val Ile Leu Ile Val Leu Gly Gly Ser Leu Gly Leu Gly Ile Gly Met
    50                  55                  60

Gly Tyr Phe Ala Phe Leu Val Glu Asp Thr Gln Pro Pro Thr Lys Glu
65                  70                  75                  80

Glu Leu Gln Lys Glu Ile Ser Asp Ile Thr Glu Val Ser Lys Met Thr
                85                  90                  95

Tyr Ala Asp Gly Thr Pro Ile Ala Asn Ile Lys Ser Asp Leu Ile Arg
            100                 105                 110

Thr Arg Ile Asn Gly Asp Gln Met Ser Pro Leu Leu Lys Lys Ala Ile
        115                 120                 125

Ile Ser Thr Glu Asp Glu Tyr Phe Glu Glu His His Gly Val Val Pro
    130                 135                 140

Lys Ala Leu Val Arg Ala Leu Ile Ser Asp Ala Thr Gly Ile Gly Gly
145                 150                 155                 160

Ser Ser Gly Gly Ser Thr Leu Thr Gln Gln Leu Val Lys Gln Gln Ile
                165                 170                 175

Leu Thr Asp Glu Thr Thr Phe Lys Arg Lys Ala Asn Glu Ile Leu Leu
            180                 185                 190

Ala Leu Arg Ile Glu Lys Tyr Phe Ser Lys Asp Glu Ile Val Thr Thr
        195                 200                 205

Tyr Leu Asn Val Ser Pro Phe Gly Arg Asn Asn Lys Gly Glu Asn Ile
    210                 215                 220

Ala Gly Val Glu Glu Ala Ala Lys Gly Leu Phe Gly Lys Ser Ala Lys
225                 230                 235                 240

Asp Leu Asn Leu Pro Gln Ala Ala Phe Ile Ala Gly Leu Pro Gln Ser
                245                 250                 255

Pro Ile Val Tyr Thr Pro Tyr Thr Asn Thr Gly Ala Leu Lys Asp Asp
            260                 265                 270

Leu Ser Leu Gly Met Lys Arg Lys Asp Phe Val Leu Phe Ser Met Tyr
        275                 280                 285

Arg Glu Lys Ala Ile Ser Gln Lys Glu Tyr Glu Ala Lys Ala Tyr
    290                 295                 300

Asp Leu Lys Lys Asp Phe Leu Pro Thr Glu Gln Ala Asn Val Asn Thr
305                 310                 315                 320

Glu Gly Tyr Leu Tyr Tyr Thr Val Leu Asp Lys Ala Val Glu Ile Val
                325                 330                 335

```
Met Asp Leu Asp Met Lys Lys Ala Lys Val Asn Arg Asp Asp Leu Asp
            340                 345                 350

Gln Val Gly Leu Asp Gln Tyr Glu Gln Ala Arg Arg Glu Ile Gln
            355                 360                 365

Ser Gln Gly Tyr Thr Ile Gln Ser Thr Ile Asp Gln Asn Ile Tyr Asn
370                 375                 380

Thr Met Gln Thr Ala Val Ala Asn Tyr Gly Tyr Leu Leu Asp Asp Gly
385                 390                 395                 400

Thr Ala Asp Val Asn Gly Asn Thr Met Ile Glu Thr Gly Asn Ile Leu
            405                 410                 415

Met Asp Asn Ala Thr Gly Arg Ile Leu Gly Phe Ile Gly Gly Arg Asn
            420                 425                 430

Phe Asp Ile Asn Gln Asn Asn His Ala Phe Asn Ala Asp Arg Gln Val
            435                 440                 445

Gly Ser Thr Ile Lys Pro Ile Ser Val Tyr Gly Pro Ala Ile Asp Gln
            450                 455                 460

Gly Ile Ile Gly Ser Glu Ser Arg Leu Ala Asn Tyr Pro Thr Thr Tyr
465                 470                 475                 480

Ala Asp Gly Arg Glu Phe Val Asn Ser Thr Asn Val Asp Leu Asn Gln
            485                 490                 495

Phe Val Thr Val Arg Asn Ala Leu Asn Trp Ser Phe Asn Ile Pro Val
            500                 505                 510

Val His Val Asn Asn Glu Leu Arg Lys Lys Met Gly Asp Asp Asn Phe
            515                 520                 525

Ser Tyr Asn His Tyr Leu Ser Lys Met Asn Tyr Pro Ala Ser Asp Ala
530                 535                 540

Trp Ala Tyr Glu Ser Ala Pro Leu Gly Ser Val Glu Thr Asn Val Val
545                 550                 555                 560

Thr Gln Thr Asn Gly Phe Gln Ala Leu Ala Asn Lys Gly Lys Tyr Gln
            565                 570                 575

Lys Ala Tyr Met Ile Glu Lys Ile Thr Asp Asn Ser Gly His Val Val
            580                 585                 590

Tyr Glu His Lys Asp Glu Gly Thr Gln Val Tyr Ser Pro Ala Thr Ala
            595                 600                 605

Ser Ile Met Asn Asp Leu Leu Arg Ser Val Val Asp Ser Ala Asn Thr
610                 615                 620

Thr Lys Phe Lys Pro Thr Leu Ala Gly Leu Asn Pro His Leu Ala Ser
625                 630                 635                 640

Ala Asp Trp Val Gly Lys Thr Gly Thr Thr Asp Glu Phe Lys Asp Ser
            645                 650                 655

Trp Leu Ile Val Ser Thr Pro Thr Val Thr Leu Ser Ser Trp Ala Gly
            660                 665                 670

His Asp Leu Pro Ala Pro Met Thr Met Thr Ser Gly Asp Asn Asn Gly
            675                 680                 685

Asn Tyr Met Ala Asn Leu Ala Asn Ala Leu Tyr Tyr Ala Asn Pro Glu
            690                 695                 700

Leu Phe Gly Ile Gly Gln Lys Phe Glu Leu Asp Pro Ser Val Ile Lys
705                 710                 715                 720

Ser Lys Val Ser Glu Phe Thr Gly Glu Lys Pro Gly Ser Ile Thr Tyr
            725                 730                 735

Asn Gly Ala Lys Phe Asn Thr Pro Gly Lys Thr Thr Ser Tyr Tyr
            740                 745                 750
```

```
Ala Lys Asp Gly Ala Pro Gln Ser Thr Tyr Lys Phe Gly Ile Gly
        755                 760                 765
Thr Asp Ser Asn Tyr Ala Ser Tyr Trp Gly Asn Leu Ala Pro Arg Ala
    770                 775                 780
Thr Thr Asn Asn Asn Asn Asn Asn Lys Asn Asn Asp Asn Lys Lys
785                 790                 795                 800
Asn Asn Asn

<210> SEQ ID NO 15
<211> LENGTH: 727
<212> TYPE: PRT
<213> ORGANISM: Staphylococcus aureus
<220> FEATURE:
<221> NAME/KEY: TRANSMEM
<222> LOCATION: (27)..(49)
<220> FEATURE:
<221> NAME/KEY: DOMAIN
<222> LOCATION: (77)..(295)
<220> FEATURE:
<221> NAME/KEY: DOMAIN
<222> LOCATION: (337)..(631)

<400> SEQUENCE: 15

Met Thr Glu Asn Lys Gly Ser Ser Gln Pro Lys Asn Gly Asn Asn
1               5                   10                  15
Gly Gly Lys Ser Asn Ser Lys Lys Asn Arg Asn Val Lys Arg Thr Ile
            20                  25                  30
Ile Lys Ile Ile Gly Phe Met Ile Ile Ala Phe Phe Val Leu Leu
        35                  40                  45
Leu Gly Ile Leu Leu Phe Ala Tyr Tyr Ala Trp Lys Ala Pro Ala Phe
    50                  55                  60
Thr Glu Ala Lys Leu Gln Asp Pro Ile Pro Ala Lys Ile Tyr Asp Lys
65                  70                  75                  80
Asn Gly Glu Leu Val Lys Thr Leu Asp Asn Gly Gln Arg His Glu His
                85                  90                  95
Val Asn Leu Lys Asp Val Pro Lys Ser Met Lys Asp Ala Val Leu Ala
            100                 105                 110
Thr Glu Asp Asn Arg Phe Tyr Glu His Gly Ala Leu Asp Tyr Lys Arg
        115                 120                 125
Leu Phe Gly Ala Ile Gly Lys Asn Leu Thr Gly Gly Phe Gly Ser Glu
    130                 135                 140
Gly Ala Ser Thr Leu Thr Gln Gln Val Val Lys Asp Ala Phe Leu Ser
145                 150                 155                 160
Gln His Lys Ser Ile Gly Arg Lys Ala Gln Glu Ala Tyr Leu Ser Tyr
                165                 170                 175
Arg Leu Glu Gln Glu Tyr Ser Lys Asp Asp Ile Phe Gln Val Tyr Leu
            180                 185                 190
Asn Lys Ile Tyr Cys Ser Asp Gly Val Thr Gly Ile Lys Ala Ala Ala
        195                 200                 205
Lys Tyr Tyr Phe Asn Lys Asp Leu Lys Asp Leu Asn Leu Ala Glu Glu
    210                 215                 220
Ala Tyr Leu Ala Gly Leu Pro Gln Val Pro Asn Asn Tyr Asn Ile Tyr
225                 230                 235                 240
Asp His Pro Lys Ala Ala Glu Asp Arg Lys Asn Thr Val Leu Tyr Leu
                245                 250                 255
Met His Tyr His Lys Arg Ile Thr Asp Lys Gln Trp Gly Asp Ala Lys
            260                 265                 270
```

```
Lys Ile Asp Leu Lys Ala Asn Leu Val Asn Arg Thr Pro Glu Glu Arg
                275                 280                 285

Gln Asn Ile Asp Thr Asn Gln Asp Ser Glu Tyr Asn Ser Tyr Val Asn
        290                 295                 300

Phe Val Lys Ser Glu Leu Met Asn Asn Lys Ala Phe Lys Asp Glu Asn
305                 310                 315                 320

Leu Gly Asn Val Leu Gln Ser Gly Ile Lys Ile Tyr Thr Asn Met Asp
                325                 330                 335

Lys Asp Val Gln Lys Thr Leu Gln Asn Asp Val Asp Asn Gly Ser Phe
            340                 345                 350

Tyr Lys Asn Lys Asp Gln Gln Val Gly Ala Thr Ile Leu Asp Ser Lys
        355                 360                 365

Thr Gly Gly Leu Val Ala Ile Ser Gly Gly Arg Asp Phe Lys Asp Val
    370                 375                 380

Val Asn Arg Asn Gln Ala Thr Asp Pro His Pro Thr Gly Ser Ser Leu
385                 390                 395                 400

Lys Pro Phe Leu Ala Tyr Gly Pro Ala Ile Glu Asn Met Lys Trp Ala
                405                 410                 415

Thr Asn His Ala Ile Gln Asp Glu Ser Ser Tyr Gln Val Asp Gly Ser
            420                 425                 430

Thr Phe Arg Asn Tyr Asp Thr Lys Ser His Gly Thr Val Ser Ile Tyr
        435                 440                 445

Asp Ala Leu Arg Gln Ser Phe Asn Ile Pro Ala Leu Lys Ala Trp Gln
    450                 455                 460

Ser Val Lys Gln Asn Ala Gly Asn Asp Ala Pro Lys Lys Phe Ala Ala
465                 470                 475                 480

Lys Leu Gly Leu Asn Tyr Glu Gly Asp Ile Gly Pro Ser Glu Val Leu
                485                 490                 495

Gly Gly Ser Ala Ser Glu Phe Ser Pro Thr Gln Leu Ala Ser Ala Phe
            500                 505                 510

Ala Ala Ile Ala Asn Gly Gly Thr Tyr Asn Asn Ala His Ser Ile Gln
        515                 520                 525

Lys Val Val Thr Arg Asp Gly Glu Thr Ile Glu Tyr Asp His Thr Ser
    530                 535                 540

His Lys Ala Met Ser Asp Tyr Thr Ala Tyr Met Leu Ala Glu Met Leu
545                 550                 555                 560

Lys Gly Thr Phe Lys Pro Tyr Gly Ser Ala Tyr Gly His Gly Val Ser
                565                 570                 575

Gly Val Asn Met Gly Ala Lys Thr Gly Thr Gly Thr Tyr Gly Ala Glu
            580                 585                 590

Thr Tyr Ser Gln Tyr Asn Leu Pro Asp Asn Ala Ala Lys Asp Val Trp
        595                 600                 605

Ile Asn Gly Phe Thr Pro Gln Tyr Thr Met Ser Val Trp Met Gly Phe
    610                 615                 620

Ser Lys Val Lys Gln Tyr Gly Glu Asn Ser Phe Val Gly His Ser Gln
625                 630                 635                 640

Gln Glu Tyr Pro Gln Phe Leu Tyr Glu Asn Val Met Ser Lys Ile Ser
                645                 650                 655

Ser Arg Asp Gly Glu Asp Phe Lys Arg Pro Ser Ser Val Ser Gly Ser
            660                 665                 670

Ile Pro Ser Ile Asn Val Ser Gly Ser Gln Asp Asn Thr Thr Asn
        675                 680                 685

Arg Ser Thr His Gly Gly Ser Asp Thr Ser Ala Asn Ser Ser Gly Thr
```

```
                      690                 695                 700
Ala Gln Ser Asn Asn Thr Arg Ser Gln Gln Ser Arg Asn Ser Gly
705                 710                 715                 720

Gly Leu Thr Gly Ile Phe Asn
                725

<210> SEQ ID NO 16
<211> LENGTH: 821
<212> TYPE: PRT
<213> ORGANISM: Streptococcus pneumoniae
<220> FEATURE:
<221> NAME/KEY: TRANSMEM
<222> LOCATION: (41)..(71)
<220> FEATURE:
<221> NAME/KEY: DOMAIN
<222> LOCATION: (271)..(336)
<220> FEATURE:
<221> NAME/KEY: DOMAIN
<222> LOCATION: (396)..(688)

<400> SEQUENCE: 16

Met Gln Asn Gln Leu Asn Glu Leu Lys Arg Lys Met Leu Glu Phe Phe
1               5                   10                  15

Gln Gln Lys Gln Lys Asn Lys Lys Ser Ala Arg Pro Gly Lys Lys Gly
                20                  25                  30

Ser Ser Thr Lys Lys Ser Lys Thr Leu Asp Lys Ser Ala Ile Phe Pro
            35                  40                  45

Ala Ile Leu Leu Ser Ile Lys Ala Leu Phe Asn Leu Leu Phe Val Leu
        50                  55                  60

Gly Phe Leu Gly Gly Met Leu Gly Ala Gly Ile Ala Leu Gly Tyr Gly
65                  70                  75                  80

Val Ala Leu Phe Asp Lys Val Arg Val Pro Gln Thr Glu Glu Leu Val
                85                  90                  95

Asn Gln Val Lys Asp Ile Ser Ser Ile Ser Glu Ile Thr Tyr Ser Asp
                100                 105                 110

Gly Thr Val Ile Ala Ser Ile Glu Ser Asp Leu Leu Arg Thr Ser Ile
            115                 120                 125

Ser Ser Glu Gln Ile Ser Glu Asn Leu Lys Lys Ala Ile Ile Ala Thr
130                 135                 140

Glu Asp Glu His Phe Lys Glu His Lys Gly Val Val Pro Lys Ala Val
145                 150                 155                 160

Ile Arg Ala Thr Leu Gly Lys Phe Val Gly Leu Gly Ser Ser Ser Gly
                165                 170                 175

Gly Ser Thr Leu Thr Gln Leu Ile Lys Gln Gln Val Val Gly Asp
            180                 185                 190

Ala Pro Thr Leu Ala Arg Lys Ala Ala Glu Ile Val Asp Ala Leu Ala
        195                 200                 205

Leu Glu Arg Ala Met Asn Lys Asp Glu Ile Leu Thr Thr Tyr Leu Asn
    210                 215                 220

Val Ala Pro Phe Gly Arg Asn Asn Lys Gly Gln Asn Ile Ala Gly Ala
225                 230                 235                 240

Arg Gln Ala Ala Glu Gly Ile Phe Gly Val Asp Ala Ser Gln Leu Thr
                245                 250                 255

Val Pro Gln Ala Ala Phe Leu Ala Gly Leu Pro Gln Ser Pro Ile Thr
            260                 265                 270

Tyr Ser Pro Tyr Glu Asn Thr Gly Glu Leu Lys Ser Asp Glu Asp Leu
        275                 280                 285
```

-continued

```
Glu Ile Gly Leu Arg Arg Ala Lys Ala Val Leu Tyr Ser Met Tyr Arg
    290                 295                 300

Thr Gly Ala Leu Ser Lys Asp Glu Tyr Ser Gln Tyr Lys Asp Tyr Asp
305                 310                 315                 320

Leu Lys Gln Asp Phe Leu Pro Ser Gly Thr Val Thr Gly Ile Ser Arg
                325                 330                 335

Asp Tyr Leu Tyr Phe Thr Thr Leu Ala Glu Ala Gln Glu Arg Met Tyr
            340                 345                 350

Asp Tyr Leu Ala Gln Arg Asp Asn Val Ser Ala Lys Glu Leu Lys Asn
        355                 360                 365

Glu Ala Thr Gln Lys Phe Tyr Arg Asp Leu Ala Ala Lys Glu Ile Glu
370                 375                 380

Asn Gly Gly Tyr Lys Ile Thr Thr Thr Ile Asp Gln Lys Ile His Ser
385                 390                 395                 400

Ala Met Gln Ser Ala Val Ala Asp Tyr Gly Tyr Leu Leu Asp Asp Gly
                405                 410                 415

Thr Gly Arg Val Glu Val Gly Asn Val Leu Met Asp Asn Gln Thr Gly
            420                 425                 430

Ala Ile Leu Gly Phe Val Gly Gly Arg Asn Tyr Gln Glu Asn Gln Asn
        435                 440                 445

Asn His Ala Phe Asp Thr Lys Arg Ser Pro Ala Ser Thr Thr Lys Pro
450                 455                 460

Leu Leu Ala Tyr Gly Ile Ala Ile Asp Gln Gly Leu Met Gly Ser Glu
465                 470                 475                 480

Thr Ile Leu Ser Asn Tyr Pro Thr Asn Phe Ala Asn Gly Asn Pro Ile
                485                 490                 495

Met Tyr Ala Asn Ser Lys Gly Thr Gly Met Met Thr Leu Gly Glu Ala
            500                 505                 510

Leu Asn Tyr Ser Trp Asn Ile Pro Ala Tyr Trp Thr Tyr Arg Met Leu
        515                 520                 525

Arg Glu Asn Gly Val Asp Val Lys Gly Tyr Met Glu Lys Met Gly Tyr
530                 535                 540

Glu Ile Pro Glu Tyr Gly Ile Glu Ser Leu Pro Met Gly Gly Gly Ile
545                 550                 555                 560

Glu Val Thr Val Ala Gln His Thr Asn Gly Tyr Gln Thr Leu Ala Asn
                565                 570                 575

Asn Gly Val Tyr His Gln Lys His Val Ile Ser Lys Ile Glu Ala Ala
            580                 585                 590

Asp Gly Arg Val Val Tyr Glu Tyr Gln Asp Lys Pro Val Gln Val Tyr
        595                 600                 605

Ser Lys Ala Thr Ala Thr Ile Met Gln Gly Leu Leu Arg Glu Val Leu
610                 615                 620

Ser Ser Arg Val Thr Thr Thr Phe Lys Ser Asn Leu Thr Ser Leu Asn
625                 630                 635                 640

Pro Thr Leu Ala Asn Ala Asp Trp Ile Gly Lys Thr Gly Thr Thr Asn
                645                 650                 655

Gln Asp Glu Asn Met Trp Leu Met Leu Ser Thr Pro Arg Leu Thr Leu
            660                 665                 670

Gly Gly Trp Ile Gly His Asp Asp Asn His Ser Leu Ser Arg Arg Ala
        675                 680                 685

Gly Tyr Ser Asn Asn Ser Asn Tyr Met Ala His Leu Val Asn Ala Ile
690                 695                 700

Gln Gln Ala Ser Pro Ser Ile Trp Gly Asn Glu Arg Phe Ala Leu Asp
```

```
                705                710                 715                 720
        Pro Ser Val Val Lys Ser Glu Val Leu Lys Ser Thr Gly Gln Lys Pro
                        725                 730                 735

Gly Lys Val Ser Val Glu Gly Lys Glu Val Glu Val Thr Gly Ser Thr
                        740                 745                 750

Val Thr Ser Tyr Trp Ala Asn Lys Ser Gly Ala Pro Ala Thr Ser Tyr
                    755                 760                 765

Arg Phe Ala Ile Gly Gly Ser Asp Ala Asp Tyr Gln Asn Ala Trp Ser
                770                 775                 780

Ser Ile Val Gly Ser Leu Pro Thr Pro Ser Ser Ser Ser Ser Ser Ser
        785                 790                 795                 800

Ser Ser Ser Ser Asp Ser Ser Asn Ser Ser Thr Thr Arg Pro Ser Ser
                        805                 810                 815

Ser Arg Ala Arg Arg
                        820
```

ANTIBIOTIC COMPOSITIONS AND RELATED SCREENING METHODS

RELATED APPLICATION

This application claims the benefit of and priority to U.S. Provisional Application Ser. No. 61/021,279, filed Jan. 15, 2008, Taiwan Application Serial No. 097125469, filed Jul. 4, 2008, and Japan Application Serial No. 2008-178187, filed Jul. 7, 2008, and the contents of each are incorporated by reference herein in their entirety.

BACKGROUND

This disclosure relates to methods for expressing and purifying full-length class A penicillin-binding protein from bacteria. This disclosure also relates to high-throughput screening methods for an antibiotic.

SUMMARY

According to a feature of the present disclosure, a method is disclosed comprising obtaining a candidate for screening; carrying out an anisotropy measurement assay with a class A penicillin-binding protein comprising at least a transmembrane and a transglycosylase domains; and determining the effectiveness of the candidate as a transglycosylase inhibitor.

According to a feature of the present disclosure, a high throughput device is contemplated, having multiple versions of a class A penicillin-binding protein comprising at least transmembrane and a transglycosylase domain for determining the effectiveness of a candidate agent as a transglycosylation inhibitor. The assays may be carried out as either competition displacement assays or direct binding assays or both.

According to a feature of the present disclosure, a method is disclosed comprising amplifying DNA sequence of full-length penicillin-binding protein from bacterial genomic DNA; cloning the DNA sequence into a vector, expressing the DNA sequence in a host cell to obtain a full-length penicillin-binding protein, solubilizing the protein with a detergent, and purifying the protein.

According to a feature of the present disclosure, a composition is disclosed comprising an agent having the formula selected from the group consisting of:

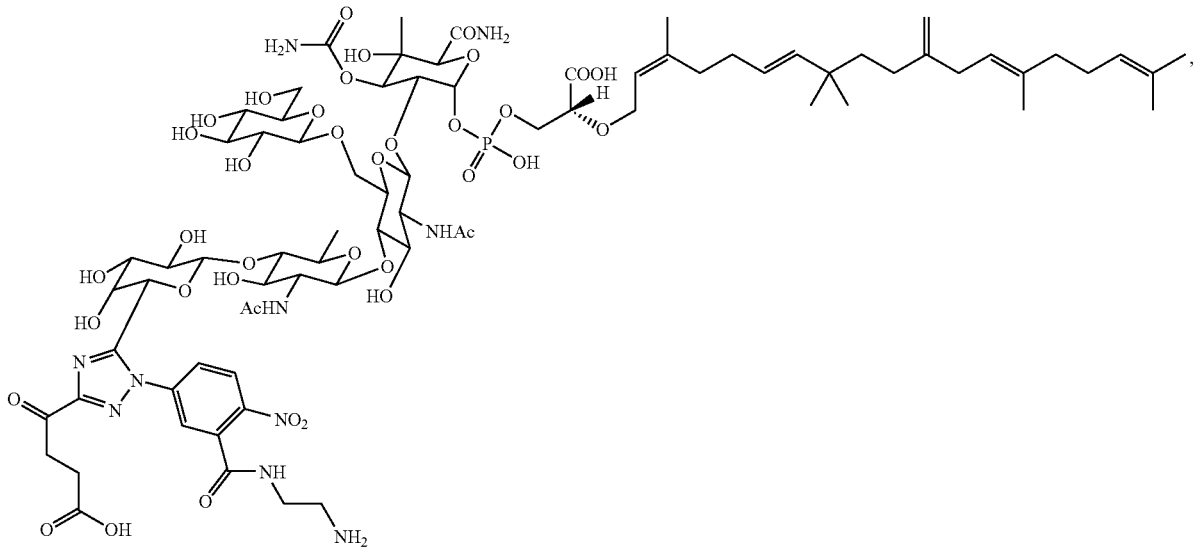

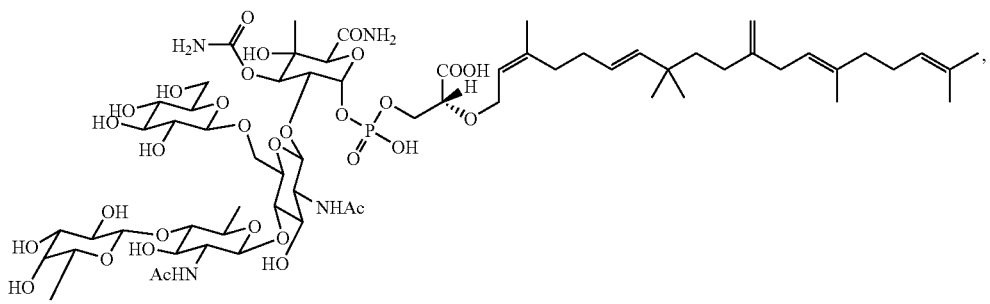

-continued
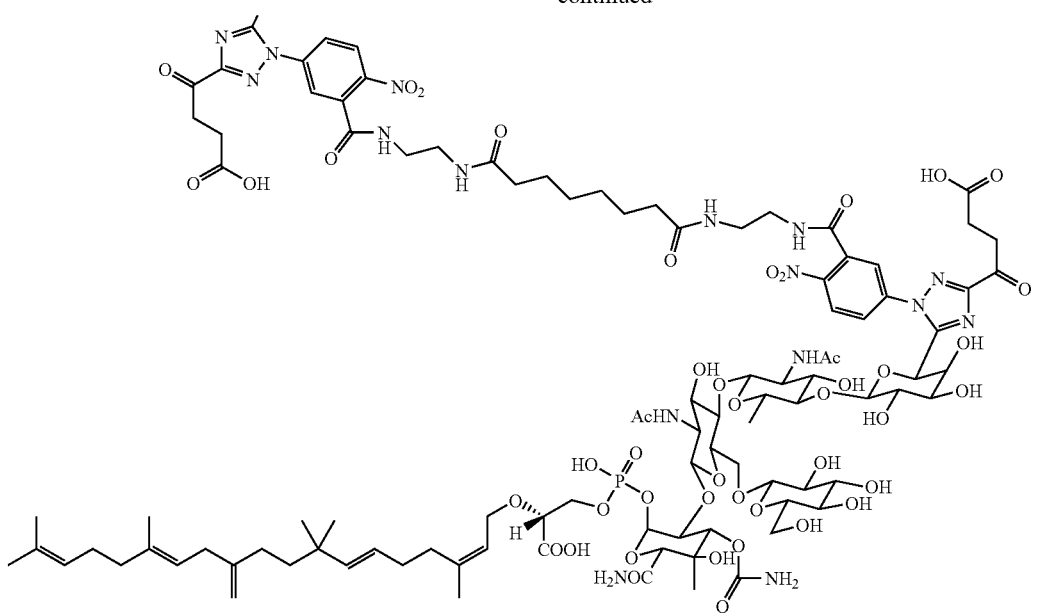
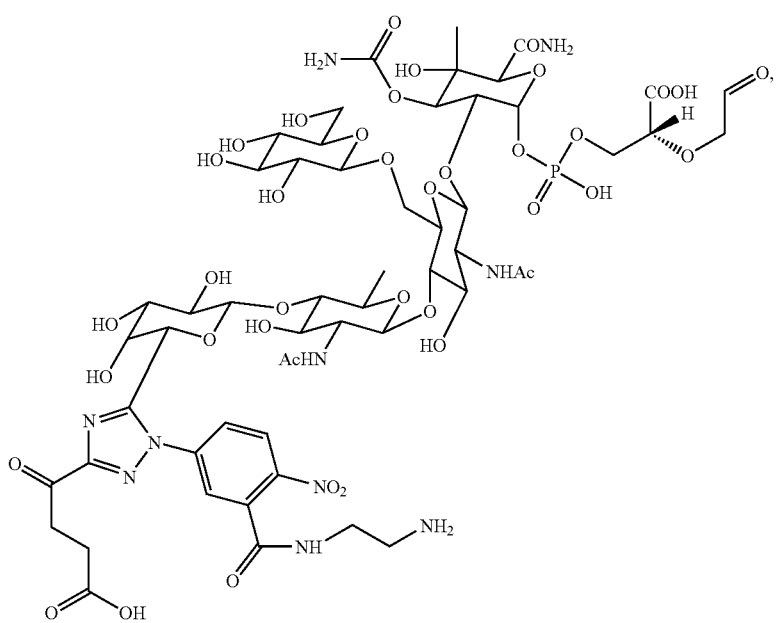
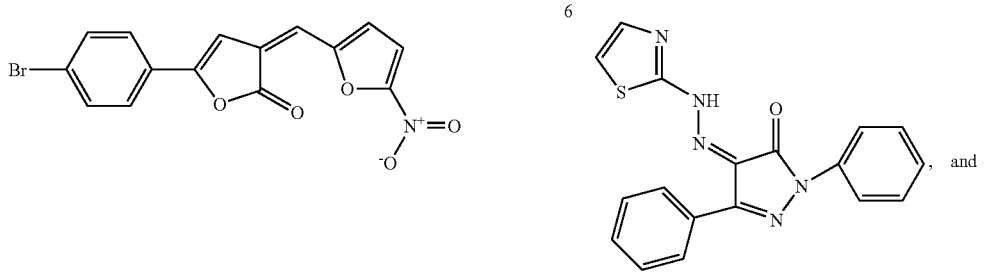
, and

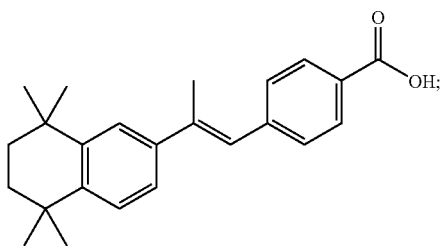
and a pharmaceutically acceptable carrier.
According to a feature of the present disclosure, a method is disclosed comprising treating a subject having a bacterial infection or susceptible for a bacterial infection with a pharmaceutical composition comprising an agent having the formula selected from the group consisting of:
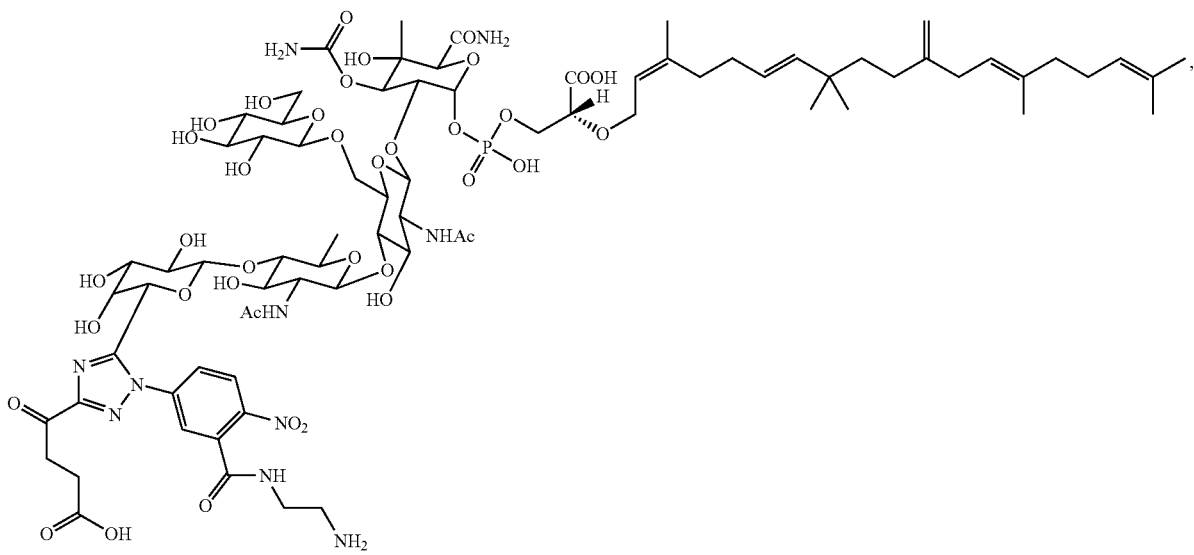
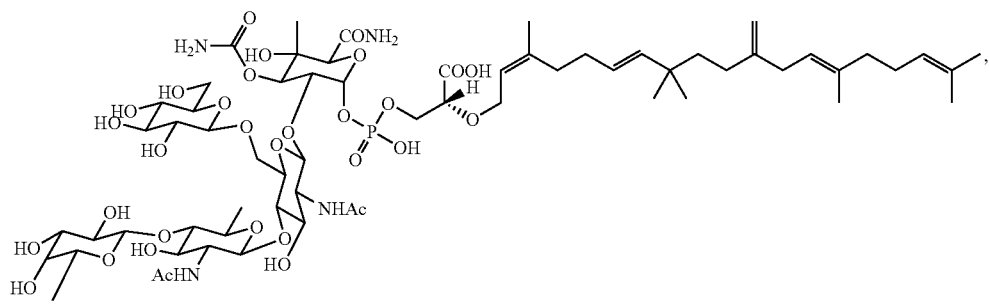

-continued
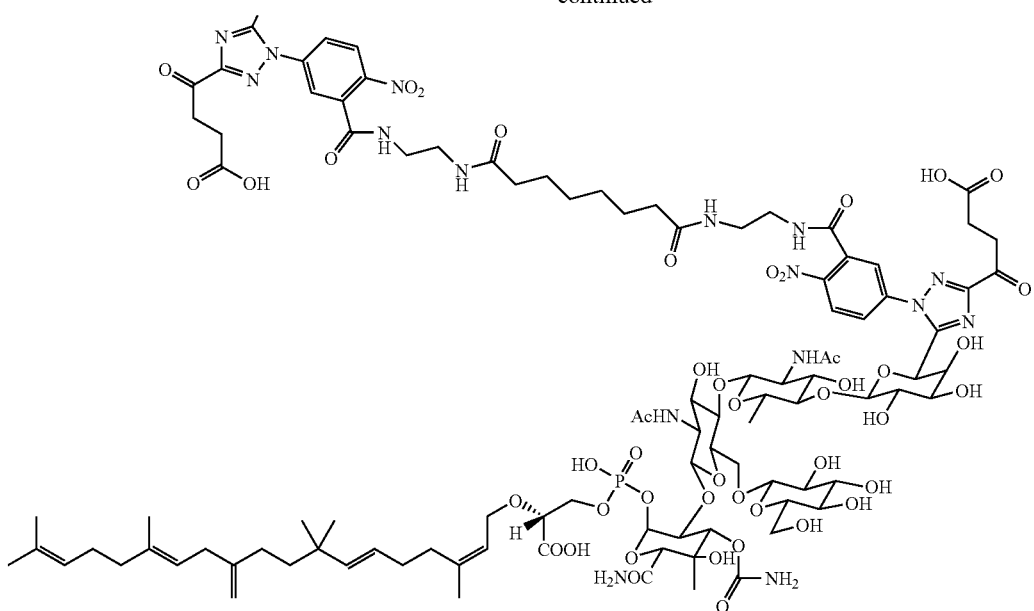
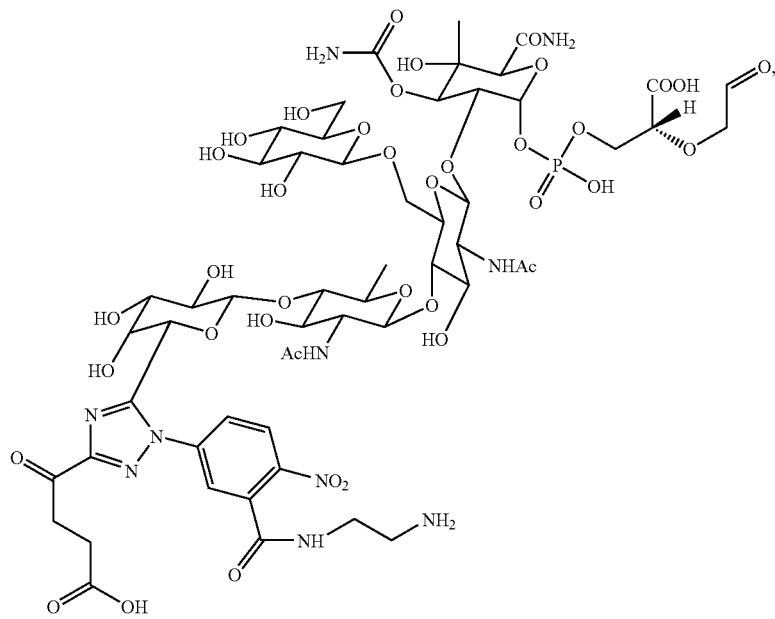
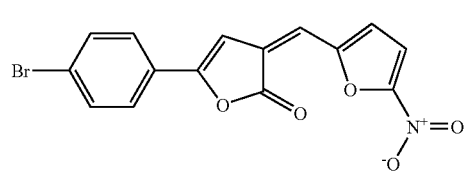
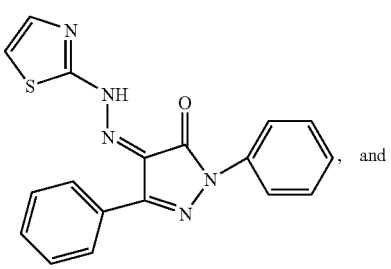
, and

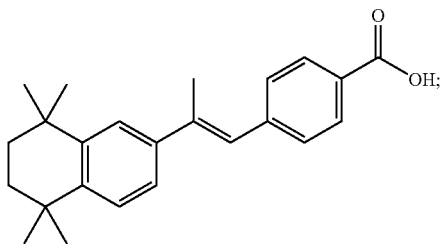

and a pharmaceutically acceptable carrier.

According to implementations of the present disclosure, the antibiotic is a transglycosylase inhibitor, and, preferably, it is (Z)-5-(4-bromophenyl)-3-((5-nitrofuran-2-yl)methylene)furan-2(3H)-one; (Z)-1,3-diphenyl-4-(2-(thiazol-2-yl)hydrazono-1H-pyrazol-5(4H)-one; (E)-4-(2-(5,5,8,8,-tetramethyl-5,6,7,8-tetrahydronaphthalen-2-yl)prop-1-enyl) benzoic acid.

According to implementations of the present disclosure, the protein comprises three domains which, from N terminus to C terminus, are transmembrane, transglycosylase and transpeptidase.

According to implementations of the present disclosure, the moenomycin used as fluorescent probe binds the penicillin-binding protein when fluorescence-anisotropy-based assay is carried out.

According to implementations of the present disclosure, the hits screened by the method of present disclosure, which are antibiotics, inhibit the growth bacterium which is *Escherichia coli, Klebsiella pneumoniae, Streptococcus pneumoniae, Shigella flexneri, Haemophilus influenzae, Helicobacter pylori, Citrobacter freundii, Bordetella pertussi, Staphylococcus aureus* (MRSA Mu50), *Bacillus subtilis, Pseudomonas aeruginosa, Clostridium difficile, Enterococcus faecium, Enterococcus faecalis, Salmonella enterica* or *Neisseria gonorrhoeae*.

According to implementations of the present disclosure, the bacterium is *E. faecalis* or *S. aureus*.

According to implementations of the present disclosure, a method is provided for expressing and purifying full-length class A penicillin-binding protein from a bacterium comprising: (a) amplifying DNA sequence of full-length penicillin-binding protein from bacterial genomic DNA; (b) cloning the DNA sequence into a vector; (c) expressing the DNA sequence in a host cell to obtain a full-length penicillin-binding protein; (d) solubilizing the protein with a detergent; and (e) purifying the protein; wherein the detergent is n-decyl-β-D-maltopyranoside, n-undecyl-β-D-maltopyranoside, n-dodecyl-β-D-maltopyranoside, n-octyl-β-D-glucopyranoside, n-nonyl-β-D-glucopyranoside, n-tetradecylphosphocholine, n-dodedyl-N,N-dimethylamine-N-oxide, 3-[(3-Cholamidopropyl)-dimethylammonio]-1-propane sulfonate or α-[4-(1,1,3,3-Tetramethylbutyl)phenyl]-w-hydroxy-poly(oxy-1,2-ethanediyl).

According to implementations of the present disclosure, the bacterium is *Escherichia coli, Klebsiella pneumoniae, Streptococcus pneumoniae, Shigella flexneri, Haemophilus influenzae, Helicobacter pylori, Citrobacter freundii, Bordetella pertussi, Staphylococcus aureus* (MRSA Mu50), *Bacillus subtilis, Pseudomonas aeruginosa, Clostridium difficile, Enterococcus faecium, Enterococcus faecalis, Salmonella enterica* or *Neisseria gonorrhoeae*.

According to implementations of the present disclosure, the detergent used for purifying full length class A penicillin-binding protein is n-dodecyl-β-D-maltopyranoside.

According to implementations of the present disclosure, the full length protein comprises three domains, which, from N terminus to C terminus, are transmembrane, transglycosylase and transpeptidase.

DRAWINGS

The above-mentioned features and objects of the present disclosure will become more apparent with reference to the following description taken in conjunction with the accompanying drawings wherein like reference numerals denote like elements and in which:

FIG. 1 shows inhibition of transglycosylase by moenomycin and binding affinities of truncated PBP variants, according to implementations of the present disclosure. FIG. 1(A) shows Moenomycin A (1) inhibiting the transglycosylation step in the bacterial cell wall synthesis. FIG. 1(B) is a schematic representation of the PBP variants used for moenomycin binding studies;

FIG. 2 shows sequence alignment of full-length bi-functional PBPs from 16 bacterial strains (Seq. ID Nos. 1-16), according to implementations of the present disclosure;

Figure 4:
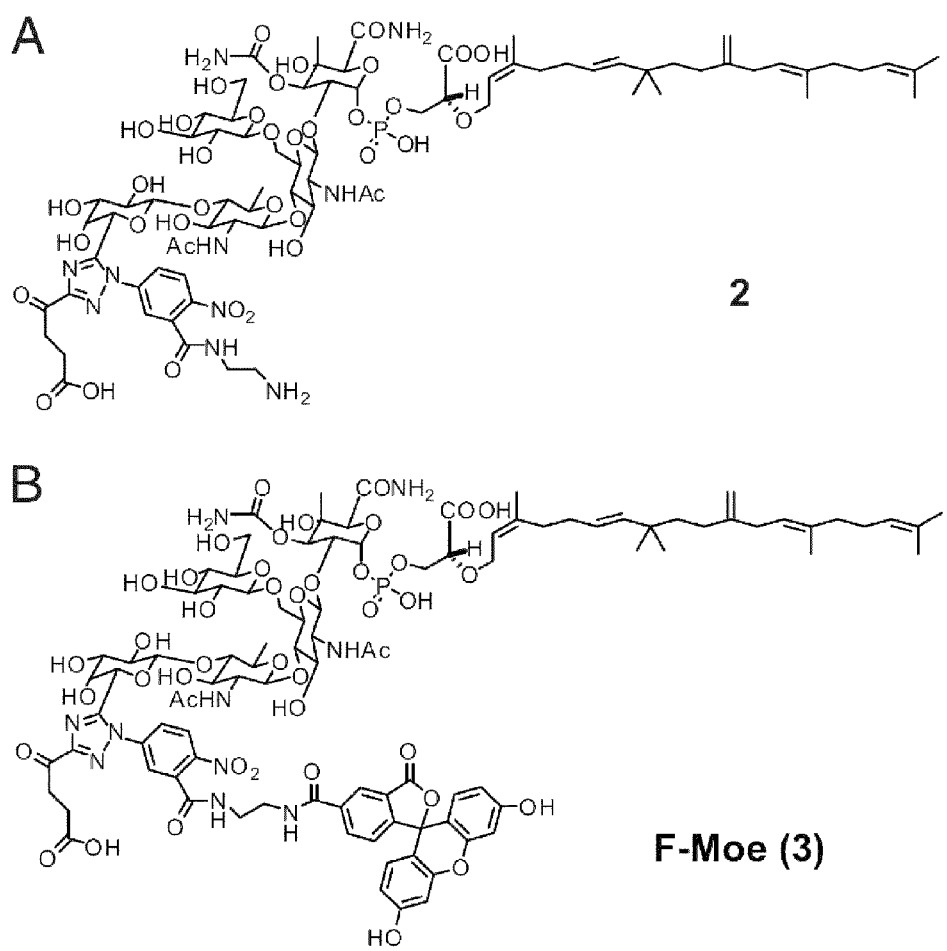
Figure 4:
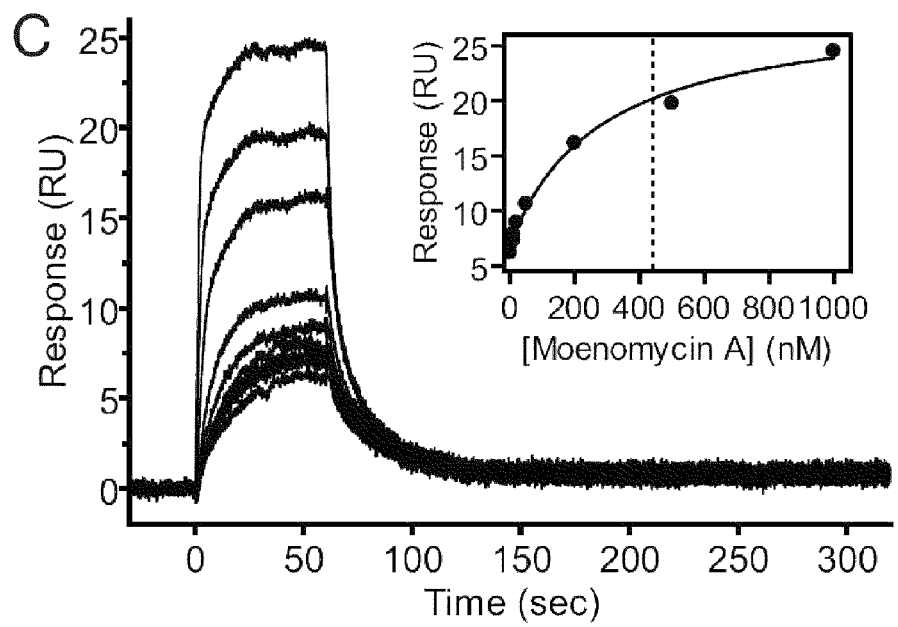
Figure 4:
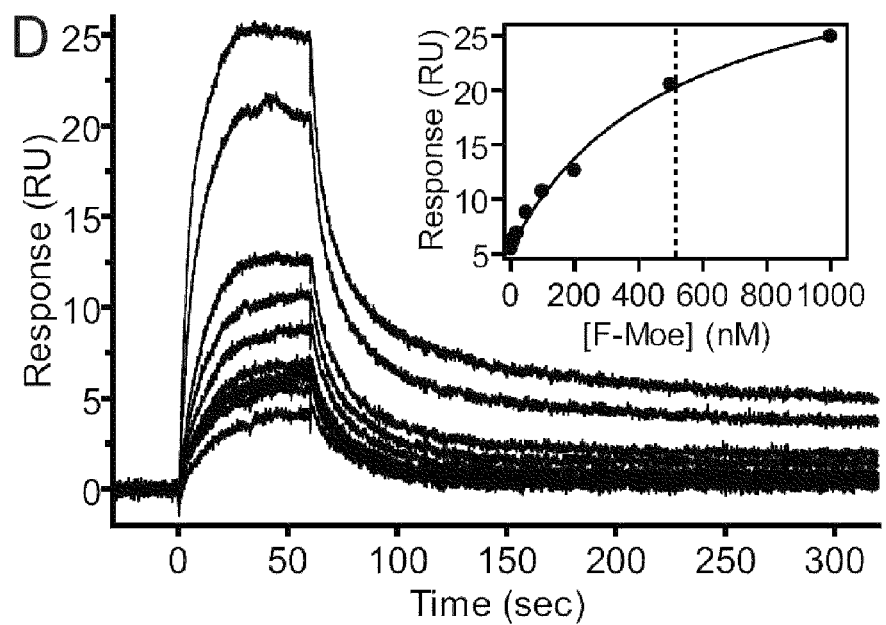
Figure 5:
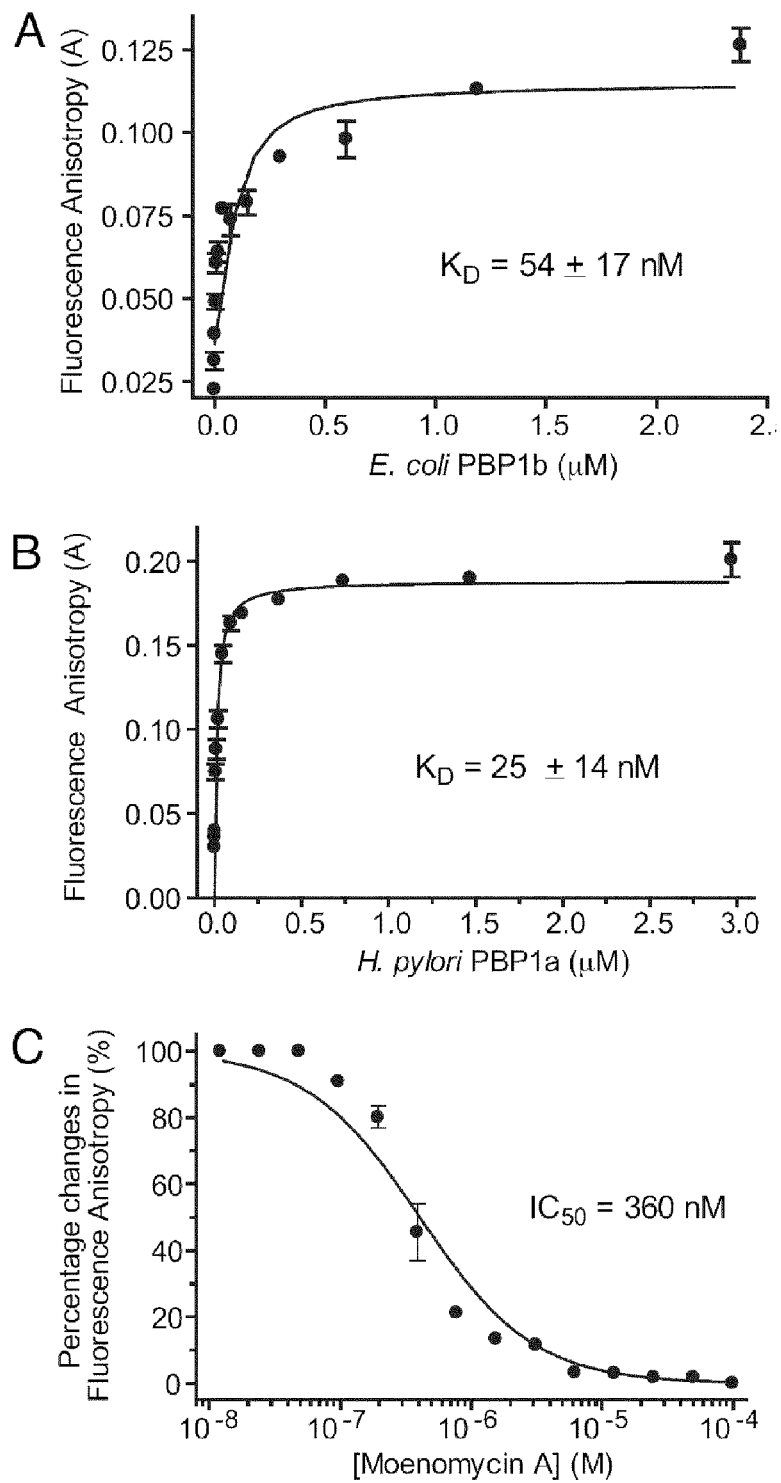
Figure 6:
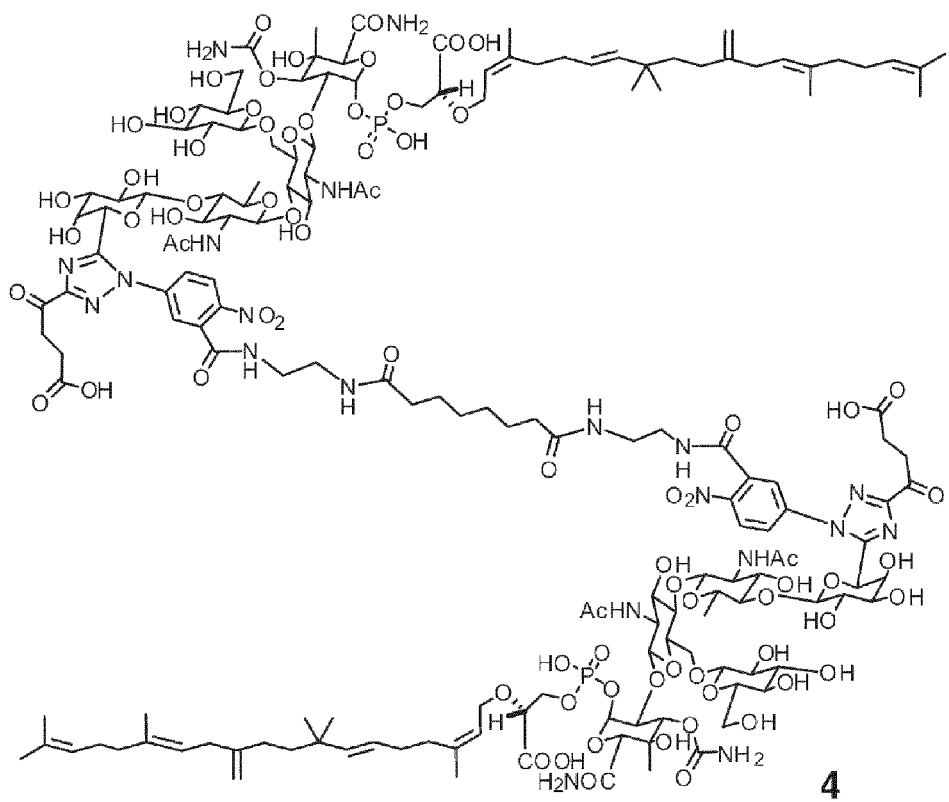
Figure 6:
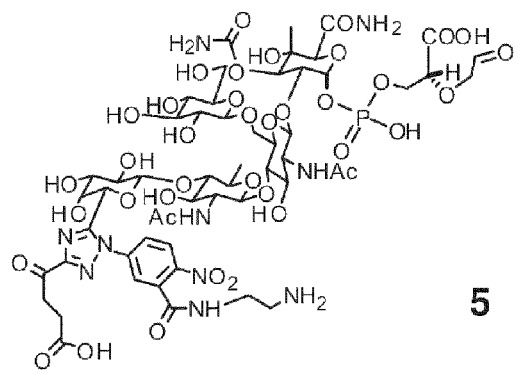
Figure 7:
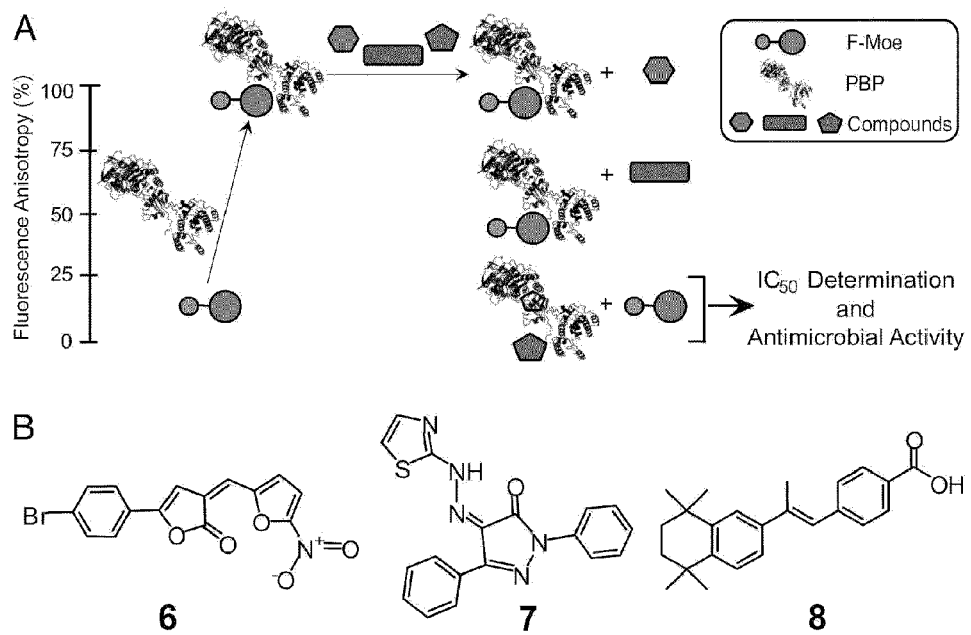

FIG. 4 shows the design of a novel fluorescence anisotropy assay for transglycosylase, according to implementations of the present disclosure. FIG. 4(A) shows the chemical structures of the modified moenomycin A (2), and FIG. 4(B) shows the chemical structures of the fluorescein-labeled moenomycin, F-Moe (3). FIG. 4(C) shows the SPR analysis of the binding activity of moenomycin A to *E. coli* PBP1b, and FIG. 4(D) shows the SPR analysis of the binding activity of F-Moe to *E. coli* PBP1b;

FIG. 5 shows the development of high-throughput FA assay for transglycosylase. FIG. 5(A) shows the concentration-dependent changes in fluorescence anisotropy observed when *E. coli* PBP1b bound to F-Moe. FIG. 5(B) shows the improved FA assay with the *Helicobacter pylori* PBP1a. FIG. 5(C) shows the displacement of the PBP1a bound F-Moe complex by unlabeled moenomycin at various concentrations;

FIG. 6 illustrates chemical structures of moenomycin derivatives (4 and 5), according to implementations of the present disclosure; and FIG. 7 illustrates screening for small molecules as TG inhibitors using the class A PBPs, according to implementations of the present disclosure. FIG. 7(A) shows the scheme of HTS for TG inhibitors using FA assay. FIG. 7(B) shows chemical structures of the HTS hits (compounds 6-8).

DETAILED DESCRIPTION

All scientific terms are to be given their ordinary meanings as understood by those of skill in the art, unless an alternate meaning is set forth below. In case of conflict, the definitions set forth in this specification shall control.

As used in this application, the term "host cell" means a cell that may be used to express a particular DNA molecule, vector, or plasmid other than the naturally occurring segments of the host cell's chromosomal DNA.

As used in this application, the term "vector" means a DNA molecule that is at least originally separate from the chromosomal DNA of a host cell, and may include plasmids.

As used in this application, the term "detergent" means any agent that causes a substance to become soluble or more soluble in a solution.

Many common bacterial pathogens such as *Staphylococcus aureus*, *Streptococcus pneumoniae*, and *Enterococcus faecalis* have become multidrug-resistant and emerged as a public health concern, demanding an unmet medical need for novel antibiotics.

Figure 1:
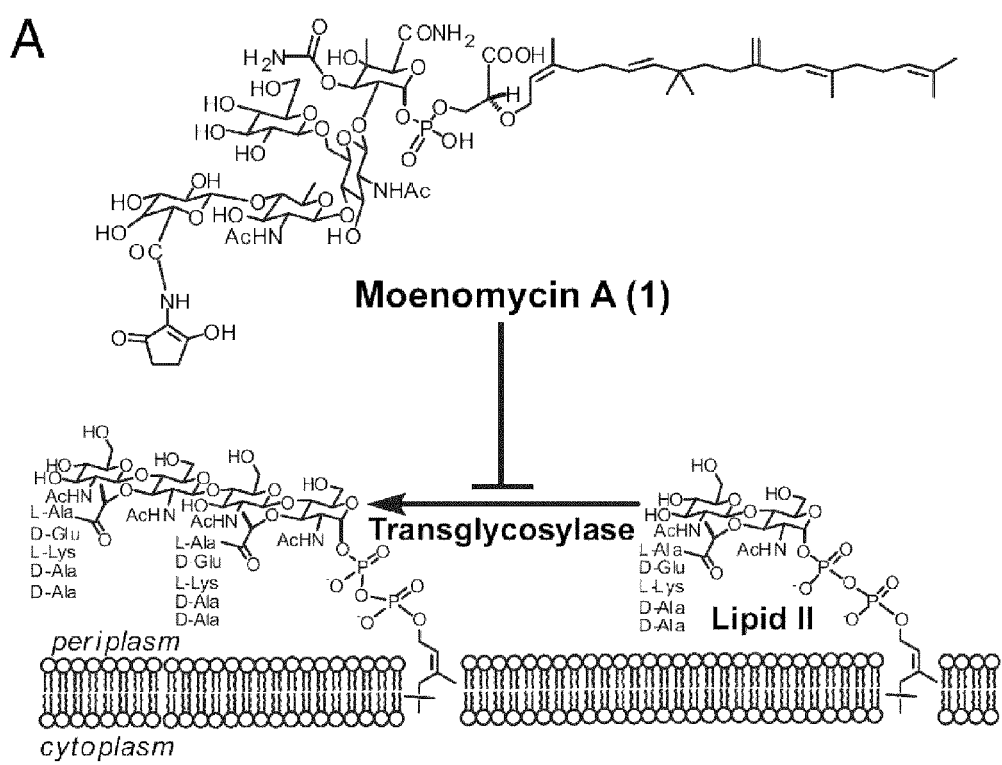

The bacterial cell wall or peptidoglycan synthetic pathway has been targeted for the development of antibacterial agents. The synthesis of peptidoglycan consists of several steps including the synthesis of lipid I and lipid II followed by the final transglycosylation and transpeptidation of lipid II to form peptidoglycan. Many of the current antibiotics are β-lactam derivatives that target the transpeptidation. No medicines are yet developed to inhibit the transglycosylation process. The only known potent inhibitors for transglycosylase (TG) are moenomycin complexes (flavomycin), including moenomycin A (FIG. 1A, Moe A, 1), A12, C1, C3 and C4. Among them, Moe A is the most abundant agent in its family. FIG. 1 shows inhibition of transglycosylase by moenomycin and binding affinities of truncated PBP variants. FIG. 1(A) shows Moenomycin A (1) inhibiting the transglycosylation step in the bacterial cell wall synthesis. The unique antibacterial properties have prompted chemists to synthesize moenomycin fragments and derivatives. The first total synthesis of moenomycin A was achieved recently by Kahne and co-workers. Its biosynthesis pathway has also been elucidated. However, due to poor bioavailability, flavomycin is only employed as an antibiotic growth promoter in animal feeds.

Transglycosylation is mainly catalyzed by bi-functional class A penicillin-binding proteins (PBPs). PBPs are the major enzymes responsible for the last-step cell-wall formation by polymerization of N-acetylglucosamine-N-acetylmuramyl-pentapeptide, and cross-linking between penta-peptide, and thus have been considered as one of the important targets for antibiotics discovery. These membrane-anchored enzymes consist of three distinct protein domains, i.e., transmembrane (TM), transglycosylase (TG) and transpeptidase (TP) domains from their amino to carboxyl termini. The recent X-ray crystal structures of the PBP2 extracellular domain from *S. aureus* and the transglycosylase domain of PBP1a from *A. aeolicus* have provided invaluable structural insight into the plausible mechanism of cell-wall peptidoglycan polymerization, albeit lacking the information regarding the role of the transmembrane domain of PBPs in catalysis. The transmembrane domain of PBPs has been speculated to interact with the lipid moiety of moenomycin or lipid II.

The characterization of class A PBPs and the identification of TG inhibitors require functional PBP and lipid II as the substrate for the polymerization. The limited availability of lipid II has hampered the enzymatic study as well as the development of inhibitors. To get around the lipid II deficiency, a majority of screening methods to search for TG inhibitors rely mainly on moenomycin. Based on moenomycin activity, low-throughput inhibitor screening methods using SPR assays or radioactive assays have been developed. A TG activity assay platform that is amenable to high-throughput screening is thus desirable for inhibitor identification.

According to implementations, a high throughput device is contemplated. According to implementations, the high throughput device comprises a platform having multiple versions of a class A penicillin-binding protein comprising at least transmembrane and a transglycosylase domain for determining the effectiveness of a candidate agent as a transglycosylation inhibitor. FA assays may then be carried out on the platform, for example either competition displacement assays or direct binding assays or both, and a determination made of the effectiveness of the candidate agent determined.

According to implementations, a method is disclosed comprising obtaining a candidate for screening; carrying out an anisotropy measurement assay, such as fluorescent anisotropy, with a class A penicillin-binding protein comprising at least a transmembrane and a transglycosylase domains; and determining the effectiveness of the candidate as a transglycosylase inhibitor.

According to implementations, a method is provided for amplifying DNA sequence of full-length penicillin-binding protein from bacterial genomic DNA; cloning the DNA sequence into a vector, expressing the DNA sequence in a host cell to obtain a full-length penicillin-binding protein, solubilizing the protein with a detergent, and purifying the protein.

According to similar implementations of the present disclosure, a high-throughput screening method is provided for identification of TG inhibitors and antibiotic development. The method may comprise: (a) providing a candidate for screening; (b) carrying out fluorescence anisotropy measurement with fluorescent moenomycin and class A penicillin-binding protein comprising transmembrane and transglycosylase domains; (c) calculating fluorescence anisotropy value and $K_D$ value; (d) calculating $K_I$ and $IC_{50}$ value of an transglycosylase inhibitor; and (e) determining minimal inhibitory concentration of the inhibitor; wherein $K_D$ is the dissociation constant between the moenomycin and the protein; $K_I$ is the dissociation constant between the inhibitor and the protein; $IC_{50}$ is inhibitory concentration needed to inhibit bacterial growth by half; minimal inhibitory concentration is the minimal concentration of the inhibitor that prevents bacterial growth.

A high-throughput screening method according to implementations of the present disclosure may be used to determine the protein binding affinity for a candidate inhibitor or compound. Where a protein may be known or suspected to play a role in the activity of a target cell, the binding affinity of the candidate may correspond to the effectiveness of the candidate as an inhibitor of the protein with regard to the known or suspected cell activity.

An FA-based PBP binding assay according to implementations of the present disclosure has been demonstrated as a powerful HTS assay for the discovery of novel antibacterial agents. An FA-based assay according to implementations of the present disclosure can be used as a robust primary screening to quickly identify the potential hits from large antibiotic compound libraries. Furthermore, an efficient and economical TG assay in an HTS format according to implementations of the present disclosure may facilitate the identification of new TG inhibitors. The selected hits may be further screened using antibacterial assay or lipid II polymerizing activity analysis to identify leads.

According to implementations of the present disclosure, a method is provided for expressing and purifying full-length class A penicillin-binding protein from a bacterium comprising: (a) amplifying DNA sequence of full-length penicillin-binding protein from bacterial genomic DNA; (b) cloning the DNA sequence into a vector; (c) expressing the DNA sequence in a host cell to obtain a full-length penicillin-binding protein; (d) solubilizing the protein with a detergent; and (e) purifying the protein.

A method for expressing and purifying proteins according to implementations of the present disclosure may be applied to obtain a variety of proteins that are capable of being expressed in a host cell. Such proteins may correspond to proteins naturally generated within living organisms and may include proteins known or suspected to play a role in the activity of a cell of the living organism.

Proteins obtained by implementations of the disclosed method may be used for binding experiments for screening purposes. For example, proteins obtained may be used to evaluate the binding activity of candidate compounds to determine the effectiveness of the compound as an inhibitor of the protein obtained.

PBPs may be obtained by implementations of the disclosed method, including PBP variants including various combinations of transmembrane (TM), transglycosylase (TG) and transpeptidase (TP) domains. For example, the following variants of domain combinations may be obtained: (i) full-length protein containing the TM, TG, and TP domains (TM+TG+TP), (ii) TG+TP, (iii) TM+TG, (iv) TG alone, and (v) TP alone (see FIG. 1B).

A method for expressing and purifying full-length class A penicillin-binding protein from a bacterium according to implementations of the present disclosure may be used to obtain the PBPs from different species with purity greater than 80%. Implementations of the method may include selection of a DNA sequence from bacterial genomic DNA that is known to be active in certain activities of the corresponding bacterium.

Pharmaceutical compositions are also contemplated. The methods of the present disclosure allow for the rapid determination of agents that are useful as antibiotics. For example, as disclosed in more detail in Example 9 and 10, compounds 2 through 10 were tested for antibiotic activity. Moenomycin analogs 2 and 4, as well as small molecules 6-8, were confirmed to have both antibacterial and TG binding inhibition activities (see Table 2).

As disclosed above, pharmaceutical preparations are herein disclosed having antibiotic or TG binding inhibition activities. According to implementations, one or more of the following agents for a pharmaceutical comprised of a pharmaceutical carrier and one of the following agents:

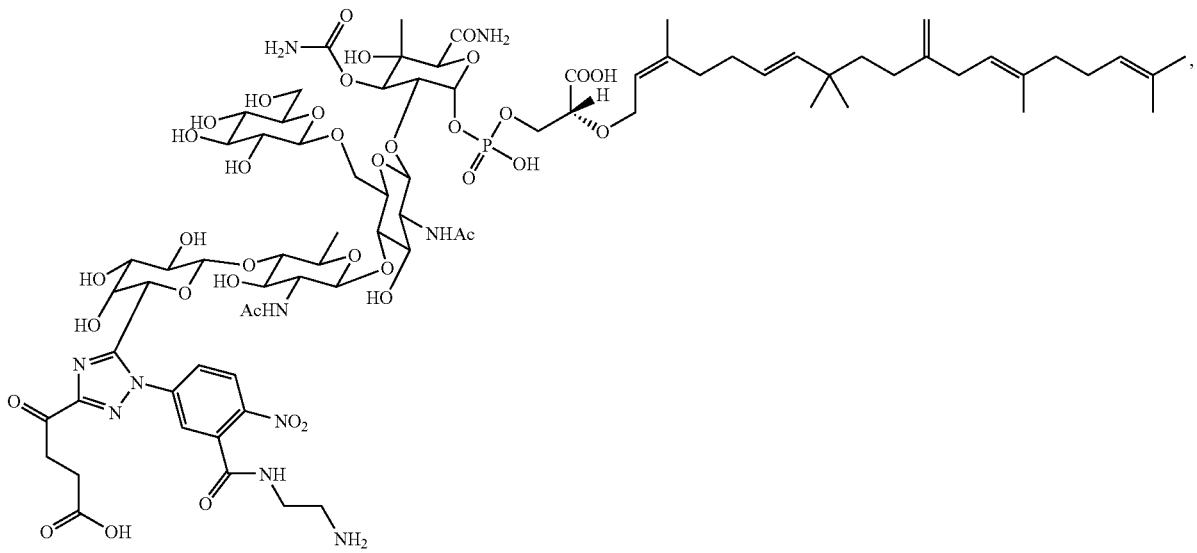

2

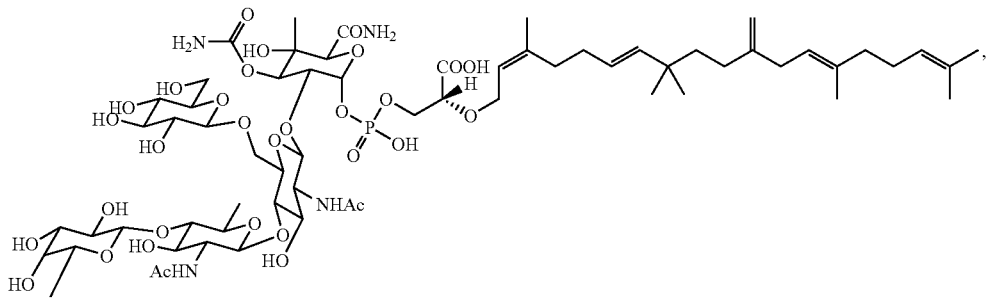

4

-continued
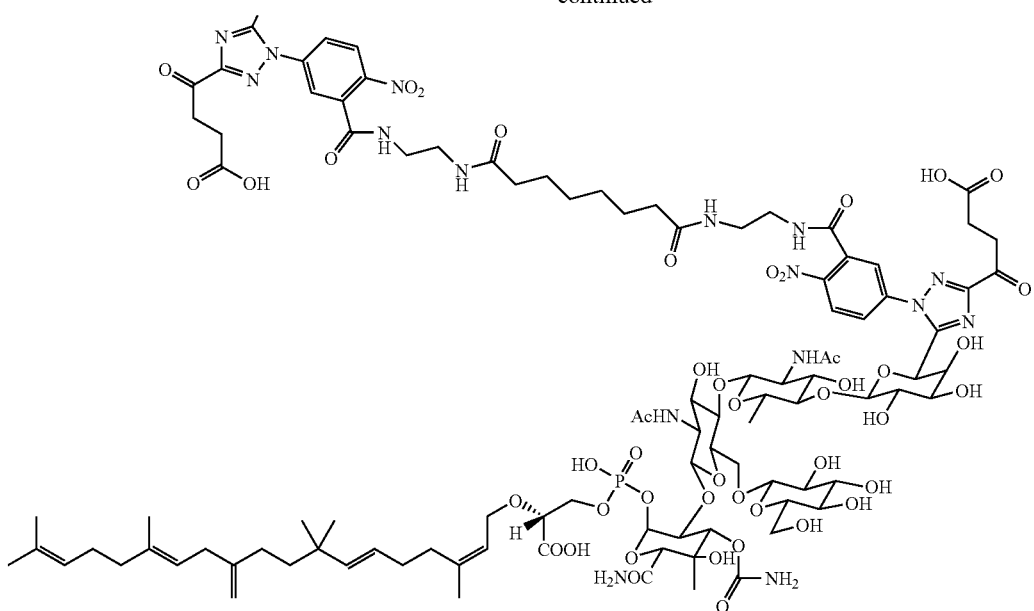
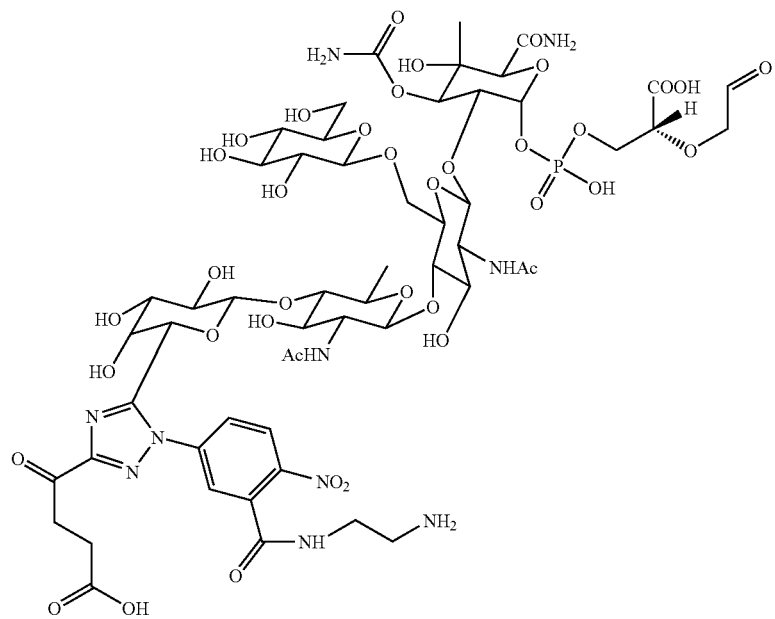
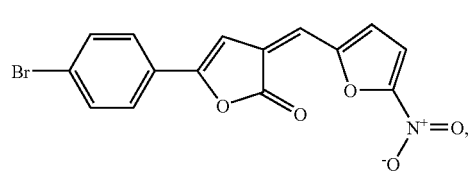
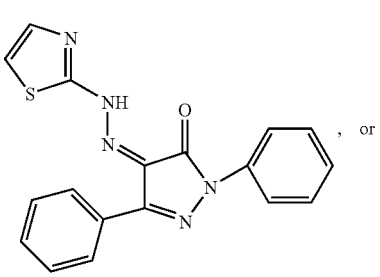

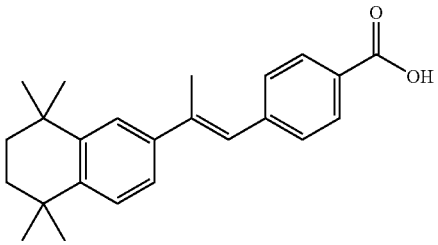

8 and administered to a subject in need of an antibiotic due to bacterial infection or as a preventative measure.

Pharmaceutical Compositions

The instant disclosure also provides pharmaceutical compositions. In some implementations, the pharmaceutical compositions comprise agents, namely moenomycin analogs and small molecules (TG Inhibitors) shown to have antibiotic activity via inhibition of TG binding. In such pharmaceutical compositions, the TG Inhibitors form the "active compound" or "agent." According to implementations, the pharmaceutical compositions are administered to a subject to in need of anti-bacterial therapy, including gram-negative bacteria. According to other implementations, the pharmaceutical compositions are administered to a subject having a bacterial infection to inhibit the transgylcosylation process during the synthesis of bacterial cell wall.

In addition to active compound, the pharmaceutical compositions preferably comprise at least one pharmaceutically acceptable carrier. As used herein the language "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into the compositions. A pharmaceutical composition is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Subject as used herein refers to humans and non-human primates (e.g., guerilla, macaque, marmoset), livestock animals (e.g., sheep, cow, horse, donkey, pig), companion animals (e.g., dog, cat), laboratory test animals (e.g., mouse, rabbit, rat, guinea pig, hamster), captive wild animals (e.g., fox, deer) and any other organisms who can benefit from the agents of the present disclosure. There is no limitation on the type of animal that could benefit from the presently described agents. Human subjects are expressly contemplated. A subject regardless of whether it is a human or non-human organism may be referred to as a patient, individual, animal, host, or recipient.

Pharmaceutical compositions suitable for injectable use include sterile aqueous solutions (where water-soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition should be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, or sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from a container or dispenser which contains a suitable propellant, e.g., a gas such as carbon dioxide, or a nebulizer. Other delivery methods and devices common in the art, including mechanically actuated atomizing-like devices are expressly contemplated.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For epidermal, dermal, or transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one implementation, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to cell-specific antigens) can also be used as pharmaceutically acceptable carriers. These can be prepared according to methods known to those skilled in the art, for example, as described in U.S. Pat. No. 4,522,811, incorporated by reference herein.

It is advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit high therapeutic indices are preferred. While compounds that exhibit toxic side effects can be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in subjects. The dosage of such compounds lies preferably within a range of circulating concentrations that include the $ED_{50}$ with little or no toxicity. The dosage can vary within this range depending upon the dosage form employed and the route of administration utilized. For any compound used in the method of the disclosure, the therapeutically effective dose can be estimated initially from cell culture assays. A dose can be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in subjects. Levels in plasma can be measured, for example, by high performance liquid chromatography.

As defined herein, a therapeutically effective amount of an active compound of the disclosure may range, for examples, from about 0.001 to 30 mg/kg body weight, about 0.01 to 25 mg/kg body weight, about 0.1 to 20 mg/kg body weight, or about 1 to 10 mg/kg, 2 to 9 mg/kg, 3 to 8 mg/kg, 4 to 7 mg/kg, or 5 to 6 mg/kg body weight. Without limitation, the active compound can be administered between one time per week and three or more times per day, for between about 1 to 10 weeks, for example between 2 to 8 weeks, between about 3 to 7 weeks, or for about 4, 5, or 6 weeks. The skilled artisan will appreciate that certain factors can influence the dosage and timing required to effectively treat a subject, including but not limited to the severity of the disease or disorder, previous treatments, the general health or age of the subject, and other diseases present. Moreover, treatment of a subject with a therapeutically effective amount of a pharmaceutical composition of the disclosure can include a single treatment or, preferably, can include a series of treatments.

For those agents determined to be transglycosylation inhibitors or antibiotics, further testing may then be performed for the candidate agent to determine agents that are both good transglycosylation inhibitors and also having reasonably bioavailability.

EXAMPLES

The present disclosure and its implementations may be further illustrated by the following examples.

Example 1

Domain Requirement of Moenomycin Binding to Class A Penicillin-Binding Proteins (Bi-Functional Transglycosylases)

Protein constructs containing different domains of PBP1b from *E. coli* were expressed and purified with suitable detergents for moenomycin binding activities using Surface Plasmon Resonance (SPR). Five *E. coli* PBP1b variants were expressed and purified: 1) full-length protein containing transmembrane, transglycosylase and transpeptidase domains (TM+TG+TP), 2) TG+TP, 3) TM+TG, 4) TG, and 5) TP (FIG. 1B).

FIG. 1 shows inhibition of transglycosylase by moenomycin and binding affinities of truncated PBP variants. FIG. 1(B) is a schematic representation of the PBP variants used for moenomycin binding studies. The full-length PBP (TM+TG+TP) contains amino acid residues 1-844 of the E. coli PBP1b P02919. TG+TP (residues 88-844), TM+TG (residues 1-409), TG (residues 195-409), and TP (residues 444-736) are truncated variants with the part of the full-length PBP1b. The moenomycin binding constant ($K_D$) for these variants were determined using SPR.

After immobilization of the target proteins on the sensor chip, different concentrations of moenomycin were passed through the surface and the binding affinities were determined. As shown in FIG. 1B, the moenomycin binding activity of the PBP without the transmembrane domain (TG+TP) was about 5-fold lower in comparison to that of the full-length PBP1b. On the other hand, the binding affinity of TM+TG is similar to that of the full-length protein. The results suggested that the transmembrane domain may play an important role in moenomycin binding.

The moenomycin binding affinity of the full-length was determined as $4.4 \times 10^{-7}$ M, similar to the inhibition potency for the TG reaction. Using a TP variant as a control protein, it was confirmed that the determined binding affinities of moenomycin to the PBP1b variants is significant and specific. Binding studies using truncated PBP1b variants further showed that the binding affinities of the TM+TG variant is similar to that of the full-length protein. The role of the TM domain in Moe A binding was shown in the observation that the binding capacity of the TG+TP variant decreased five-fold compared with that of full-length PBP1b (FIG. 1B).

Example 2

Correlation of PBP Binding Activities and Minimal Inhibitory Concentration (MIC) of Moenomycin Since the transmembrane domain contributes significantly to moenomycin binding, full-length PBPs were prepared from 16 Gram-negative and -positive bacteria (Table 1) for moenomycin binding studies. The genes of Class A PBPs were identified using NCBI database and all of them were confirmed to have TG and TP motifs (FIG. 2).

Figure 2:
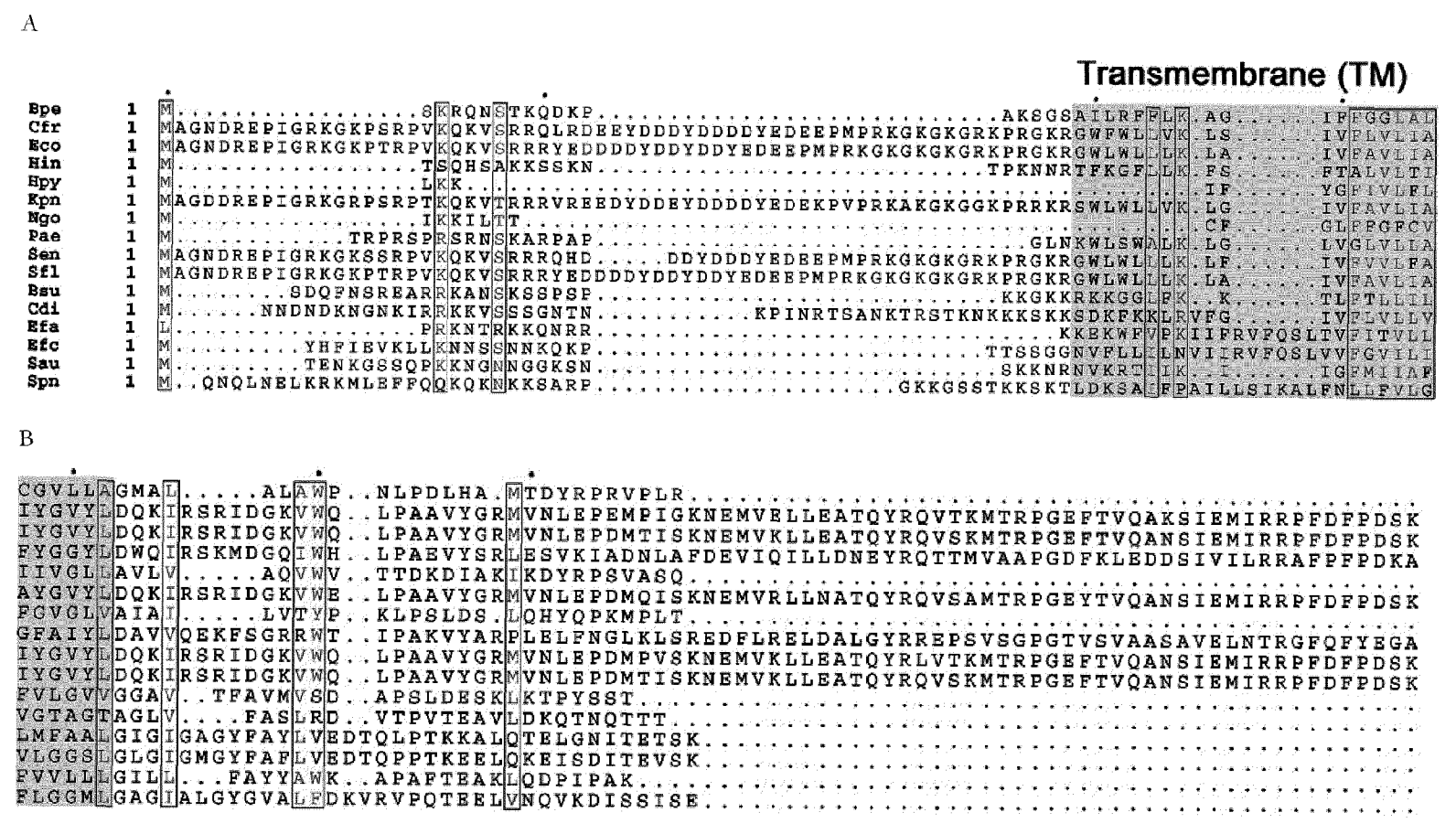
Figure 2:
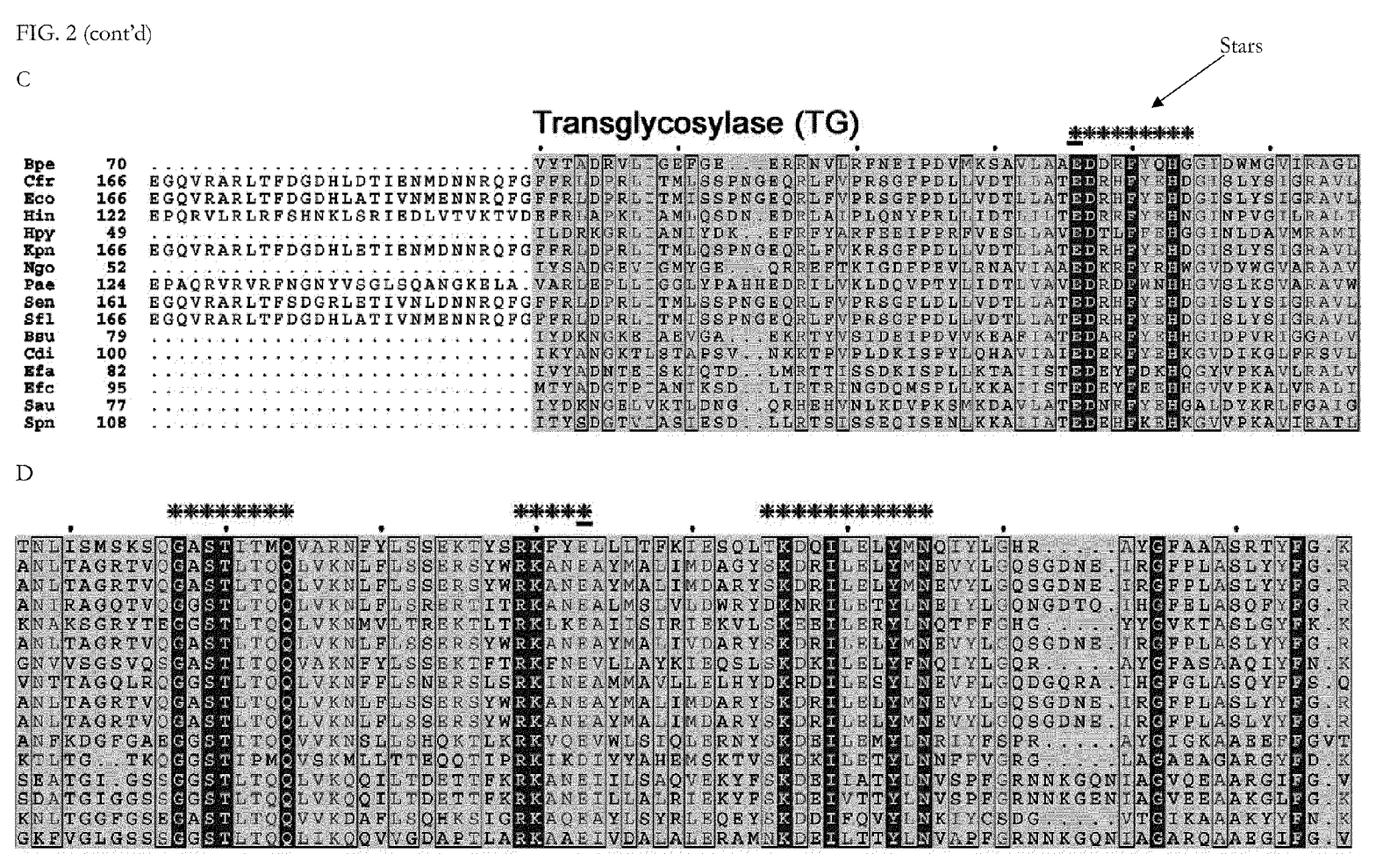
Figure 2:
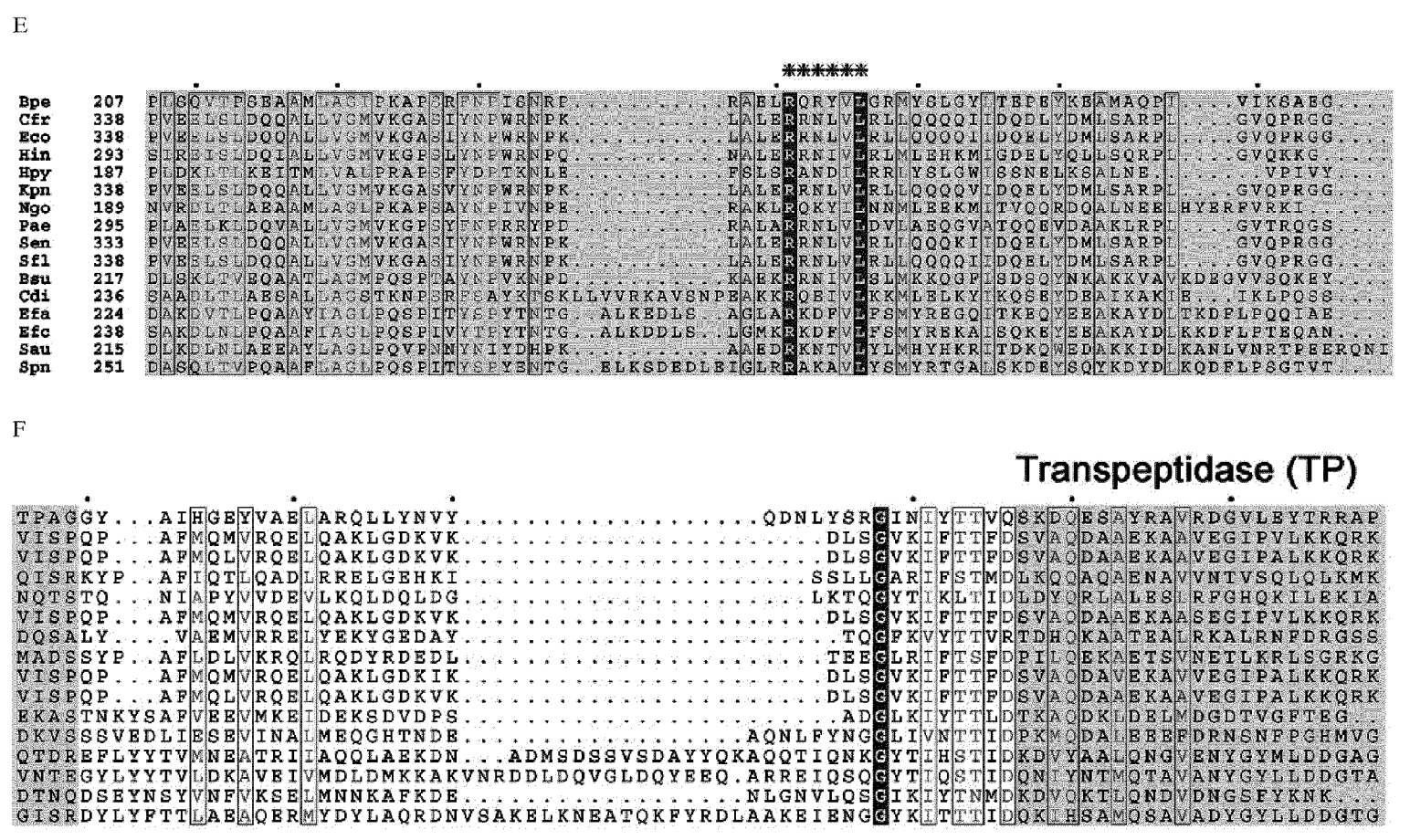
Figure 2:
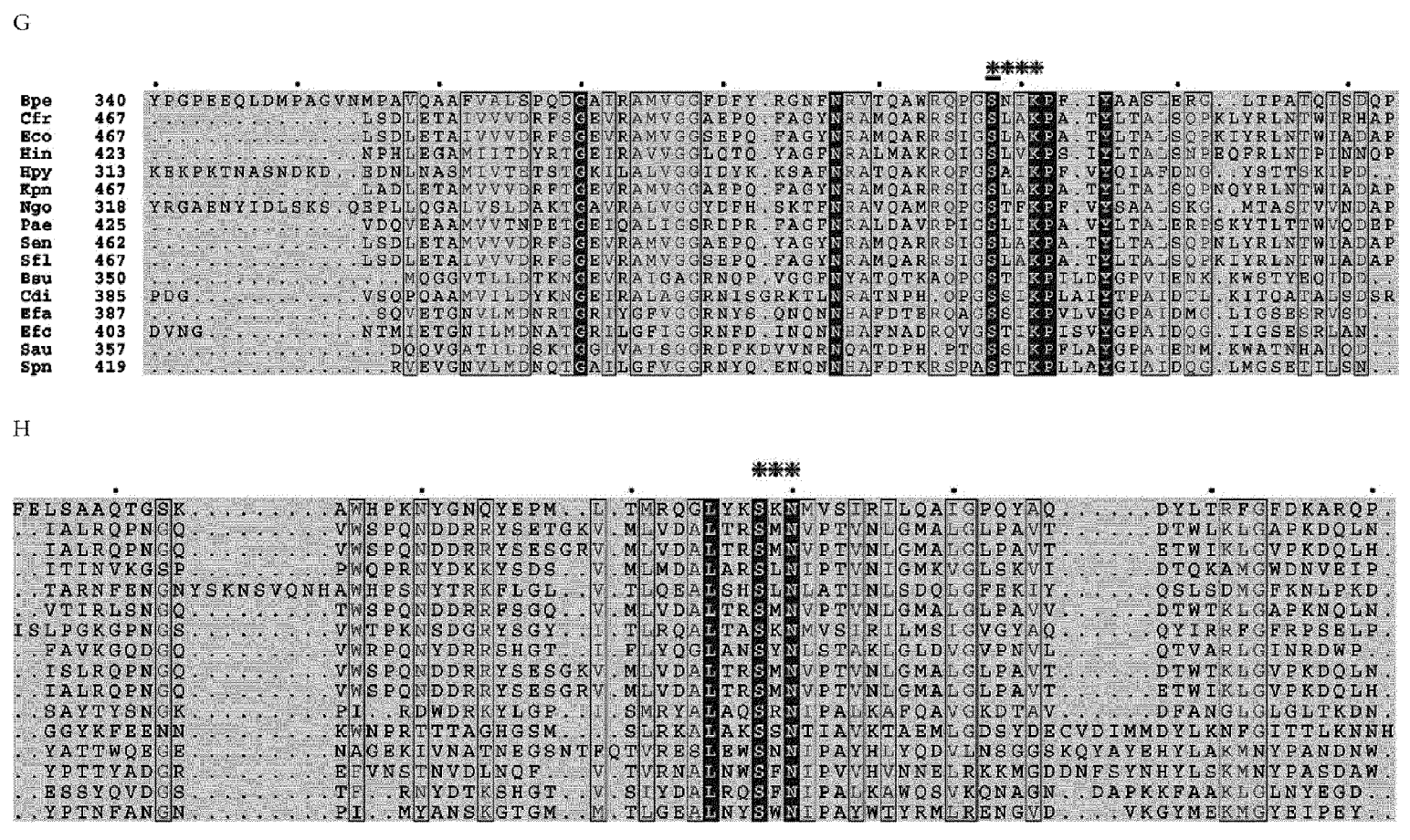
Figure 2:
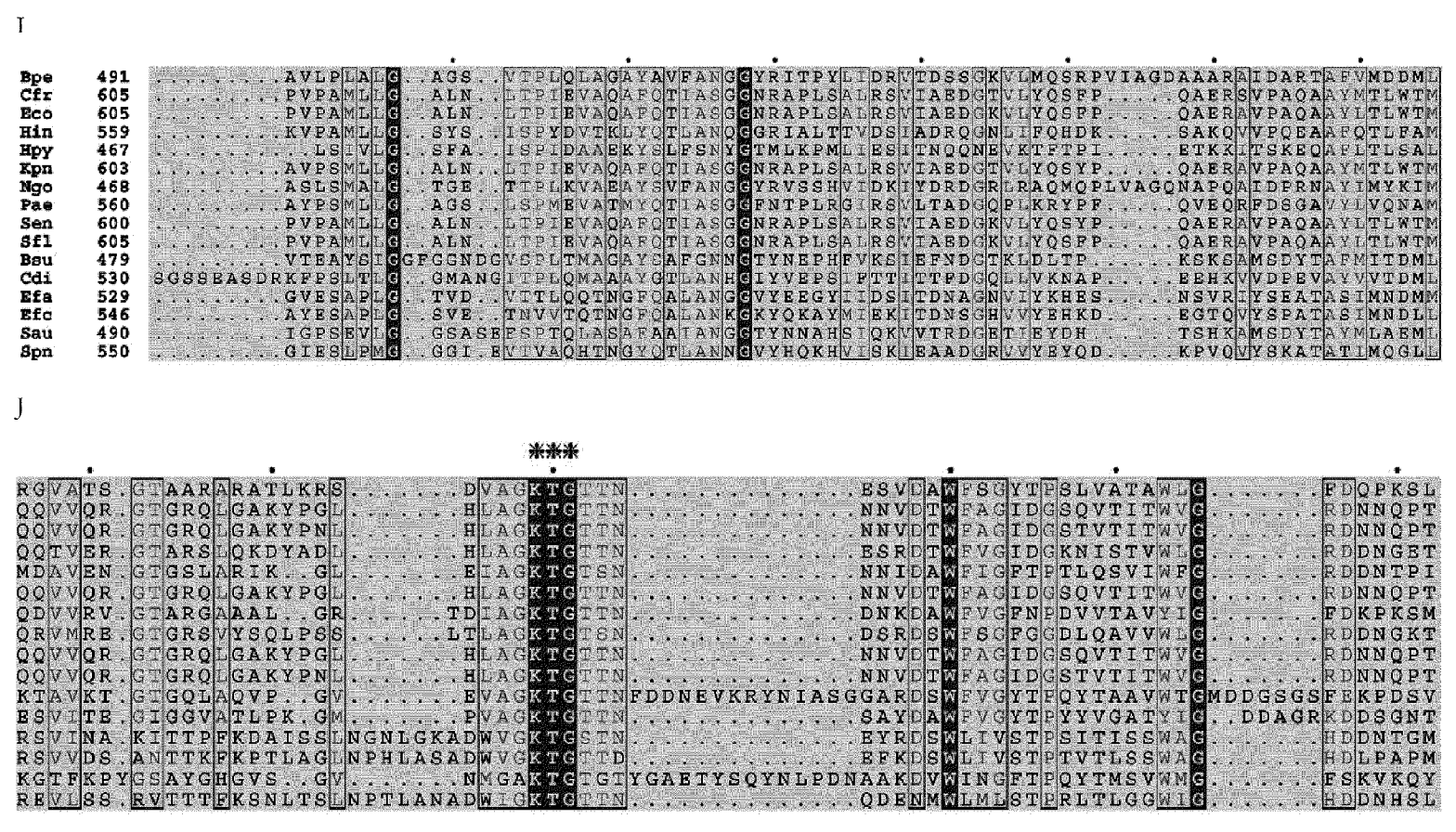

FIG. 2 shows sequence alignment of full-length bi-functional PBPs from 16 bacterial strains (Seq. ID Nos. 1-16). Each section A-L of FIG. 2 contains 16 rows, with each row corresponding to, in order, Seq. ID Nos. 1-16, respectively. The order of the aligned sequences, in rows, is identical to the order given in Table 1 and FIG. 3.

Each row of FIG. 2 is labeled with the following: "Bpe" (row 1) indicates PBP1b from *Bordetella pertussis* (Seq. ID No. 1); "Cfr" (row 2) indicates PBP1b from *Citrobacter freundii* (Seq. ID No. 2); "Eco" (row 3) indicates PBP1b from *Escherichia coli* (Seq. ID No. 3); "Hin" (row 4) indicates PBP1b from *Haemophilus influenzae* (Seq. ID No. 4); "Hpy" (row 5) indicates PBP1a from *Helicobacter pylori* (Seq. ID No. 5); "Kpn" (row 6) indicates PBP1b from *Klebsiella pneumoniae* (Seq. ID No. 6); "Ngo" (row 7) indicates PBP1 from *Neisseria gonorrhoeae* (Seq. ID No. 7); "Pae" (row 8) indicates PBP1b from *Pseudomonas aeruginosa* (Seq. ID No. 8); "Sen" (row 9) indicates PBP1b from *Salmonella enterica* (Seq. ID No. 9); "Sfl" (row 10) indicates PBP2 from *Shigella flexneri* (Seq. ID No. 10); "Bsu" (row 11) indicates PBP1a/1b from *Bacillus subtilis* (Seq. ID No. 11); "Cdi" (row 12) indicates PBP from *Clostridium difficile* (Seq. ID No. 12); "Efa" (row 13) indicates PBP2a from *Enterococcus faecalis* (Seq. ID No. 13); "Efc" (row 14) indicates PBP1 from *Enterococcus faecium* (Seq. ID No. 14); "Sau" (row 15) indicates PBP2 from *Staphylococcus aureus* (Seq. ID No. 15); "Spn" (row 16) indicates PBP1b from *Streptococcus pneumoniae* (Seq. ID No. 16).

Each of the 16 rows of FIG. 2 represents a sequence that continues through each of sections A-L of FIG. 2. Each sequence contains a Transmembrane (TM) domain, a Transglycosylase (TG) domain, and a Transpeptidase (TP) domain. Each domain is represented by gray background shading, with the type of domain ("Transmembrane (TM)", "Transglycosylase (TG)", or "Transpeptidase (TP)") identified by a label at the beginning of each domain (section of gray shading). Conserved residues are represented by boxes of thin black lines that encompass one or more columns. Where a set of conserved residues (i.e., conserved residues in a given column) contains some similarities among the 16 sequences, the text is shown in black or dark gray. Where a set of conserved residues contains identical entries across the 16 sequences, the column is represented with a black background and light text. Note that such columns represented with black background and light text indicate sets of conserved residues.

The sequences of FIG. 2 have been distributed such that beginning and end of each domain and the sets of conserved residues across the 16 sequences are aligned along vertical columns. To accomplish this, "gaps" have been provided, each represented by a ("."). Such "gaps" do not represent entries in the structural continuity of each sequence or characteristics thereof, but rather are provided only to accomplish the alignment described herein. Accordingly, the numbering of sequence entries (excluding gaps) is specific to each sequence. The number corresponding to the first entry in each row of FIGS. 2A, 2C, 2E, 2G, 2I, and 2K is given to the left of each said first entry. The dots above the top row of each section are provided to indicate the numbering of the first sequence ("Bpe"), occurring at intervals of 10 entries with respect to sequence "Bpe".

Stars above the top rows of FIG. 2 indicate the motif for TG: EDxxFxxHxxG, GxSTxTQQ, RKxxE, KxxILxxYxN, and RRxxVL, and the motif for TP: SxxK, SxN, and KTG. Underlined stars indicate catalytic residues. The 16 full-length PBP sequences used in this study were aligned with program Jalview and the figure was prepared with ESPript.

The target genes were amplified from respective genomic DNA from each individual bacterial species, and cloned into expression vectors for recombinant protein production using E. coli host. The enzymatic activities of the purified proteins were confirmed by lipid II polymerization (data not shown) and moenomycin binding were measured with SPR. As shown in Table 1, varied steady-state affinity ($K_D$) values were found among PBPs from different species. Nonetheless, all the measured $K_D$ values fell into the range of $10^{-7}$ M, close to the reported inhibition concentration for the transglycosylation process. Among the Gram-positive bacteria tested, the $K_D$ values of PBP from *E. faecalis* and *S. aureus* correlate with the MIC values, suggesting that the moenomycin binding site of PBP may be a good target for development of antibiotics against these species.

TABLE 1

Correlation of antimicrobial activity and PBP binding affinity of moenomycin for 16 bacterial strains

| Species | MIC, μM* | Reported values[†] MIC, μM | Citation | Gene sequence ID[‡] | SPR_$K_D$, nM[§] | FA_$K_D$, nM[¶] |
|---|---|---|---|---|---|---|
| Gram-negative | | | | | | |
| Bordetella pertussis | 0.011-0.021 | — | | PBP1a (NP_882163) | 1,270 | 594 ± 2.30 |
| Citrobacter freudii | — | 352 | 28 | PBP1b (CAA90232) | 728 | — |
| Escherichia coli | 80 | 55-110 | 28 | PBP1b (NP_414691) | 440 | 54 ± 17 |
| Haemophilus influenzae | — | — | | P8P1b (AAX88775) | 966 | 174 ± 13 |
| Helicobacter pylori | — | 1.3 | 29 | PBP1a (NP_207392) | 334 | 25 ± 14 |
| Klebsiella pneumoniae | 80 | 13.75-27.5 | 28 | P8P1b (NTUH-2044) | 819 | 78 ± 24 |
| Neisseria gonorrhoeae | — | 1.69 | 28 | PBP1 (YP_207272) | 450 | 47 ± 26 |
| Pseudomonas aeruginosa | 40 | 55-110 | 28 | PBP1b (YP_793163) | 866 | 42 ± 29 |
| Salmonella enterica | 160 | 13.75-110 | 38 | PBP1b (YP_149541) | 561 | 138 ± 113 |
| Shigella flexneri | 40 | 27.5-110 | 28 | PBP2 (YP688236) | 290 | — |
| Gram-positive | | | | | | |
| Bacillus subtilis | 0.3-0.6 | 0.07-0.43 | 30 | PBP1a/1b (NP_390113) | 1,690 | 197 ± 80 |
| Clostridium difficile | >160 | 220-440 | 30 | PBP (CAJ67615) | 582 | 37 ± 33 |
| Enterococcous faecalis | 0.075-0.3 | 0.1 | 31 | PBP2a (NP_814430) | 619 | 276 ± 14 |
| Enterococcous faecium | — | >40.5 | 10 | PBP1 (EAN08787) | 94 | 56 ± 11 |
| Staphytococcus aureus | 0.075 | 0.02-0.12 | 10 | PSP2 (NP_371974) | 393 | 30 ± 29 |
| Streptococcus pneumoniae | 0.625 | — | | PBP1b (NP_359500) | 900 | 38 ± 24 |

*MIC of moenomycin against different bacterial species.
[†]MIC values of moenomycin from the literature.
[‡]Sequence ID of class A PBP genes from individual bacterial strains. Homologs of class A PBPs were identified by using BLAST against the NCBI database.
[§]$K_D$ of PBP homologs and moenomycin using SPR. Average values are shown.
[¶]$K_D$ of PBP homologs and moenomycin using our FA-based assay.

Example 3

Expression and Purification of *E. coli* PBP1b Variants

Full-length PBP1b from *E. coli* (Swiss-Prot accession number P02919) was amplified from genomic DNA, cloned into the pET vectors (EMD Sciences, San Diego, Calif.), and expressed with an N-terminal (His)$_6$ tag. BL21(DE3) *E. coli* host cells were grown at 37° C. until OD at 600 nm reached 0.6 and protein expression was induced with 1 mM IPTG for 3 hours. Cell pellets were resuspended in 20 mM Tris at pH 8.0, 300 mM NaCl and broken by Microfluidizer (Microfluidics, Newton, Mass., USA). The solubilization and purification of the recombinant full-length membrane proteins were tested with various detergents (Anatrace, Maumee, Ohio, USA), including n-decyl-β-D-maltopyranoside, n-undecyl-β-D-maltopyranoside, n-dodecyl-β-D-maltopyranoside, n-octyl-β-D-glucopyranoside, n-nonyl-β-D-glucopyranoside, n-tetradecylphosphocholine, n-dodedyl-N,N-dimethylamine-N-oxide, CHAPS (3-[(3-Cholamidopropyl)-dimethylammonio]-1-propane sulfonate) and Triton X-100 (α-[4-(1,1,3,3-Tetramethylbutyl)phenyl]-w-hydroxy-poly(oxy-1,2-ethanediyl)). Among them, DDM (n-dodecyl-β-D-maltopyranoside) was found to solubilize the full-length PBP1b and retain its moenomycin binding activities. Therefore, full-length PBP1b was solubilized with 20 mM DDM and purified by Nickel chelation chromatography following manufacturer's instruction in the presence of 1 mM DDM.

The domains of PBP1b are defined as: transmembrane (TM, residues 64-87), transglycosylase (TG, residues 195-409) and transpeptidase (TP, residues 444-736). Nucleotide primers were designed to amplify respective variants containing TG+TP (residues 88-844), TM+TG (residues 1-409), TG (residues 195-409), and TP (residues 444-736). The amplified products were cloned into pET vectors for expression and purification. The procedure to obtain the variant TM+TG was as described for full-length protein preparations. For the variants TG+TP, TG and TP, 13 mM n-tetradecylphosphocholine (Anatrace) was used for protein extraction and 0.25 mM for Nickel chelation chromatography. The detergent was exchanged to 1 mM DDM and concentrated using Amicon Ultra filter units (Millipore, Billerica, Mass., USA).

Example 4

Expression and Purification of Recombinant Full-Length Bi-Functional PBPs from 16 Bacterial Strains Homologs of full-length bi-functional PBPs were identified with BLAST against NCBI database using PBP1b protein sequence from *E. coli* (Swiss-Prot accession number P02919). To confirm the presence of the transglycosylase motifs and active sites, the sequences were aligned using program Jalview (4) with MUSCLE multiple alignment algorithm (5), and the alignment output (FIG. 2) were prepared with ESPript (6). The following residues are omitted in the alignment for clarity, Bpe (*B. pertussis*): 354-443, Ngo (*N. gonorrhoeae*): 331-416, Bsu (*B. subtilis*): 615-643, 735-787, 797-835 and 897-914, and Cdi (*C. difficile*): 267-322 and 804-842.

Figure 3:
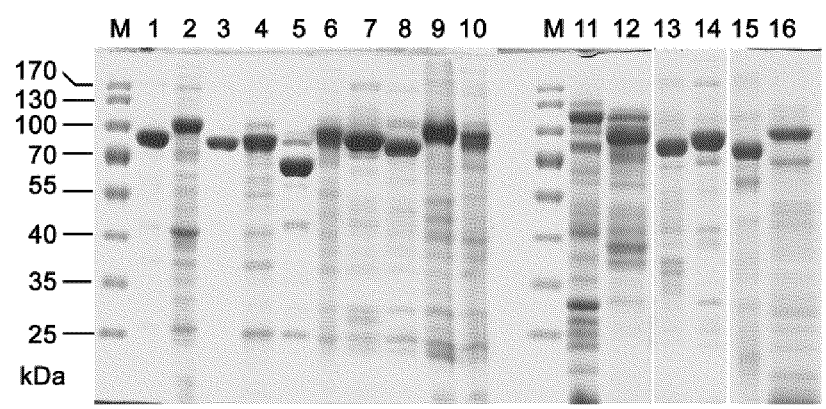
FIG. 3 shows the SDS-PAGE analysis of purified protein of class A PBPs from sixteen bacterial species, according to implementations of the present disclosure.

FIG. 3 shows the SDS-PAGE analysis of purified protein of class A PBPs from sixteen bacterial species. Each lane contains 5 μg of protein and M denotes molecular weight markers in kDa. 1: PBP1a from *Bordetella pertussis* (Seq. ID No. 1), 2: PBP1b from *Citrobacter freundii* (Seq. ID No. 2), 3: PBP1b from *Escherichia coli* (Seq. ID No. 3), 4: PBP1b from *Haemophilus influenzae* (Seq. ID No. 4), 5: PBP1a from *Helicobacter pylori* (Seq. ID No. 5), 6: PBP1b from *Klebsiella pneumoniae* (Seq. ID No. 6), 7: PBP1 from *Neisseria gonorrhoeae* (Seq. ID No. 7), 8: PBP1b from *Pseudomonas aeruginosa* (Seq. ID No. 8), 9: PBP1b from *Salmonella enterica* (Seq. ID No. 9), 10: PBP2 from *Shigella flexneri* (Seq. ID No. 10), 11: PBP1a/1b from *Bacillus subtilis* (Seq. ID No. 11), 12: PBP from *Clostridium difficile* (Seq. ID No. 12), 13: PBP2a from *Enterococcus faecalis* (Seq. ID No. 13), 14: PBP1 from *Enterococcus faecium* (Seq. ID No. 14), 15: PBP2 from *Staphylococcus aureus* (Seq. ID No. 15), 16: PBP1b from *Streptococcus pneumoniae* (Seq. ID No. 16).

For expression of individual PBPs, genomic DNAs were purchased from American Type Culture Collection (ATCC, Manassas, Va., USA). The recombinant proteins of the full-length genes from 16 bacteria, including *Escherichia coli, Klebsiella pneumoniae, Streptococcus pneumoniae, Shigella flexneri, Haemophilus influenzae, Helicobacter pylori, Citrobacter freundii, Bordetella pertussi, Staphylococcus aureus* (MRSA Mu50), *Bacillus subtilis, Pseudomonas aeruginosa, Clostridium difficile, Enterococcus faecium, Enterococcus faecalis, Salmonella enterica* and *Neisseria gonorrhoeae*, were prepared using the same protocols as described for the full-length *E. coli* PBP1b. Most of them can be obtained with purity greater than 80% (FIG. 3) and used for binding experiments.

Example 5

Surface Plasmon Resonance Detection

Purified PBP and its variants were immobilized onto CM3 chip (GE healthcare, Uppsala, Sweden) to about 1,500~2,000 RU via amine-coupling method. The chips were then passed over with different concentrations of moenomycin A (0-2000 nM). Immobilization and data collection were performed with BIAcore T100 (GE Healthcare, Uppsala, Sweden) at 25° C.

Example 6

Fluorescence Anisotropy Measurements

Fluorescence anisotropy measurements were carried out in triplicates in the wells of 384-well plates using a laser fluorimetry equipped with a 488 nm laser (IsoCyte, Blueshift Biotech, Inc., Sunnyvale, Calif., USA). Various buffers, salts, pH values, and divalent cations ($Ca^{++}$, $Mg^{++}$, $Co^{++}$) were optimized for fluorescence anisotropy measurements. $K_D$ and $K_I$ determinations were carried out in 100 mM NaCl, 10 mM Tris, pH 8.0. The scanning focus was above the plate bottom to avoid detection interferences. Data analysis was performed with the proprietary software, BlueImage (Blueshift Biotech Inc). Fluorescence anisotropy values (A) were calculated using the equation: $A=(I_\parallel - G^*I_\perp)/(I_\parallel + 2G^*I_\perp)$, where $I_\parallel$ is the fluorescence intensity of emitted light parallel to excitation, $I_\perp$ is the fluorescence intensity of emitted light perpendicular to excitation, and G is the gating factor that corrects for instrument bias. The G factor is experimentally determined for each run using the probe-only well as the basal an isotropy.

FIG. 4 shows the design of a novel fluorescence anisotropy assay for transglycosylase, according to implementations of the present disclosure.

Based on the conclusion that the full-length proteins shall be used for moenomycin binding studies, a fluorescence anisotropy (FA)-based assay was thus designed to monitor the binding affinities of small molecules towards TG. Previous studies on the complex crystal structure and the structure-activity relationship suggested that the modification of compound 1 to 2 (FIG. 4A) will not dramatically reduce the binding and antibacterial activities. FIG. 4(A) shows the chemical structures of the modified moenomycin A (2). Furthermore, the amino moiety in 2 allows the conjugation with any fluorophore as a moenomycin-based probe for binding studies. Indeed, compound 2 was readily linked with a fluorescein (6-carboxyfluoresein N-hydroxysuccinimide ester) under basic conditions to prepare the fluorescent probe 3 (F-Moe, FIG. 4B). FIG. 4(B) shows the chemical structures of the fluorescein-labeled moenomycin, F-Moe (3). One major concern about the fluorescent probe used in the FA assay is the probe itself; either the fluorophore or the structure modification, may interfere with the binding between the targeted protein and the small molecule. Therefore, the PBP binding affinities of Moe A and the fluorescent probe were compared using SPR. The determined steady-state affinity ($K_D$) values are similar for Moe A and F-Moe ($4.4\times10^{-7}$ vs. $5.2\times10^{-7}$ M) (FIGS. 4C and 4D).

FIG. 4(C) shows the SPR analysis of the binding activity of moenomycin A to *E. coli* PBP1b, and FIG. 4(D) shows the SPR analysis of the binding activity of F-Moe to *E. coli* PBP1b. Responses for moenomycin binding to immobilized *E. coli* PBP1b were shown. The data were analyzed using steady-state affinity and fitted to a 1:1 interaction model, as shown in the inset graph. The $K_D$ values deduced from the intercepts of X-axis and the dotted lines, are $4.4\times10^{-7}$ M and $5.161\times10^{-7}$ M for Moe A and F-Moe, respectively.

The result confirms that F-Moe is a valid fluorescence probe useful for the FA-based PBP binding assay.

FIG. 5 shows the development of high-throughput FA assay for transglycosylase. FIG. 5(A) shows the concentration-dependent changes in fluorescence anisotropy observed when *E. coli* PBP1b bound to F-Moe. FIG. 5(B) shows the improved FA assay with the *Helicobacter pylori* PBP1a. The concentration-dependent fluorescence anisotropy changes were performed similarly using the *H. pylori* PBP1a. The maximum anisotropy value was 0.2. FIG. 5(C) shows the displacement of the PBP1a bound F-Moe complex by unlabeled moenomycin at various concentrations. The changes in fluorescence anisotropy is defined as $[(A_{obs}-A_{min})/(A_{max}-A_{min})\times100\%]$. The $K_D$ and $IC_{50}$ value was calculated as described in example 2.

The anisotropy of F-Moe increased significantly by incubation with *E. coli* PBP1b, supposedly due to the formation of F-Moe-PBP1b complex (FIG. 5A). In contrast, the anisotropy of F-Moe was unchanged when incubated with bovine serum albumin, up to 100 μM (data not shown). The protein concentrations were further titrated down to establish the dose-dependency of the anisotropy changes. The deduced dissociation constant ($K_D$) for F-Moe was in the sub-micromolar range (54±17 nM) for *E. coli* PBP1b (FIG. 5A). However, the signal-to-noise ratio of FA assay using the *E. coli* PBP1b is of limited satisfaction with the maximum anisotropy equal to 0.120. Different class A PBPs were screened to improve the assay. Of all homologs tested, the FA assay using *Helicobacter pylori* PBP1a produced the best signal-to-noise ratio with $K_D$ of 25±14 nM, and with the anisotropy increases from 0.018 to 0.2 upon binding to F-Moe (FIG. 5B). For the development of an assay for inhibitor screening, F-Moe was pre-incubated with *H. pylori* PBP1a and then competed with unlabeled Moe A at various concentrations. A decrease in anisotropy was observed as the concentration of Moe A increased, resulting in the $K_I$ (inhibition constant) and $IC_{50}$ values as 0.47±0.10 μM and 0.36 μM, respectively (FIG. 5C). The result validates the FA assay to screen for inhibitors that displace the probe competitively from the moenomycin binding pocket of PBP.

Example 7

Determination of $K_D$ Values from Direct Binding Assay

For direct binding assay, the initial condition contained 40 μl of 100 nM F-Moe in 10 mM Tris, pH 8.0, 100 mM NaCl.

After a small volume of PBP stock was added, the anisotropy change was measured after a 5-minute equilibration. We assume that the direct titration follows a simple binding equilibrium between Ligand (L) and Receptor (R)

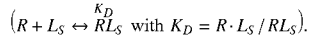

The data was fitted to the [Eq. 1] using Prism (GraphPad Software, San Diego, Calif.) for the determination of $K_D$ (3):

$$(A_{obs}-A_{min})/(A_{max}-A_{min})=(K_D+L_{ST}+R_T)-[(K_D+L_{ST}+R_T)^2-4 \cdot L_{ST} R_T]^{1/2}$$  [Eq. 1]

where $A_{obs}$ is the observed anisotropy; $A_{min}$ is the minimum anisotropy; $A_{max}$ is the maximum anisotropy; $L_{ST}$ is the total concentration of F-Moe, $R_T$ is the total concentration of PBP, and $K_D$ is the dissociation constant between the ligand (F-Moe) and the receptor (PBP). The reported value is the average of four different runs.

Example 8

Determination of $K_I$, and $IC_{50}$ Values from Competitive Displacement Assay For displacement assay, the initial condition contained 40 µl of 100 nM F-Moe, 10 µg/ml *H. pylori* PBP1a in 10 mM Tris, pH 8.0, 100 mM NaCl. Aliquots of compound stock solution were added and the anisotropy was monitored after 5 minutes of equilibration. The data from the displacement assay was used to calculate the inhibition constant ($K_I$) and $IC_{50}$ value of an inhibitor using the complete competitive binding model

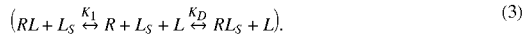

The $K_I$ value was determined by plotting the total inhibitor concentration (C) versus the molar ratio of bound/free F-Moe and fitting the resulting curve to [Eq. 2], $$C=[(K_I/K_D*X)+1][R_T-(L_{ST}*X)/(X+1)-K_D*X$$  [Eq. 2]

$$X=Bound/Free=(A_{obs}-A_{min})/(A_{max}-A_{obs})$$

where $A_{obs}$ is the observed anisotropy at a particular concentration of a compound (C), $A_{min}$ is the minimum anisotropy, $A_{max}$ is the maximum anisotropy, $L_{ST}$ is the total concentration of F-Moe, $R_T$ is the total concentration of PBP1a, $K_D$ is the dissociation constant between the ligand (F-Moe) and the receptor (PBP) and $K_I$ is the dissociation constant between the inhibitor and PBP1a. The reported value is the average of four different runs.

For $IC_{50}$ determination, the fraction of bound fluorescent probe is plotted versus the log value of the competitor concentration (C). Fitting the resulting sigmoidal curve using [Eq. 3] would result in an $IC_{50}$ value, $$(A_{obs}-A_{min})/(A_{max}-A_{min})=1/(1+10^{((C-\log(IC_{50}))*\text{Hill slope})})$$  [Eq. 3]

where $A_{obs}$ is the observed anisotropy at a particular concentration of a compound (C), $A_{min}$ is the minimum anisotropy, $A_{max}$ is the maximum anisotropy.

Example 9

High-Throughput Screening for Transglycosylase Inhibitors

The FA assay was used to screen against 50,000 purchased small molecules (ChemBridge Inc., San Diego, Calif., USA) and 7,000 from proprietary collections. The compounds were transferred to 96-well plates (Freedom Evo, Tecan Schweiz AG, Männedorf, Switzerland) and then to 384-well plates using a multi-dispenser (Labcyte, Sunnyvale, Calif., USA) to prepare the compound plates for screening. The *H. pylori* PBP1a (10 µg/ml) in 100 nM F-Moe, 10 mM Tris, 100 mM NaCl, pH 8.0 at a final volume of 40 µl was added to 384-well plates (Freedom Evo 150, Tecan). One µl of 2 mM compound stocks were added to wells using a multi-dispenser (Labcyte). The last two columns of every plate were controls with 10 µM moenomycin and 2.5% DMSO, respectively. After a 30-minute incubation, changes in fluorescence anisotropy were determined with Isocyte (Blueshift Biotech Inc). Hits that showed greater than 75% reduction compared to the control anisotropy values were selected for further confirmation.

Several moenomycin analogues (2, 4, and 5) were prepared to evaluate the reliability of the FA-based assay. As shown in Table 2, the differential binding affinities (the $IC_{50}$ values) of these moenomycin analogues by the FA-based assay are comparable with the published reports. The modification of moenomycin A to 2 resulted in a little decrease in TG binding affinities. Dimerization of 2 via an eight-carbon spacer produced 4 with a two-fold increase over 2 in both PBP binding and the antimicrobial potencies, although 4 is still less potent than Moe A (1). More significantly, compound 5 without the C25 lipid moiety could hardly displace the F-Moe probe 3, indicating that the hydrophobic part of moenomycin is crucial to the binding to the full-length PBP1b. It is noteworthy that the order in inhibition potency is in agreement with that of MIC values (Table 2).

TABLE 2

Inhibition of TG activity and the antibacterial determinations of selected hits

| | | MIC, µM[‡] | | | |
| --- | --- | --- | --- | --- | --- |
| Compound* | $IC_{50}$, µM[†] | B. subtilis (ATCC23857) | E. faecalis (ATCC29212) | S. aureus (ATCC29213) | S. pneumoniae (ATCC49619) |
| 1 | 0.36 | 0.33 | 0.04 | <0.01 | 0.33 |
| 2 | 2.10 | 2.50 | 10.0 | 1.25 | 20.0 |
| 4 | 0.92 | 1.25 | 5.0 | 0.625 | 20.0 |
| 5 | 125.00 | — | — | — | — |

TABLE 2-continued

Inhibition of TG activity and the antibacterial determinations of selected hits

| | | MIC, µM[‡] | | | |
|---|---|---|---|---|---|
| Compound* | IC$_{50}$, µM[†] | B. subtilis (ATCC23857) | E. faecalis (ATCC29212) | S. aureus (ATCC29213) | S. pneumoniae (ATCC49619) |
| 6 | 34.00 | 0.25 | 0.25 | 1.0 | 4.0 |
| 7 | 3.70 | 0.25 | 1.0 | 4.0 | — |
| 8 | 9.30 | 4.0 | >4.0 | >4.0 | >4.0 |

*Compounds 2, 4, and 5 are moenomycin derivatives. Compounds 6-8 were HTS hits.
[†]IC$_{50}$ values were determined by using the fluorescence anisotropy assay shown in FIG. 5A.
[‡]The MICs of moenomycin against different bacterial species were determined as described in Materials and Methods. ATCC, American Type Culture Collection.

The FA assay was used to screen a collection of 57,000 small molecules along with Moe A derivatives (FIG. 6) at 50 µM. FIG. 6 illustrates chemical structures of moenomycin derivatives (4 and 5), according to implementations of the present disclosure.

High controls are assays with 1 µM of moenomycin and low controls are assays with 2.5% DMSO. Other proteins, such as bovine serum albumin, were also included as a control to confirm that the anisotropy increase is not from non-specific binding.

FIG. 7 illustrates screening for small molecules as TG inhibitors using the class A PBPs, according to implementations of the present disclosure. FIG. 7(A) shows the scheme of HTS for TG inhibitors using FA assay. Protein structure graphics were created from PDB ID 2OLV (12). 7(B) shows chemical structures of the HTS hits (compounds 6-8).

Z' value, a statistical parameter ranging from 0 to 1 to evaluate the robustness of high-throughput screening, was determined as 0.895 from more than 100 independent experiments. Eleven possible hits that showed at least 75% inhibition in the screening were selected for additional studies involving antimicrobial assays and IC$_{50}$ values determinations for PBP binding (FIG. 7A). Among which, two moenomycin analogues (2 and 4) and three small molecules (compounds 6, 7 and 8) were confirmed to have both antibacterial and the TG binding inhibition activities (Table 2). Respectively, compounds 6, 7 and 8 are (Z)-5-(4-bromophenyl)-3-((5-nitrofuran-2-yl)methylene)furan-2(3H)-one(Z)-1,3-diphenyl-4-(2-(thiazol- 2-yl)hydrazono-1H-pyrazol-5(4H)-one; (E)-4-(2-(5,5,8,8,-tetramethyl-5,6,7,8-tetrahydronaphthalen-2-yl)prop-1-enyl)benzoic acid.

Using the FA-based assay, a hit rate of 0.02% was achieved with the Z' value equal to 0.895.

Example 10

Determination of Minimal Inhibitory Concentration (MIC)

The minimal inhibitory concentration (MIC) of tested compounds was determined following the NCCLS standard. The experiments were conducted in 96-well microtiter plates using two-fold dilutions in Muller-Hilton broth with (*Streptococcus pneumonia*) or without blood (*Bacillus subtilis, Enterococcus faecalis, Staphylococcus aureus*). Exponentially growing cells at 5×10$^5$ cells/ml were incubated with test compounds at various concentrations. After an 18 h to 24 h incubation at 37° C., MIC was determined as the minimal concentration of the compound that prevents bacterial growth.

While the apparatus and method have been described in terms of what are presently considered to be the most practical and preferred implementations, it is to be understood that the disclosure need not be limited to the disclosed implementations. It is intended to cover various modifications and similar arrangements included within the spirit and scope of the claims, the scope of which should be accorded the broadest interpretation so as to encompass all such modifications and similar structures. The present disclosure includes any and all implementations of the following claims.

The invention claimed is:

1. A method for high throughput screening (HTS) of antibacterial agents, the method comprising:
   providing a candidate agent for screening;
   providing a class A penicillin-binding protein, or fragment thereof (PBP), from a bacterial species, comprising at least a transmembrane (TM) domain and a transglycosylase (TG) domain;
   determining a first binding affinity of the candidate agent to the at least transmembrane (TM) domain and transglycosylase (TG) domain-containing fragment of the class A penicillin-binding protein;
   comparing the first binding affinity to a second binding affinity of the candidate agent to a class A penicillin-binding protein fragment that lacks the TM domain;
   identifying a candidate agent as a putative transglycosylase inhibitor of the bacterial species as the antibacterial agent, wherein the candidate agent exhibits a higher first binding affinity to the transmembrane (TM) domain-containing class A penicillin-binding protein, or fragment thereof, as compared to the second binding affinity to the PBP fragment that lacks the TM domain; and
   confirming the transglycosylase inhibitor activity of the putative transglycolase inhibitor by testing for an ability to inhibit growth of the same bacterial species whose PBP transmembrane domain-containing fragment it binds with higher affinity,
   wherein the binding affinity between the candidate agent and the transmembrane (TM) domain of the class A penicillin-binding protein is determined by anisotropy measurement assay.

2. The method of claim 1, wherein the anisotropy measurement assay is at least one of a competition displacement assay or a direct binding assay.

3. The method of claim 2, wherein the competition displacement assay competes a labeled moenomycin with the candidate.

4. The method of claim 1, wherein the class A penicillin-binding protein comprises three domains which, from N terminus to C terminus, are transmembrane, transglycosylase, and transpeptidase domains.

5. The method of claim 1, wherein the bacterial species is *Escherichia coli, Klebsiella pneumoniae, Streptococcus pneumoniae, Shigella flexneri, Haemophilus influenzae, Helicobacter pylori, Citrobacter freundii, Bordetella pertussi, Staphylococcus aureus* (MRSA Mu50), *Bacillus subtilis, Pseudomonas aeruginosa, Clostridium difficile, Enterococcus faecium, Enterococcus faecalis, Salmonella enterica* or *Neisseria gonorrhoeae*.

6. The method of claim 1, further comprising:
   using a high throughput device comprising a platform with a plurality of versions of class A penicillin-binding protein, or fragment thereof, comprising at least transmembrane and a transglycosylase domain from a plurality of bacterial species;
   determining the binding affinity of the candidate agent to the multiple versions of class A penicillin-binding protein, or fragment thereof; and
   identifying a candidate agent as an effective transglycosylation agent for the bacterial species based on a binding affinity to the corresponding class A penicillin-binding protein, or fragment thereof.

7. The method of claim 6, wherein the plurality of class A penicillin-binding proteins, or fragments thereof are immobilized on a solid substrate or chip.

8. The method of claim 7, wherein the plurality of class A penicillin-binding proteins, or fragments thereof are immobilized on the solid substrate or chip by amine coupling.

9. The method of claim 1, wherein the anisotropy measurement of PBP binding, comprises a fluorescence anisotropy (FA) assay.

10. The method of claim 9, wherein a fluorescein-labeled moenomycin is used in the fluorescence anisotropy (FA) assay.

11. The method of claim 2, further comprising:
    determining the inhibition constant ($K_I$) and $IC_{50}$ values from the competition displacement assay.

12. The method of claim 2, further comprising:
    determining the dissociation constant ($K_D$) value from the direct binding assay.

13. The method of claim 1, wherein the candidate agent is a small molecule.

* * * * *